United States Patent
Chen et al.

(10) Patent No.: US 10,813,974 B2
(45) Date of Patent: Oct. 27, 2020

(54) METHODS FOR TREATMENT OF HBV INFECTION

(71) Applicant: ELIXIRON IMMUNOTHERAPEUTICS (HONG KONG) LIMITED, Hong Kong (CN)

(72) Inventors: Hung-Kai Chen, Taipei (TW); Daw-Tsun Shih, Taipei (TW); Cheng-Lun Ku, Taipei (TW); Pei-Han Chung, Taipei (TW)

(73) Assignee: ELIXIRON IMMUNOTHERAPEUTICS (HONG KONG) LIMITED, Hong Kong (CN)

( * ) Notice: Subject to any disclaimer, the term of this patent is extended or adjusted under 35 U.S.C. 154(b) by 0 days.

(21) Appl. No.: 16/889,483

(22) Filed: Jun. 1, 2020

(65) Prior Publication Data

US 2020/0289603 A1 Sep. 17, 2020

Related U.S. Application Data

(63) Continuation of application No. PCT/US2019/024663, filed on Mar. 28, 2019, which is a continuation of application No. PCT/CN2018/085836, filed on May 7, 2018.

(60) Provisional application No. 62/650,195, filed on Mar. 29, 2018.

(51) Int. Cl.
| | |
|---|---|
| A61K 39/00 | (2006.01) |
| A61K 39/395 | (2006.01) |
| C07K 16/24 | (2006.01) |
| C07K 16/00 | (2006.01) |
| A61K 9/00 | (2006.01) |
| A61K 38/04 | (2006.01) |
| A61K 39/29 | (2006.01) |
| A61P 31/20 | (2006.01) |

(52) U.S. Cl.
CPC .......... *A61K 38/04* (2013.01); *A61K 39/292* (2013.01); *A61P 31/20* (2018.01)

(58) Field of Classification Search
CPC .......... A61K 2300/00; A61K 2039/505; A61P 43/00; A61P 35/00; A61P 31/12
See application file for complete search history.

(56) References Cited

U.S. PATENT DOCUMENTS

2015/0306112 A1 10/2015 Wu et al.

OTHER PUBLICATIONS

Franco, Ma et al., "Evidence for CD81 T-Cell Immunity to Murine Rotavirus in the Absence of Perforin, Fas, and Gamma Interferon," Journal of Virology, Jan. 1997, vol. 71, No. 1, pp. 479-486; abstract; p. 480, 2nd column, 5th paragraph; PMCID; PMC191075.
Finke, D. et al., "Gamma Interferon Is a Major Mediator of Antiviral Defense in Experimental Measles Virus-Induced Encephalitis," Journal of Virology, Sep. 1995, vol. 69, No. 9; pp. 5469-5474; abstract; p. 5470, 1st column, 3rd paragraph; PMCID; PMC189396.
Wieland, SF et al., "Searching for Interferon-Induced Genes that Inhibit Hepatitis B Virus Replication in Trangenic Mouse Hepatocytes," Journal of Virology, Jan. 2003, vol. 77, No. 2; pp. 1227-1236; abstract; p. 1329, 1st column, 4th paragraph; p. 1228, 1st column, 5th paragraph; p. 1232, 1st column, 2nd paragraph to 2nd column, 1st paragraph; DOI: 10.1128/JV1.77.2.1227-1236.2003.
Jackson, SS et al., "Anti-Gamma Interferon Antibodies Enhance the Immunogenicity of Recombinant Adenovirus Vectors." Clinical and Vaccine Immunology; Nov. 2011, vol. 18, No. 11; pp. 1969-1978; DOI: 10.1128/CVI.05180-11.
PCT/US19/24663 International Search Report and Written Opinion, dated Jun. 19, 2019.
Chen et al., "Estimation of seroprevalence of hepatitis B virus and hepatitis C virus in Taiwan from a large-scale survey of free hepatitis screening participants," J. Formos. Med. Assoc. (2007) 106(2):148-55.
Yang PL et al., "Immune effectors required for hepatitis B virus clearance," Proc Natl Acad Sci. USA Jan. 12, 2010; 107(2): 798-802.
Suri D et al., "Non-cytolytic inhibition of hepatitis B virus replication in human hepatocytes," J Hepatol. Dec. 2001; 35(6): 790-7.

*Primary Examiner* — Barry A Chestnut
(74) *Attorney, Agent, or Firm* — FisherBroyles LLP; Adam Whiting

(57) ABSTRACT

The present invention provides methods for treating hepatitis B virus (HBV) infection using antibodies which specifically bind to human IFNγ.

28 Claims, 15 Drawing Sheets

Specification includes a Sequence Listing.

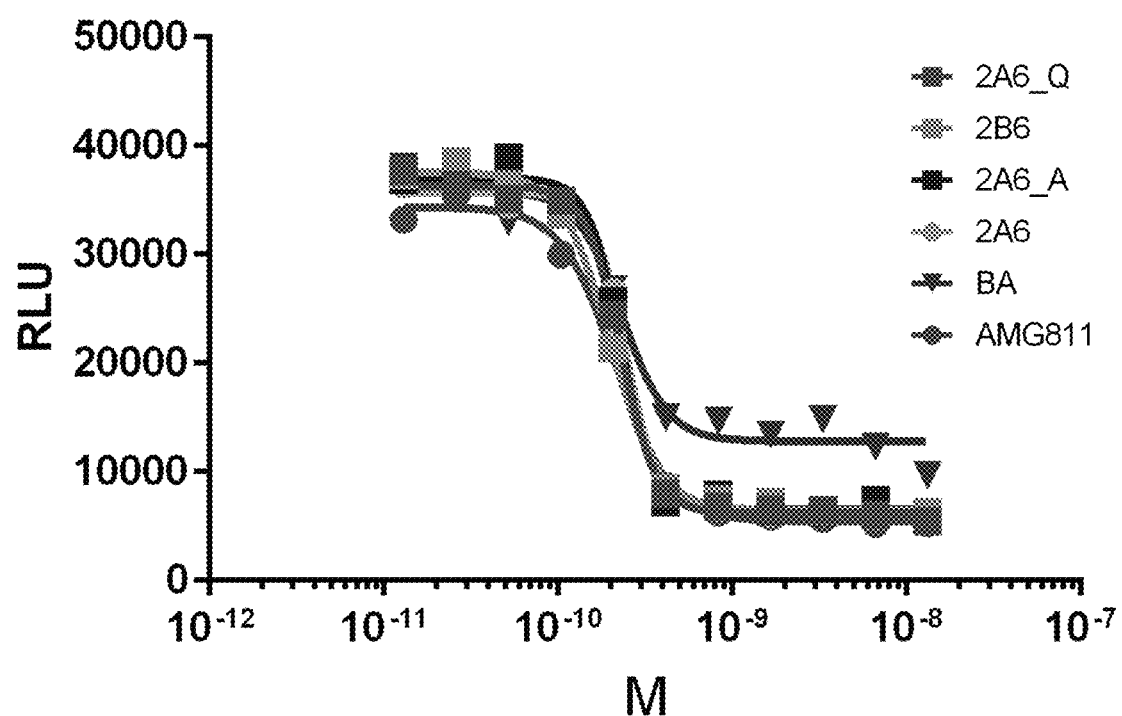

FIG. 9
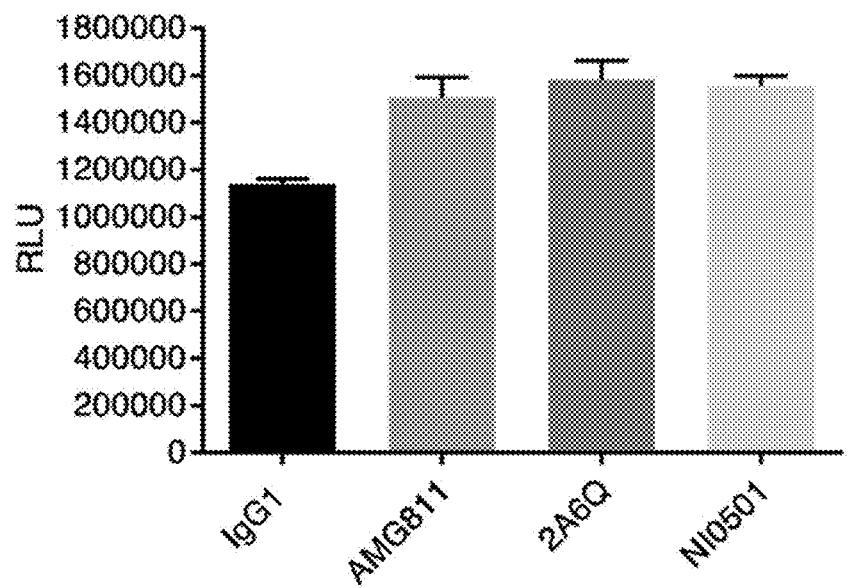
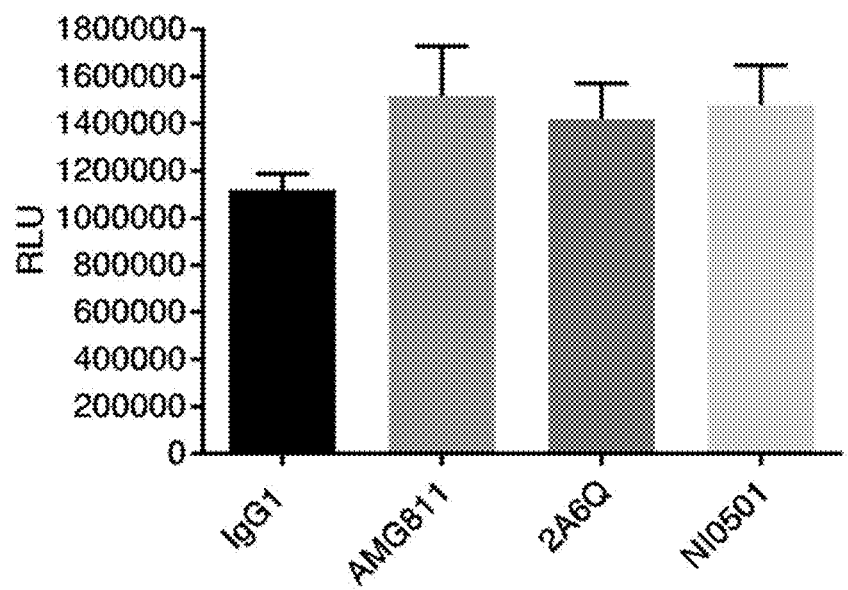

SEQUENCE LISTING

```
<160> NUMBER OF SEQ ID NOS: 188

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
accatggact gsacctggag                                              20

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
caccatggac acactttgct mcac                                         24

<210> SEQ ID NO 3
<211> LENGTH: 24
<212> TYPE: DNA
<213> ORGANISM: Artificial Sequence
<220> FEATURE:
```

```
<223> OTHER INFORMATION: PRIMER

<400> SEQUENCE: 3
accatggaca tactttgttc cacg                                        24

<210> SEQ ID NO 4
<211> LENGTH: 20
<212> TYPE: DNA
<213> ORGANISM: Artificial Sequence
<220> FEATURE:
<223> OTHER INFORMATION: PRIMER

<400> SEQUENCE: 4
atggagtttg ggctgagctg                                             20

<210> SEQ ID NO 5
<211> LENGTH: 20
<212> TYPE: DNA
<213> ORGANISM: Artificial Sequence
<220> FEATURE:
<223> OTHER INFORMATION: PRIMER

<400> SEQUENCE: 5
atggaactgg ggctccgctg                                             20

<210> SEQ ID NO 6
<211> LENGTH: 20
<212> TYPE: DNA
<213> ORGANISM: Artificial Sequence
<220> FEATURE:
<223> OTHER INFORMATION: PRIMER

<400> SEQUENCE: 6
atggagttgg ggctgtgctg                                             20

<210> SEQ ID NO 7
<211> LENGTH: 21
<212> TYPE: DNA
<213> ORGANISM: Artificial Sequence
<220> FEATURE:
<223> OTHER INFORMATION: PRIMER

<400> SEQUENCE: 7
catggagttt gggcttagct g                                           21

<210> SEQ ID NO 8
<211> LENGTH: 21
<212> TYPE: DNA
<213> ORGANISM: Artificial Sequence
<220> FEATURE:
<223> OTHER INFORMATION: PRIMER

<400> SEQUENCE: 8
catggagttt tggctgagct g                                           21

<210> SEQ ID NO 9
<211> LENGTH: 24
<212> TYPE: DNA
<213> ORGANISM: Artificial Sequence
<220> FEATURE:
<223> OTHER INFORMATION: PRIMER

<400> SEQUENCE: 9
catgaaacac ctgtggttct tcct                                        24
```

```
<210> SEQ ID NO 10
<211> LENGTH: 24
<212> TYPE: DNA
<213> ORGANISM: Artificial Sequence
<220> FEATURE:
<223> OTHER INFORMATION: PRIMER

<400> SEQUENCE: 10
aatgaagcac ctgtggttct tcct                                           24

<210> SEQ ID NO 11
<211> LENGTH: 25
<212> TYPE: DNA
<213> ORGANISM: Artificial Sequence
<220> FEATURE:
<223> OTHER INFORMATION: PRIMER

<400> SEQUENCE: 11
acatgaaaca tctgtggttc ttcct                                          25

<210> SEQ ID NO 12
<211> LENGTH: 20
<212> TYPE: DNA
<213> ORGANISM: Artificial Sequence
<220> FEATURE:
<223> OTHER INFORMATION: PRIMER

<400> SEQUENCE: 12
atggggtcaa ccgccatcct                                                20

<210> SEQ ID NO 13
<211> LENGTH: 27
<212> TYPE: DNA
<213> ORGANISM: Artificial Sequence
<220> FEATURE:
<223> OTHER INFORMATION: PRIMER

<400> SEQUENCE: 13
aatgtctgtc tccttcctca tcttcct                                        27

<210> SEQ ID NO 14
<211> LENGTH: 20
<212> TYPE: DNA
<213> ORGANISM: Artificial Sequence
<220> FEATURE:
<223> OTHER INFORMATION: PRIMER

<400> SEQUENCE: 14
saggtgcagc tggtgsagtc                                                20

<210> SEQ ID NO 15
<211> LENGTH: 20
<212> TYPE: DNA
<213> ORGANISM: Artificial Sequence
<220> FEATURE:
<223> OTHER INFORMATION: PRIMER

<400> SEQUENCE: 15
caggtccagc ttgtgcagtc                                                20

<210> SEQ ID NO 16
<211> LENGTH: 20
<212> TYPE: DNA
<213> ORGANISM: Artificial Sequence
<220> FEATURE:
<223> OTHER INFORMATION: PRIMER
```

```
<400> SEQUENCE: 16
caggttcagc tggtgcagtc                                          20

<210> SEQ ID NO 17
<211> LENGTH: 22
<212> TYPE: DNA
<213> ORGANISM: Artificial Sequence
<220> FEATURE:
<223> OTHER INFORMATION: PRIMER

<400> SEQUENCE: 17
caggtccagc tggtacagtc tg                                       22

<210> SEQ ID NO 18
<211> LENGTH: 23
<212> TYPE: DNA
<213> ORGANISM: Artificial Sequence
<220> FEATURE:
<223> OTHER INFORMATION: PRIMER

<400> SEQUENCE: 18
caggtcacct garggagtct ggt                                      23

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gaggtgcagc tgttggagtc t                                        21

<210> SEQ ID NO 20
<211> LENGTH: 19
<212> TYPE: DNA
<213> ORGANISM: Artificial Sequence
<220> FEATURE:
<223> OTHER INFORMATION: PRIMER

<400> SEQUENCE: 20
cagstgcagc tgcaggagt                                           19

<210> SEQ ID NO 21
<211> LENGTH: 21
<212> TYPE: DNA
<213> ORGANISM: Artificial Sequence
<220> FEATURE:
<223> OTHER INFORMATION: PRIMER

<400> SEQUENCE: 21
caggtgcagc tacarcagtg g                                        21

<210> SEQ ID NO 22
<211> LENGTH: 21
<212> TYPE: DNA
<213> ORGANISM: Artificial Sequence
<220> FEATURE:
<223> OTHER INFORMATION: PRIMER

<400> SEQUENCE: 22
caggtacagc tgcagcagtc a                                        21

<210> SEQ ID NO 23
<211> LENGTH: 19
```

```
<212> TYPE: DNA
<213> ORGANISM: Artificial Sequence
<220> FEATURE:
<223> OTHER INFORMATION: PRIMER

<400> SEQUENCE: 23
caggtgcagc tggtgcaat                                                19

<210> SEQ ID NO 24
<211> LENGTH: 20
<212> TYPE: DNA
<213> ORGANISM: Artificial Sequence
<220> FEATURE:
<223> OTHER INFORMATION: PRIMER

<400> SEQUENCE: 24
ggtccccgct cagctcctgg                                               20

<210> SEQ ID NO 25
<211> LENGTH: 20
<212> TYPE: DNA
<213> ORGANISM: Artificial Sequence
<220> FEATURE:
<223> OTHER INFORMATION: PRIMER

<400> SEQUENCE: 25
agtcctcgct cagctcctgg                                               20

<210> SEQ ID NO 26
<211> LENGTH: 20
<212> TYPE: DNA
<213> ORGANISM: Artificial Sequence
<220> FEATURE:
<223> OTHER INFORMATION: PRIMER

<400> SEQUENCE: 26
gctccctgct cagctcctgg                                               20

<210> SEQ ID NO 27
<211> LENGTH: 20
<212> TYPE: DNA
<213> ORGANISM: Artificial Sequence
<220> FEATURE:
<223> OTHER INFORMATION: PRIMER

<400> SEQUENCE: 27
gctccttgct cagcttctgg                                               20

<210> SEQ ID NO 28
<211> LENGTH: 20
<212> TYPE: DNA
<213> ORGANISM: Artificial Sequence
<220> FEATURE:
<223> OTHER INFORMATION: PRIMER

<400> SEQUENCE: 28
cctgctactc tggctcccag                                               20

<210> SEQ ID NO 29
<211> LENGTH: 25
<212> TYPE: DNA
<213> ORGANISM: Artificial Sequence
<220> FEATURE:
<223> OTHER INFORMATION: PRIMER

<400> SEQUENCE: 29
```

-continued

```
atttctctgt tgctctggat ctctg                                                 25

<210> SEQ ID NO 30
<211> LENGTH: 23
<212> TYPE: DNA
<213> ORGANISM: Artificial Sequence
<220> FEATURE:
<223> OTHER INFORMATION: PRIMER

<400> SEQUENCE: 30
cttcctcctc ctttggatct ctg                                                   23

<210> SEQ ID NO 31
<211> LENGTH: 20
<212> TYPE: DNA
<213> ORGANISM: Artificial Sequence
<220> FEATURE:
<223> OTHER INFORMATION: PRIMER

<400> SEQUENCE: 31
tctgctgctc tgggttccag                                                       20

<210> SEQ ID NO 32
<211> LENGTH: 23
<212> TYPE: DNA
<213> ORGANISM: Artificial Sequence
<220> FEATURE:
<223> OTHER INFORMATION: PRIMER

<400> SEQUENCE: 32
gacatccagw tgacccagtc tcc                                                   23

<210> SEQ ID NO 33
<211> LENGTH: 28
<212> TYPE: DNA
<213> ORGANISM: Artificial Sequence
<220> FEATURE:
<223> OTHER INFORMATION: PRIMER

<400> SEQUENCE: 33
gatattgtga tgacccagac tccactct                                              28

<210> SEQ ID NO 34
<211> LENGTH: 28
<212> TYPE: DNA
<213> ORGANISM: Artificial Sequence
<220> FEATURE:
<223> OTHER INFORMATION: PRIMER

<400> SEQUENCE: 34
gatattgtga tgactcagtc tccactct                                              28

<210> SEQ ID NO 35
<211> LENGTH: 25
<212> TYPE: DNA
<213> ORGANISM: Artificial Sequence
<220> FEATURE:
<223> OTHER INFORMATION: PRIMER

<400> SEQUENCE: 35
gaaattgtgt tgacrcagtc tccag                                                 25

<210> SEQ ID NO 36
<211> LENGTH: 25
<212> TYPE: DNA
<213> ORGANISM: Artificial Sequence
```

```
<220> FEATURE:
<223> OTHER INFORMATION: PRIMER

<400> SEQUENCE: 36
gaaatagtga tgacgcagtc tccag                                           25

<210> SEQ ID NO 37
<211> LENGTH: 22
<212> TYPE: DNA
<213> ORGANISM: Artificial Sequence
<220> FEATURE:
<223> OTHER INFORMATION: PRIMER

<400> SEQUENCE: 37
gacatcgtga tgacccagtc tc                                              22

<210> SEQ ID NO 38
<211> LENGTH: 22
<212> TYPE: DNA
<213> ORGANISM: Artificial Sequence
<220> FEATURE:
<223> OTHER INFORMATION: PRIMER

<400> SEQUENCE: 38
gaaacgacac tcacgcagtc tc                                              22

<210> SEQ ID NO 39
<211> LENGTH: 24
<212> TYPE: DNA
<213> ORGANISM: Artificial Sequence
<220> FEATURE:
<223> OTHER INFORMATION: PRIMER

<400> SEQUENCE: 39
gaaattgtgc tgactcagtc tcca                                            24

<210> SEQ ID NO 40
<211> LENGTH: 20
<212> TYPE: DNA
<213> ORGANISM: Artificial Sequence
<220> FEATURE:
<223> OTHER INFORMATION: PRIMER

<400> SEQUENCE: 40
ggtcctgggc ccagtctgtg                                                 20

<210> SEQ ID NO 41
<211> LENGTH: 20
<212> TYPE: DNA
<213> ORGANISM: Artificial Sequence
<220> FEATURE:
<223> OTHER INFORMATION: PRIMER

<400> SEQUENCE: 41
ggtcctgggc ycagtctgcc                                                 20

<210> SEQ ID NO 42
<211> LENGTH: 22
<212> TYPE: DNA
<213> ORGANISM: Artificial Sequence
<220> FEATURE:
<223> OTHER INFORMATION: PRIMER

<400> SEQUENCE: 42
gctctgwggc ctcctatgag ct                                              22
```

```
<210> SEQ ID NO 43
<211> LENGTH: 23
<212> TYPE: DNA
<213> ORGANISM: Artificial Sequence
<220> FEATURE:
<223> OTHER INFORMATION: PRIMER

<400> SEQUENCE: 43
gctctgtgac ctcctatgwg ctg                                           23

<210> SEQ ID NO 44
<211> LENGTH: 26
<212> TYPE: DNA
<213> ORGANISM: Artificial Sequence
<220> FEATURE:
<223> OTHER INFORMATION: PRIMER

<400> SEQUENCE: 44
gttctgtggt ttcttctgag ctgact                                        26

<210> SEQ ID NO 45
<211> LENGTH: 21
<212> TYPE: DNA
<213> ORGANISM: Artificial Sequence
<220> FEATURE:
<223> OTHER INFORMATION: PRIMER

<400> SEQUENCE: 45
ggtctctctc ccwgcytgtg c                                             21

<210> SEQ ID NO 46
<211> LENGTH: 20
<212> TYPE: DNA
<213> ORGANISM: Artificial Sequence
<220> FEATURE:
<223> OTHER INFORMATION: PRIMER

<400> SEQUENCE: 46
gttccctctc gcaggctgtg                                               20

<210> SEQ ID NO 47
<211> LENGTH: 20
<212> TYPE: DNA
<213> ORGANISM: Artificial Sequence
<220> FEATURE:
<223> OTHER INFORMATION: PRIMER

<400> SEQUENCE: 47
gktccctctc ccagcctgtg                                               20

<210> SEQ ID NO 48
<211> LENGTH: 23
<212> TYPE: DNA
<213> ORGANISM: Artificial Sequence
<220> FEATURE:
<223> OTHER INFORMATION: PRIMER

<400> SEQUENCE: 48
gttcttgggc caattttatg ctg                                           23

<210> SEQ ID NO 49
<211> LENGTH: 23
<212> TYPE: DNA
<213> ORGANISM: Artificial Sequence
<220> FEATURE:
<223> OTHER INFORMATION: PRIMER
```

```
<400> SEQUENCE: 49
ggtccaattc ycagrctgtg gtg                                           23

<210> SEQ ID NO 50
<211> LENGTH: 24
<212> TYPE: DNA
<213> ORGANISM: Artificial Sequence
<220> FEATURE:
<223> OTHER INFORMATION: PRIMER

<400> SEQUENCE: 50
gagtggattc tcagactgtg gtga                                          24

<210> SEQ ID NO 51
<211> LENGTH: 20
<212> TYPE: DNA
<213> ORGANISM: Artificial Sequence
<220> FEATURE:
<223> OTHER INFORMATION: PRIMER

<400> SEQUENCE: 51
tgtcagtggt ccaggcaggg                                               20

<210> SEQ ID NO 52
<211> LENGTH: 20
<212> TYPE: DNA
<213> ORGANISM: Artificial Sequence
<220> FEATURE:
<223> OTHER INFORMATION: PRIMER

<400> SEQUENCE: 52
cagtctgtgy tgacgcagcc                                               20

<210> SEQ ID NO 53
<211> LENGTH: 21
<212> TYPE: DNA
<213> ORGANISM: Artificial Sequence
<220> FEATURE:
<223> OTHER INFORMATION: PRIMER

<400> SEQUENCE: 53
cagtctgtgc tgactcagcc a                                             21

<210> SEQ ID NO 54
<211> LENGTH: 20
<212> TYPE: DNA
<213> ORGANISM: Artificial Sequence
<220> FEATURE:
<223> OTHER INFORMATION: PRIMER

<400> SEQUENCE: 54
cagtctgccc tgactcagcc                                               20

<210> SEQ ID NO 55
<211> LENGTH: 21
<212> TYPE: DNA
<213> ORGANISM: Artificial Sequence
<220> FEATURE:
<223> OTHER INFORMATION: PRIMER

<400> SEQUENCE: 55
tcctatgagc tgacwcagcc a                                             21

<210> SEQ ID NO 56
```

<210> SEQ ID NO 56
<211> LENGTH: 22
<212> TYPE: DNA
<213> ORGANISM: Artificial Sequence
<220> FEATURE:
<223> OTHER INFORMATION: PRIMER

<400> SEQUENCE: 56
tcttctgagc tgactcagga cc                                         22

<210> SEQ ID NO 57
<211> LENGTH: 20
<212> TYPE: DNA
<213> ORGANISM: Artificial Sequence
<220> FEATURE:
<223> OTHER INFORMATION: PRIMER

<400> SEQUENCE: 57
cagsctgtgc tgactcagcc                                            20

<210> SEQ ID NO 58
<211> LENGTH: 22
<212> TYPE: DNA
<213> ORGANISM: Artificial Sequence
<220> FEATURE:
<223> OTHER INFORMATION: PRIMER

<400> SEQUENCE: 58
cagcctgtgc tgactcaatc at                                         22

<210> SEQ ID NO 59
<211> LENGTH: 21
<212> TYPE: DNA
<213> ORGANISM: Artificial Sequence
<220> FEATURE:
<223> OTHER INFORMATION: PRIMER

<400> SEQUENCE: 59
cagcttgtgc tgactcaatc g                                          21

<210> SEQ ID NO 60
<211> LENGTH: 24
<212> TYPE: DNA
<213> ORGANISM: Artificial Sequence
<220> FEATURE:
<223> OTHER INFORMATION: PRIMER

<400> SEQUENCE: 60
aattttatgc tgactcagcc ccac                                       24

<210> SEQ ID NO 61
<211> LENGTH: 22
<212> TYPE: DNA
<213> ORGANISM: Artificial Sequence
<220> FEATURE:
<223> OTHER INFORMATION: PRIMER

<400> SEQUENCE: 61
cagrctgtgg tgacycagga gc                                         22

<210> SEQ ID NO 62
<211> LENGTH: 20
<212> TYPE: DNA
<213> ORGANISM: Artificial Sequence
<220> FEATURE:
<223> OTHER INFORMATION: PRIMER

<400> SEQUENCE: 62
caggcagggc tgactcagcc                                               20

<210> SEQ ID NO 63
<211> LENGTH: 20
<212> TYPE: DNA
<213> ORGANISM: Artificial Sequence
<220> FEATURE:
<223> OTHER INFORMATION: PRIMER

<400> SEQUENCE: 63
aggtgtgcac gccgctggtc                                               20

<210> SEQ ID NO 64
<211> LENGTH: 23
<212> TYPE: DNA
<213> ORGANISM: Artificial Sequence
<220> FEATURE:
<223> OTHER INFORMATION: PRIMER

<400> SEQUENCE: 64
ggttcgggga agtagtcctt gac                                           23

<210> SEQ ID NO 65
<211> LENGTH: 24
<212> TYPE: DNA
<213> ORGANISM: Artificial Sequence
<220> FEATURE:
<223> OTHER INFORMATION: PRIMER

<400> SEQUENCE: 65
gtttctcgta gtctgctttg ctca                                          24

<210> SEQ ID NO 66
<211> LENGTH: 22
<212> TYPE: DNA
<213> ORGANISM: Artificial Sequence
<220> FEATURE:
<223> OTHER INFORMATION: PRIMER

<400> SEQUENCE: 66
gtgctgtcct tgctgtcctg ct                                            22

<210> SEQ ID NO 67
<211> LENGTH: 23
<212> TYPE: DNA
<213> ORGANISM: Artificial Sequence
<220> FEATURE:
<223> OTHER INFORMATION: PRIMER

<400> SEQUENCE: 67
ttggagggtk tggtggtctc cac                                           23

<210> SEQ ID NO 68
<211> LENGTH: 20
<212> TYPE: DNA
<213> ORGANISM: Artificial Sequence
<220> FEATURE:
<223> OTHER INFORMATION: PRIMER

<400> SEQUENCE: 68
ttgacggggc tgcyatctgc                                               20

<210> SEQ ID NO 69
<211> LENGTH: 21
<212> TYPE: DNA

<213> ORGANISM: Artificial Sequence
<220> FEATURE:
<223> OTHER INFORMATION: PRIMER

<400> SEQUENCE: 69
cacrgctccc gggtagaagt c                                                21

<210> SEQ ID NO 70
<211> LENGTH: 41
<212> TYPE: DNA
<213> ORGANISM: Artificial Sequence
<220> FEATURE:
<223> OTHER INFORMATION: PRIMER

<400> SEQUENCE: 70
gttgctacgc gtgtcctgag csaggtgcag ctggtgsagt c                            41

<210> SEQ ID NO 71
<211> LENGTH: 41
<212> TYPE: DNA
<213> ORGANISM: Artificial Sequence
<220> FEATURE:
<223> OTHER INFORMATION: PRIMER

<400> SEQUENCE: 71
gttgctacgc gtgtcctgag ccaggtccag cttgtgcagt c                            41

<210> SEQ ID NO 72
<211> LENGTH: 41
<212> TYPE: DNA
<213> ORGANISM: Artificial Sequence
<220> FEATURE:
<223> OTHER INFORMATION: PRIMER

<400> SEQUENCE: 72
gttgctacgc gtgtcctgag ccaggttcag ctggtgcagt c                            41

<210> SEQ ID NO 73
<211> LENGTH: 43
<212> TYPE: DNA
<213> ORGANISM: Artificial Sequence
<220> FEATURE:
<223> OTHER INFORMATION: PRIMER

<400> SEQUENCE: 73
gttgctacgc gtgtcctgag ccaggtccag ctggtacagt ctg                          43

<210> SEQ ID NO 74
<211> LENGTH: 43
<212> TYPE: DNA
<213> ORGANISM: Artificial Sequence
<220> FEATURE:
<223> OTHER INFORMATION: PRIMER

<400> SEQUENCE: 74
gttgctacgc gtgtcctgag ccaggtcacc ttgarggagt ctg                          43

<210> SEQ ID NO 75
<211> LENGTH: 42
<212> TYPE: DNA
<213> ORGANISM: Artificial Sequence
<220> FEATURE:
<223> OTHER INFORMATION: PRIMER

<400> SEQUENCE: 75
gttgctacgc gtgtcctgag cgaggtgcag ctgttggagt ct                           42

<210> SEQ ID NO 76
<211> LENGTH: 40
<212> TYPE: DNA
<213> ORGANISM: Artificial Sequence
<220> FEATURE:
<223> OTHER INFORMATION: PRIMER

<400> SEQUENCE: 76
gttgctacgc gtgtcctgag ccagstgcag ctgcaggagt                                40

<210> SEQ ID NO 77
<211> LENGTH: 42
<212> TYPE: DNA
<213> ORGANISM: Artificial Sequence
<220> FEATURE:
<223> OTHER INFORMATION: PRIMER

<400> SEQUENCE: 77
gttgctacgc gtgtcctgag ccaggtgcag ctacarcagt gg                            42

<210> SEQ ID NO 78
<211> LENGTH: 42
<212> TYPE: DNA
<213> ORGANISM: Artificial Sequence
<220> FEATURE:
<223> OTHER INFORMATION: PRIMER

<400> SEQUENCE: 78
gttgctacgc gtgtcctgag ccaggtacag ctgcagcagt ca                            42

<210> SEQ ID NO 79
<211> LENGTH: 40
<212> TYPE: DNA
<213> ORGANISM: Artificial Sequence
<220> FEATURE:
<223> OTHER INFORMATION: PRIMER

<400> SEQUENCE: 79
gttgctacgc gtgtcctgag ccaggtgcag ctggtgcaat                               40

<210> SEQ ID NO 80
<211> LENGTH: 39
<212> TYPE: DNA
<213> ORGANISM: Artificial Sequence
<220> FEATURE:
<223> OTHER INFORMATION: PRIMER

<400> SEQUENCE: 80
gatgggccct tggtgctagc tgaggagacg gtgaccagg                                39

<210> SEQ ID NO 81
<211> LENGTH: 41
<212> TYPE: DNA
<213> ORGANISM: Artificial Sequence
<220> FEATURE:
<223> OTHER INFORMATION: PRIMER

<400> SEQUENCE: 81
gatgggccct tggtgctagc tgaggagaca gtgaccaggg t                             41

<210> SEQ ID NO 82
<211> LENGTH: 42
<212> TYPE: DNA
<213> ORGANISM: Artificial Sequence
<220> FEATURE:

<223> OTHER INFORMATION: PRIMER

<400> SEQUENCE: 82
gatgggccct tggtgctagc tgaagagacg gtgaccattg tc     42

<210> SEQ ID NO 83
<211> LENGTH: 39
<212> TYPE: DNA
<213> ORGANISM: Artificial Sequence
<220> FEATURE:
<223> OTHER INFORMATION: PRIMER

<400> SEQUENCE: 83
gatgggccct tggtgctagc tgaggagacg gtgaccgtg     39

<210> SEQ ID NO 84
<211> LENGTH: 43
<212> TYPE: DNA
<213> ORGANISM: Artificial Sequence
<220> FEATURE:
<223> OTHER INFORMATION: PRIMER

<400> SEQUENCE: 84
ggctcccagg tgcacgatgt gacatccagw tgacccagtc tcc     43

<210> SEQ ID NO 85
<211> LENGTH: 48
<212> TYPE: DNA
<213> ORGANISM: Artificial Sequence
<220> FEATURE:
<223> OTHER INFORMATION: PRIMER

<400> SEQUENCE: 85
ggctcccagg tgcacgatgt gatattgtga tgacccagac tccactct     48

<210> SEQ ID NO 86
<211> LENGTH: 45
<212> TYPE: DNA
<213> ORGANISM: Artificial Sequence
<220> FEATURE:
<223> OTHER INFORMATION: PRIMER

<400> SEQUENCE: 86
ggctcccagg tgcacgatgt gaaattgtgt tgacrcagtc tccag     45

<210> SEQ ID NO 87
<211> LENGTH: 42
<212> TYPE: DNA
<213> ORGANISM: Artificial Sequence
<220> FEATURE:
<223> OTHER INFORMATION: PRIMER

<400> SEQUENCE: 87
ggctcccagg tgcacgatgt gacatcgtga tgacccagtc tc     42

<210> SEQ ID NO 88
<211> LENGTH: 42
<212> TYPE: DNA
<213> ORGANISM: Artificial Sequence
<220> FEATURE:
<223> OTHER INFORMATION: PRIMER

<400> SEQUENCE: 88
ggctcccagg tgcacgatgt gaaacgacac tcacgcagtc tc     42

<210> SEQ ID NO 89
<211> LENGTH: 44
<212> TYPE: DNA
<213> ORGANISM: Artificial Sequence
<220> FEATURE:
<223> OTHER INFORMATION: PRIMER

<400> SEQUENCE: 89
ggctcccagg tgcacgatgt gaaattgtgc tgactcagtc tcca                     44

<210> SEQ ID NO 90
<211> LENGTH: 37
<212> TYPE: DNA
<213> ORGANISM: Artificial Sequence
<220> FEATURE:
<223> OTHER INFORMATION: PRIMER

<400> SEQUENCE: 90
tgcagccacc gtacgtttga tttccacctt ggtccct                             37

<210> SEQ ID NO 91
<211> LENGTH: 37
<212> TYPE: DNA
<213> ORGANISM: Artificial Sequence
<220> FEATURE:
<223> OTHER INFORMATION: PRIMER

<400> SEQUENCE: 91
tgcagccacc gtacgtttga tctccagctt ggtccct                             37

<210> SEQ ID NO 92
<211> LENGTH: 37
<212> TYPE: DNA
<213> ORGANISM: Artificial Sequence
<220> FEATURE:
<223> OTHER INFORMATION: PRIMER

<400> SEQUENCE: 92
tgcagccacc gtacgtttga tatccacttt ggtccca                             37

<210> SEQ ID NO 93
<211> LENGTH: 37
<212> TYPE: DNA
<213> ORGANISM: Artificial Sequence
<220> FEATURE:
<223> OTHER INFORMATION: PRIMER

<400> SEQUENCE: 93
tgcagccacc gtacgtttga tctccacctt ggtccct                             37

<210> SEQ ID NO 94
<211> LENGTH: 38
<212> TYPE: DNA
<213> ORGANISM: Artificial Sequence
<220> FEATURE:
<223> OTHER INFORMATION: PRIMER

<400> SEQUENCE: 94
tgcagccacc gtacgtttaa tctccagtcg tgtccctt                            38

<210> SEQ ID NO 95
<211> LENGTH: 49
<212> TYPE: DNA
<213> ORGANISM: Artificial Sequence
<220> FEATURE:
<223> OTHER INFORMATION: PRIMER

<400> SEQUENCE: 95
tccttgctta tgggtccgga gtggattctc agtctgtgyt gacgcagcc    49

<210> SEQ ID NO 96
<211> LENGTH: 50
<212> TYPE: DNA
<213> ORGANISM: Artificial Sequence
<220> FEATURE:
<223> OTHER INFORMATION: PRIMER

<400> SEQUENCE: 96
tccttgctta tgggtccgga gtggattctc agtctgtgct gactcagcca    50

<210> SEQ ID NO 97
<211> LENGTH: 49
<212> TYPE: DNA
<213> ORGANISM: Artificial Sequence
<220> FEATURE:
<223> OTHER INFORMATION: PRIMER

<400> SEQUENCE: 97
tccttgctta tgggtccgga gtggattctc agtctgccct gactcagcc    49

<210> SEQ ID NO 98
<211> LENGTH: 50
<212> TYPE: DNA
<213> ORGANISM: Artificial Sequence
<220> FEATURE:
<223> OTHER INFORMATION: PRIMER

<400> SEQUENCE: 98
tccttgctta tgggtccgga gtggattctt cctatgagct gacwcagcca    50

<210> SEQ ID NO 99
<211> LENGTH: 50
<212> TYPE: DNA
<213> ORGANISM: Artificial Sequence
<220> FEATURE:
<223> OTHER INFORMATION: PRIMER

<400> SEQUENCE: 99
tccttgctta tgggtccgga gtggattctt cttctgagct gactcaggac    50

<210> SEQ ID NO 100
<211> LENGTH: 49
<212> TYPE: DNA
<213> ORGANISM: Artificial Sequence
<220> FEATURE:
<223> OTHER INFORMATION: PRIMER

<400> SEQUENCE: 100
tccttgctta tgggtccgga gtggattctc agsctgtgct gactcagcc    49

<210> SEQ ID NO 101
<211> LENGTH: 49
<212> TYPE: DNA
<213> ORGANISM: Artificial Sequence
<220> FEATURE:
<223> OTHER INFORMATION: PRIMER

<400> SEQUENCE: 101
tccttgctta tgggtccgga gtggattctc agyctgtgct gactcaatc    49

<210> SEQ ID NO 102
<211> LENGTH: 50

<212> TYPE: DNA
<213> ORGANISM: Artificial Sequence
<220> FEATURE:
<223> OTHER INFORMATION: PRIMER

<400> SEQUENCE: 102
tccttgctta tgggtccgga gtggattcta attttatgct gactcagccc          50

<210> SEQ ID NO 103
<211> LENGTH: 50
<212> TYPE: DNA
<213> ORGANISM: Artificial Sequence
<220> FEATURE:
<223> OTHER INFORMATION: PRIMER

<400> SEQUENCE: 103
tccttgctta tgggtccgga gtggattctc agrctgtggt gacycaggag          50

<210> SEQ ID NO 104
<211> LENGTH: 49
<212> TYPE: DNA
<213> ORGANISM: Artificial Sequence
<220> FEATURE:
<223> OTHER INFORMATION: PRIMER

<400> SEQUENCE: 104
tccttgctta tgggtccgga gtggattctc aggcagggct gactcagcc           49

<210> SEQ ID NO 105
<211> LENGTH: 35
<212> TYPE: DNA
<213> ORGANISM: Artificial Sequence
<220> FEATURE:
<223> OTHER INFORMATION: PRIMER

<400> SEQUENCE: 105
ggccttgggc tgacctagga cggtgacctt ggtcc                          35

<210> SEQ ID NO 106
<211> LENGTH: 35
<212> TYPE: DNA
<213> ORGANISM: Artificial Sequence
<220> FEATURE:
<223> OTHER INFORMATION: PRIMER

<400> SEQUENCE: 106
ggccttgggc tgacctagga cggtcagctt ggtcc                          35

<210> SEQ ID NO 107
<211> LENGTH: 35
<212> TYPE: DNA
<213> ORGANISM: Artificial Sequence
<220> FEATURE:
<223> OTHER INFORMATION: PRIMER

<400> SEQUENCE: 107
ggccttgggc tgacctagga cggtcacctt ggtgc                          35

<210> SEQ ID NO 108
<211> LENGTH: 35
<212> TYPE: DNA
<213> ORGANISM: Artificial Sequence
<220> FEATURE:
<223> OTHER INFORMATION: PRIMER

<400> SEQUENCE: 108
ggccttgggc tgacctagga cggtcagctg ggtgc    35

<210> SEQ ID NO 109
<211> LENGTH: 124
<212> TYPE: PRT
<213> ORGANISM: Homo sapiens

<400> SEQUENCE: 109

Glu Val Gln Leu Val Glu Ser Gly Gly Gly Leu Val Lys Pro Gly Asp
1               5                   10                  15

Ser Leu Thr Val Ser Cys Val Ala Ser Gly Phe Thr Phe Ser Asn Tyr
            20                  25                  30

Phe Ile His Trp Val Arg Gln Ala Pro Gly Lys Gly Leu Glu Trp Val
        35                  40                  45

Ala Thr Ile Ser Gly Arg Thr Lys Tyr Met Phe Tyr Ser Asp Ser Leu
    50                  55                  60

Arg Gly Arg Phe Thr Val Ser Arg Asp Asn Ala Asn Asn Ser Val Tyr
65                  70                  75                  80

Leu His Met Ser Ser Leu Arg Gly Glu Asp Thr Ala Leu Tyr Tyr Cys
                85                  90                  95

Val Arg Gly Tyr Asp His Ser Asp Ser Asn Ser Ala Ala Asp Leu Leu
            100                 105                 110

His Trp Gly Arg Gly Thr Leu Val Thr Val Ser Ser
        115                 120

<210> SEQ ID NO 110
<211> LENGTH: 124
<212> TYPE: PRT
<213> ORGANISM: Homo sapiens

<400> SEQUENCE: 110

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Arg Tyr
            20                  25                  30

Ser Met His Trp Val Arg Gln Ala Pro Gly Lys Gly Leu Glu Trp Val
        35                  40                  45

Ser Ser Met Thr Ser Arg Thr Asn His Lys Tyr Tyr Ala Asp Ser Leu
    50                  55                  60

Lys Gly Arg Phe Leu Ile Ser Arg Asp Asn Arg Asp Ser Leu Tyr
65                  70                  75                  80

Leu Glu Met Asn Ser Leu Gly Val Glu Asp Thr Ala Ile Tyr Phe Cys
                85                  90                  95

Ala Arg Gly Tyr Asp Thr Ser Gly Ser Asp Ser Gly Val Asp Phe Gln
            100                 105                 110

Tyr Trp Gly Gln Gly Thr Leu Val Thr Val Ser Ser
        115                 120

<210> SEQ ID NO 111
<211> LENGTH: 121
<212> TYPE: PRT
<213> ORGANISM: Homo sapiens

<400> SEQUENCE: 111

Glu Val Gln Leu Leu Glu Ser Gly Gly Gly Leu Val Gln Pro Gly Gly
1               5                   10                  15

Pro Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Ser Ile Ser Gly Ser Gly Asp Asn Thr Tyr Tyr Ala Asp Ser Val
    50                  55                  60

Lys Gly Arg Phe Thr Ile Thr Arg Asp Ser Ser Lys Asn Thr Leu Tyr
65                  70                  75                  80

Leu Gln Met Asn Thr Leu Arg Ala Glu Asp Thr Ala Val Tyr Phe Cys
                85                  90                  95

Ala Lys Ser Gly Arg Asn Ile Ile Ser Pro Gly Phe Asp Ser Trp Gly
            100                 105                 110

Gln Gly Thr Leu Val Thr Val Ser Ser
            115                 120

<210> SEQ ID NO 112
<211> LENGTH: 122
<212> TYPE: PRT
<213> ORGANISM: Homo sapiens

<400> SEQUENCE: 112

Glu Val Gln Leu Val Glu Ser Gly Gly Gly Leu Val Lys Pro Gly Glu
1               5                   10                  15

Ser Leu Arg Leu Ala Cys Val Ala Ser Gly Phe Asn Phe Ser Asp Tyr
            20                  25                  30

Tyr Met Thr Trp Ile Arg Gln Ala Pro Gly Lys Gly Leu Glu Trp Val
        35                  40                  45

Ser Tyr Ile Ser Asn Ser Gly Ser His Thr Tyr Tyr Ala Asp Ala Val
    50                  55                  60

Lys Gly Arg Phe Thr Val Ser Arg Asp Asn Ala Lys Asn Ser Leu Tyr
65                  70                  75                  80

Leu Gln Met Thr Ser Leu Arg Gly Glu Asp Thr Ala Ile Tyr Phe Cys
                85                  90                  95

Ala Arg Asp Pro Ser Ile Met Arg Gly Thr Tyr Tyr Met Asp Val Trp
            100                 105                 110

Gly Lys Gly Thr Thr Val Thr Val Ser Ser
            115                 120

<210> SEQ ID NO 113
<211> LENGTH: 111
<212> TYPE: PRT
<213> ORGANISM: Homo sapiens

<400> SEQUENCE: 113

Asn Phe Met Leu Thr Gln Pro Leu Ser Val Ser Gly Tyr Pro Gly Lys
1               5                   10                  15

Thr Ile Val Ile Ser Cys Val Arg Ser Ser Gly Ser Val Ala Ser His
            20                  25                  30

Tyr Val Gln Trp Phe Gln Gln Arg Pro Gly Ser Ala Pro Ala Met Val
        35                  40                  45

Ile Tyr Glu Asp Ser His Arg Pro Gly Ile Pro Asp Arg Phe Ser
    50                  55                  60

Gly Ser Val Asp Ala Ser Ser Asn Ser Ala Ser Leu Thr Ile Ser Gly
65                  70                  75                  80

Leu Lys Thr Glu Asp Glu Ala Asp Tyr Phe Cys Gln Ser Tyr Tyr Gly
                85                  90                  95

Asn Asn Gln Val Leu Phe Gly Gly Gly Thr Lys Leu Thr Val Leu
            100                 105                 110

<210> SEQ ID NO 114
<211> LENGTH: 111
<212> TYPE: PRT
<213> ORGANISM: Homo sapiens

<400> SEQUENCE: 114

Asn Phe Met Leu Thr Gln Pro His Ser Val Ser Glu Ser Pro Gly Lys
1               5                   10                  15

Thr Ile Thr Ile Ser Cys Thr Arg Gly Arg Gly Tyr Ile Ala Ser Tyr
            20                  25                  30

Tyr Val Gln Trp Tyr Gln Gln Arg Pro Gly Gly Val Pro Lys Ile Val
        35                  40                  45

Val Phe Glu Asp Thr Gln Arg Pro Ser Gly Val Pro Asp Arg Ile Ser
    50                  55                  60

Gly Ser Ile Asp Thr Ser Thr Asn Ser Ala Ser Leu Thr Ile Ser Gly
65                  70                  75                  80

Leu Gln Thr Glu Asp Glu Ala Asp Tyr Tyr Cys Gln Ser Tyr Asp Asp
                85                  90                  95

Ala Asn His Val Ile Phe Gly Gly Gly Thr Lys Leu Thr Val Leu
            100                 105                 110

<210> SEQ ID NO 115
<211> LENGTH: 116
<212> TYPE: PRT
<213> ORGANISM: Homo sapiens

<400> SEQUENCE: 115

Gln Pro Val Leu Thr Gln Pro Pro Ser Ala Ser Ala Ser Leu Gly Ala
1               5                   10                  15

Ser Val Thr Leu Thr Cys Thr Leu Asn Ser Asp Tyr Gly Asp Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Phe Leu Thr Ile
65                  70                  75                  80

Lys Asn Ile Gln Glu Glu Asp Glu Ser Asp Tyr Tyr Cys Gly Ala Asp
                85                  90                  95

His Gly Ser Ala Asn Asn Phe Ile Trp Val Phe Gly Gly Gly Thr Lys
            100                 105                 110

Leu Thr Val Leu
        115

<210> SEQ ID NO 116
<211> LENGTH: 110
<212> TYPE: PRT
<213> ORGANISM: Homo sapiens

<400> SEQUENCE: 116

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Thr Asn
            20                  25                  30

Pro Val Ser Trp Tyr Gln Gln Phe Pro Gly Met Ala Pro Lys Leu Leu
        35                  40                  45

Ile Tyr Phe Asn Asn Gln Arg Pro Ser Gly Val Pro Glu Arg Phe Ser
             50                  55                  60

Gly Ser Lys Ser Gly Thr Pro Ala Ser Leu Ala Ile Gly Gly Leu Gln
 65                  70                  75                  80

Ser Glu Asp Glu Ala Asn Tyr Tyr Cys Ala Ser Trp Asp Asp Thr Leu
                 85                  90                  95

Asn Gly Leu Val Phe Gly Gly Gly Thr Lys Leu Thr Val Leu
                100                 105                 110

<210> SEQ ID NO 117
<211> LENGTH: 20
<212> TYPE: DNA
<213> ORGANISM: Artificial Sequence
<220> FEATURE:
<223> OTHER INFORMATION: PRIMER

<400> SEQUENCE: 117
gctcccaggt gcacgatgtg                                              20

<210> SEQ ID NO 118
<211> LENGTH: 24
<212> TYPE: DNA
<213> ORGANISM: Artificial Sequence
<220> FEATURE:
<223> OTHER INFORMATION: PRIMER

<400> SEQUENCE: 118
gcttatgggt ccggagtgga ttct                                         24

<210> SEQ ID NO 119
<211> LENGTH: 20
<212> TYPE: DNA
<213> ORGANISM: Artificial Sequence
<220> FEATURE:
<223> OTHER INFORMATION: PRIMER

<400> SEQUENCE: 119
gatgggccct tggtgctagc                                              20

<210> SEQ ID NO 120
<211> LENGTH: 8
<212> TYPE: PRT
<213> ORGANISM: Homo sapiens

<400> SEQUENCE: 120

Gly Phe Thr Phe Ser Asn Tyr Phe
 1               5

<210> SEQ ID NO 121
<211> LENGTH: 8
<212> TYPE: PRT
<213> ORGANISM: Homo sapiens

<400> SEQUENCE: 121

Ile Ser Gly Arg Thr Lys Tyr Met
 1               5

<210> SEQ ID NO 122
<211> LENGTH: 17
<212> TYPE: PRT
<213> ORGANISM: Homo sapiens

<400> SEQUENCE: 122

Val Arg Gly Tyr Asp His Ser Asp Ser Asn Ser Ala Ala Asp Leu Leu

His

<210> SEQ ID NO 123
<211> LENGTH: 8
<212> TYPE: PRT
<213> ORGANISM: Homo sapiens

<400> SEQUENCE: 123

Gly Phe Pro Phe Ser Arg Tyr Ser
1               5

<210> SEQ ID NO 124
<211> LENGTH: 8
<212> TYPE: PRT
<213> ORGANISM: Homo sapiens

<400> SEQUENCE: 124

Met Thr Ser Arg Thr Asn His Lys
1               5

<210> SEQ ID NO 125
<211> LENGTH: 17
<212> TYPE: PRT
<213> ORGANISM: Homo sapiens

<400> SEQUENCE: 125

Ala Arg Gly Tyr Asp Thr Ser Gly Ser Asp Ser Gly Val Asp Phe Gln
1               5                   10                  15

Tyr

<210> SEQ ID NO 126
<211> LENGTH: 8
<212> TYPE: PRT
<213> ORGANISM: Homo sapiens

<400> SEQUENCE: 126

Gly Phe Thr Phe Ser Ile Tyr Ser
1               5

<210> SEQ ID NO 127
<211> LENGTH: 8
<212> TYPE: PRT
<213> ORGANISM: Homo sapiens

<400> SEQUENCE: 127

Ile Ser Gly Ser Gly Asp Asn Thr
1               5

<210> SEQ ID NO 128
<211> LENGTH: 14
<212> TYPE: PRT
<213> ORGANISM: Homo sapiens

<400> SEQUENCE: 128

Ala Lys Ser Gly Arg Asn Ile Ile Ser Pro Gly Phe Asp Ser
1               5                   10

<210> SEQ ID NO 129
<211> LENGTH: 8
<212> TYPE: PRT
<213> ORGANISM: Homo sapiens

<400> SEQUENCE: 129

```
Gly Phe Asn Phe Ser Asp Tyr Tyr
1               5
```

<210> SEQ ID NO 130
<211> LENGTH: 8
<212> TYPE: PRT
<213> ORGANISM: Homo sapiens

<400> SEQUENCE: 130

```
Ile Ser Asn Ser Gly Ser His Thr
1               5
```

<210> SEQ ID NO 131
<211> LENGTH: 15
<212> TYPE: PRT
<213> ORGANISM: Homo sapiens

<400> SEQUENCE: 131

```
Ala Arg Asp Pro Ser Ile Met Arg Gly Thr Tyr Tyr Met Asp Val
1               5                   10                  15
```

<210> SEQ ID NO 132
<211> LENGTH: 8
<212> TYPE: PRT
<213> ORGANISM: Homo sapiens

<400> SEQUENCE: 132

```
Ser Gly Ser Val Ala Ser His Tyr
1               5
```

<210> SEQ ID NO 133
<211> LENGTH: 3
<212> TYPE: PRT
<213> ORGANISM: Homo sapiens

<400> SEQUENCE: 133

```
Glu Asp Ser
1
```

<210> SEQ ID NO 134
<211> LENGTH: 10
<212> TYPE: PRT
<213> ORGANISM: Homo sapiens

<400> SEQUENCE: 134

```
Gln Ser Tyr Tyr Gly Asn Asn Gln Val Leu
1               5                   10
```

<210> SEQ ID NO 135
<211> LENGTH: 8
<212> TYPE: PRT
<213> ORGANISM: Homo sapiens

<400> SEQUENCE: 135

```
Arg Gly Tyr Ile Ala Ser Tyr Tyr
1               5
```

<210> SEQ ID NO 136
<211> LENGTH: 3
<212> TYPE: PRT
<213> ORGANISM: Homo sapiens

<400> SEQUENCE: 136

```
Glu Asp Thr
```

```
<210> SEQ ID NO 137
<211> LENGTH: 10
<212> TYPE: PRT
<213> ORGANISM: Homo sapiens

<400> SEQUENCE: 137

Gln Ser Tyr Asp Asp Ala Asn His Val Ile
1               5                   10

<210> SEQ ID NO 138
<211> LENGTH: 7
<212> TYPE: PRT
<213> ORGANISM: Homo sapiens

<400> SEQUENCE: 138

Ser Asp Tyr Gly Asp Tyr Lys
1               5

<210> SEQ ID NO 139
<211> LENGTH: 8
<212> TYPE: PRT
<213> ORGANISM: Homo sapiens

<400> SEQUENCE: 139

Val Gly Thr Gly Gly Ile Val Gly
1               5

<210> SEQ ID NO 140
<211> LENGTH: 13
<212> TYPE: PRT
<213> ORGANISM: Homo sapiens

<400> SEQUENCE: 140

Gly Ala Asp His Gly Ser Ala Asn Asn Phe Ile Trp Val
1               5                   10

<210> SEQ ID NO 141
<211> LENGTH: 8
<212> TYPE: PRT
<213> ORGANISM: Homo sapiens

<400> SEQUENCE: 141

Ser Ser Asn Ile Gly Thr Asn Pro
1               5

<210> SEQ ID NO 142
<211> LENGTH: 3
<212> TYPE: PRT
<213> ORGANISM: Homo sapiens

<400> SEQUENCE: 142

Phe Asn Asn
1

<210> SEQ ID NO 143
<211> LENGTH: 11
<212> TYPE: PRT
<213> ORGANISM: Homo sapiens

<400> SEQUENCE: 143

Ala Ser Trp Asp Asp Thr Leu Asn Gly Leu Val
1               5                   10
```

```
<210> SEQ ID NO 144
<211> LENGTH: 10
<212> TYPE: PRT
<213> ORGANISM: Homo sapiens

<400> SEQUENCE: 144

Gly Phe Thr Phe Ser Asn Tyr Phe Ile His
1               5                   10

<210> SEQ ID NO 145
<211> LENGTH: 17
<212> TYPE: PRT
<213> ORGANISM: Homo sapiens

<400> SEQUENCE: 145

Thr Ile Ser Gly Arg Thr Lys Tyr Met Phe Tyr Ser Asp Ser Leu Arg
1               5                   10                  15

Gly

<210> SEQ ID NO 146
<211> LENGTH: 15
<212> TYPE: PRT
<213> ORGANISM: Homo sapiens

<400> SEQUENCE: 146

Gly Tyr Asp His Ser Asp Ser Asn Ser Ala Ala Asp Leu Leu His
1               5                   10                  15

<210> SEQ ID NO 147
<211> LENGTH: 10
<212> TYPE: PRT
<213> ORGANISM: Homo sapiens

<400> SEQUENCE: 147

Gly Phe Pro Phe Ser Arg Tyr Ser Met His
1               5                   10

<210> SEQ ID NO 148
<211> LENGTH: 17
<212> TYPE: PRT
<213> ORGANISM: Homo sapiens

<400> SEQUENCE: 148

Ser Met Thr Ser Arg Thr Asn His Lys Tyr Tyr Ala Asp Ser Leu Lys
1               5                   10                  15

Gly

<210> SEQ ID NO 149
<211> LENGTH: 15
<212> TYPE: PRT
<213> ORGANISM: Homo sapiens

<400> SEQUENCE: 149

Gly Tyr Asp Thr Ser Gly Ser Asp Ser Gly Val Asp Phe Gln Tyr
1               5                   10                  15

<210> SEQ ID NO 150
<211> LENGTH: 10
<212> TYPE: PRT
<213> ORGANISM: Homo sapiens

<400> SEQUENCE: 150

Gly Phe Thr Phe Ser Ile Tyr Ser Met Asn
```

```
1               5                   10
```

<210> SEQ ID NO 151
<211> LENGTH: 17
<212> TYPE: PRT
<213> ORGANISM: Homo sapiens

<400> SEQUENCE: 151

```
Ser Ile Ser Gly Ser Gly Asp Asn Thr Tyr Tyr Ala Asp Ser Val Lys
1               5                   10                  15

Gly
```

<210> SEQ ID NO 152
<211> LENGTH: 11
<212> TYPE: PRT
<213> ORGANISM: Homo sapiens

<400> SEQUENCE: 152

```
Ser Gly Arg Asn Ile Ser Pro Gly Phe Asp Ser
1               5                   10
```

<210> SEQ ID NO 153
<211> LENGTH: 10
<212> TYPE: PRT
<213> ORGANISM: Homo sapiens

<400> SEQUENCE: 153

```
Gly Phe Asn Phe Ser Asp Tyr Tyr Met Thr
1               5                   10
```

<210> SEQ ID NO 154
<211> LENGTH: 17
<212> TYPE: PRT
<213> ORGANISM: Homo sapiens

<400> SEQUENCE: 154

```
Tyr Ile Ser Asn Ser Gly Ser His Thr Tyr Tyr Ala Asp Ala Val Lys
1               5                   10                  15

Gly
```

<210> SEQ ID NO 155
<211> LENGTH: 13
<212> TYPE: PRT
<213> ORGANISM: Homo sapiens

<400> SEQUENCE: 155

```
Asp Pro Ser Ile Met Arg Gly Thr Tyr Tyr Met Asp Val
1               5                   10
```

<210> SEQ ID NO 156
<211> LENGTH: 13
<212> TYPE: PRT
<213> ORGANISM: Homo sapiens

<400> SEQUENCE: 156

```
Val Arg Ser Ser Gly Ser Val Ala Ser His Tyr Val Gln
1               5                   10
```

<210> SEQ ID NO 157
<211> LENGTH: 7
<212> TYPE: PRT
<213> ORGANISM: Homo sapiens

<400> SEQUENCE: 157

Glu Asp Ser His Arg Pro Ser
1               5

<210> SEQ ID NO 158
<211> LENGTH: 13
<212> TYPE: PRT
<213> ORGANISM: Homo sapiens

<400> SEQUENCE: 158

Thr Arg Gly Arg Gly Tyr Ile Ala Ser Tyr Tyr Val Gln
1               5                   10

<210> SEQ ID NO 159
<211> LENGTH: 7
<212> TYPE: PRT
<213> ORGANISM: Homo sapiens

<400> SEQUENCE: 159

Glu Asp Thr Gln Arg Pro Ser
1               5

<210> SEQ ID NO 160
<211> LENGTH: 12
<212> TYPE: PRT
<213> ORGANISM: Homo sapiens

<400> SEQUENCE: 160

Thr Leu Asn Ser Asp Tyr Gly Asp Tyr Lys Val Asp
1               5                   10

<210> SEQ ID NO 161
<211> LENGTH: 7
<212> TYPE: PRT
<213> ORGANISM: Homo sapiens

<400> SEQUENCE: 161

Val Gly Thr Gly Gly Ile Val
1               5

<210> SEQ ID NO 162
<211> LENGTH: 13
<212> TYPE: PRT
<213> ORGANISM: Homo sapiens

<400> SEQUENCE: 162

Ser Gly Ser Ser Ser Asn Ile Gly Thr Asn Pro Val Ser
1               5                   10

<210> SEQ ID NO 163
<211> LENGTH: 7
<212> TYPE: PRT
<213> ORGANISM: Homo sapiens

<400> SEQUENCE: 163

Phe Asn Asn Gln Arg Pro Ser
1               5

<210> SEQ ID NO 164
<211> LENGTH: 124
<212> TYPE: PRT
<213> ORGANISM: Artificial Sequence
<220> FEATURE:
<223> OTHER INFORMATION: Recombinant variant antibody sequence

<400> SEQUENCE: 164

Glu Val Gln Leu Val Glu Ser Gly Gly Gly Leu Val Lys Pro Gly Asp
1               5                   10                  15

Ser Leu Thr Val Ser Cys Val Ala Ser Gly Phe Thr Phe Ser Asn Tyr
            20                  25                  30

Phe Ile His Trp Val Arg Gln Ala Pro Gly Lys Gly Leu Glu Trp Val
            35                  40                  45

Ala Thr Ile Ser Gly Arg Thr Lys Tyr Met Phe Tyr Ser Asp Ser Leu
    50                  55                  60

Arg Gly Arg Phe Thr Val Ser Arg Asp Asn Ala Ala Asn Ser Val Tyr
65                  70                  75                  80

Leu His Met Ser Ser Leu Arg Gly Glu Asp Thr Ala Leu Tyr Tyr Cys
                85                  90                  95

Val Arg Gly Tyr Asp His Ser Asp Ser Asn Ser Ala Ala Asp Leu Leu
                100                 105                 110

His Trp Gly Arg Gly Thr Leu Val Thr Val Ser Ser
            115                 120

<210> SEQ ID NO 165
<211> LENGTH: 124
<212> TYPE: PRT
<213> ORGANISM: Artificial Sequence
<220> FEATURE:
<223> OTHER INFORMATION: Recombinant variant antibody sequence

<400> SEQUENCE: 165

Glu Val Gln Leu Val Glu Ser Gly Gly Gly Leu Val Lys Pro Gly Asp
1               5                   10                  15

Ser Leu Thr Val Ser Cys Val Ala Ser Gly Phe Thr Phe Ser Asn Tyr
            20                  25                  30

Phe Ile His Trp Val Arg Gln Ala Pro Gly Lys Gly Leu Glu Trp Val
            35                  40                  45

Ala Thr Ile Ser Gly Arg Thr Lys Tyr Met Phe Tyr Ser Asp Ser Leu
    50                  55                  60

Arg Gly Arg Phe Thr Val Ser Arg Asp Asn Ala Gln Asn Ser Val Tyr
65                  70                  75                  80

Leu His Met Ser Ser Leu Arg Gly Glu Asp Thr Ala Leu Tyr Tyr Cys
                85                  90                  95

Val Arg Gly Tyr Asp His Ser Asp Ser Asn Ser Ala Ala Asp Leu Leu
                100                 105                 110

His Trp Gly Arg Gly Thr Leu Val Thr Val Ser Ser
            115                 120

<210> SEQ ID NO 166
<211> LENGTH: 143
<212> TYPE: PRT
<213> ORGANISM: Homo sapiens

<400> SEQUENCE: 166

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Arg Asp Asp Phe Glu Lys Leu Thr
            85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140

<210> SEQ ID NO 167
<211> LENGTH: 23
<212> TYPE: PRT
<213> ORGANISM: Homo sapiens

<400> SEQUENCE: 167

Leu Gly Ile Leu Lys Asn Trp Lys Glu Glu Ser Asp Arg Lys Ile Met
1               5                   10                  15

Gln Ser Gln Ile Val Ser Phe
            20

<210> SEQ ID NO 168
<211> LENGTH: 15
<212> TYPE: PRT
<213> ORGANISM: Homo sapiens

<400> SEQUENCE: 168

Asn Val Lys Phe Phe Asn Ser Asn Lys Lys Arg Asp Asp Phe
1               5                   10                  15

<210> SEQ ID NO 169
<211> LENGTH: 41
<212> TYPE: DNA
<213> ORGANISM: Artificial Sequence
<220> FEATURE:
<223> OTHER INFORMATION: PRIMER

<400> SEQUENCE: 169
cgtttctaga gacaacgccc agaattcggt atatctccac a                41

<210> SEQ ID NO 170
<211> LENGTH: 40
<212> TYPE: DNA
<213> ORGANISM: Artificial Sequence
<220> FEATURE:
<223> OTHER INFORMATION: PRIMER

<400> SEQUENCE: 170
cgtttctaga gacaacgccg ccaattcggt atatctccac                  40

<210> SEQ ID NO 171
<211> LENGTH: 13
<212> TYPE: PRT
<213> ORGANISM: Homo sapiens

<400> SEQUENCE: 171

Trp Lys Glu Glu Ser Asp Arg Lys Ile Met Gln Ser Gln
1               5                   10

<210> SEQ ID NO 172
<211> LENGTH: 11
<212> TYPE: PRT

<213> ORGANISM: Homo sapiens

<400> SEQUENCE: 172

Phe Asn Ser Asn Lys Lys Lys Arg Asp Asp Phe
1               5                   10

<210> SEQ ID NO 173
<211> LENGTH: 373
<212> TYPE: DNA
<213> ORGANISM: Homo sapiens

<400> SEQUENCE: 173

| gaggtgcagc | tggtggagtc | tgggggaggc | ctggtcaagc | cggggactc | tctgacagtc | 60 |
| tcctgtgtcg | cctctggatt | cactttcagc | aactatttca | tccactgggt | ccgacaggct | 120 |
| ccagggaagg | gactggagtg | ggtcgcaacg | atcagtggcc | gtacgaaata | tatgttctac | 180 |
| tcagactcat | tgaggggccg | attcaccgtt | tctagagaca | acgccaacaa | ttcggtatat | 240 |
| ctccacatga | gcagcctgag | aggcgaagac | acggctctct | attactgtgt | gagaggctat | 300 |
| gatcatagtg | attccaactc | ggcagcagac | ctcctgcatt | ggggccgggg | caccctggtc | 360 |
| accgtctcct | cag | | | | | 373 |

<210> SEQ ID NO 174
<211> LENGTH: 334
<212> TYPE: DNA
<213> ORGANISM: Homo sapiens

<400> SEQUENCE: 174

| aattttatgc | tgactcagcc | cctctctgtg | tcgggctatc | cgggaaagac | gatagtcatc | 60 |
| tcctgtgtcc | ggagcagtgg | cagcgtggcc | agccactatg | tgcagtggtt | ccaacagcgc | 120 |
| ccgggcagtg | cccccgccat | ggtgatttat | gaagatagcc | acagaccttc | tgggattcct | 180 |
| gatcgattct | ctggctccgt | cgacgcctcc | tccaactctg | cctccctcac | catctctgga | 240 |
| ctgaagactg | aggacgaggc | tgactacttc | tgtcaatctt | attatggcaa | caatcaggtt | 300 |
| ctcttcggcg | gcgggaccaa | gctgaccgtc | ctag | | | 334 |

<210> SEQ ID NO 175
<211> LENGTH: 373
<212> TYPE: DNA
<213> ORGANISM: Artificial Sequence
<220> FEATURE:
<223> OTHER INFORMATION: ANTIBODY

<400> SEQUENCE: 175

| gaggtgcagc | tggtggagtc | tgggggaggc | ctggtcaagc | cggggactc | tctgacagtc | 60 |
| tcctgtgtcg | cctctggatt | cactttcagc | aactatttca | tccactgggt | ccgacaggct | 120 |
| ccagggaagg | gactggagtg | ggtcgcaacg | atcagtggcc | gtacgaaata | tatgttctac | 180 |
| tcagactcat | tgaggggccg | attcaccgtt | tctagagaca | acgccagaa | ttcggtatat | 240 |
| ctccacatga | gcagcctgag | aggcgaagac | acggctctct | attactgtgt | gagaggctat | 300 |
| gatcatagtg | attccaactc | ggcagcagac | ctcctgcatt | ggggccgggg | caccctggtc | 360 |
| accgtctcct | cag | | | | | 373 |

<210> SEQ ID NO 176
<211> LENGTH: 373
<212> TYPE: DNA
<213> ORGANISM: Artificial Sequence
<220> FEATURE:

<223> OTHER INFORMATION: ANTIBODY

<400> SEQUENCE: 176

| gaggtgcagc tggtggagtc tgggggaggc ctggtcaagc cggggggactc tctgacagtc | 60 |
| tcctgtgtcg cctctggatt cactttcagc aactatttca tccactgggt ccgacaggct | 120 |
| ccagggaagg gactggagtg ggtcgcaacg atcagtggcc gtacgaaata tatgttctac | 180 |
| tcagactcat tgaggggccg attcaccgtt tctagagaca acgccgccaa ttcggtatat | 240 |
| ctccacatga gcagcctgag aggcgaagac acggctctct attactgtgt gagaggctat | 300 |
| gatcatagtg attccaactc ggcagcagac ctcctgcatt ggggccgggg caccctggtc | 360 |
| accgtctcct cag | 373 |

<210> SEQ ID NO 177
<211> LENGTH: 373
<212> TYPE: DNA
<213> ORGANISM: Homo sapiens

<400> SEQUENCE: 177

| gaggtgcagc tggtggagtc tgggggaggc ctggtcaagc cgggggggtc cctgagactc | 60 |
| tcctgtgcag cctctggctt ccccttcagt cgctattcaa tgcactgggt ccgccaggct | 120 |
| ccagggaagg ggctggagtg ggtctcatcg atgacgtctc ggactaacca caaatactac | 180 |
| gcagactcac tgaagggccg attcctcatc tctcgagaca acgacaggga ctcactgtac | 240 |
| ctggaaatga acagcctggg agtcgaggac acggcgatat atttctgtgc aagaggctat | 300 |
| gatactagtg gttccgactc gggagtagac ttccaatact ggggccaggg caccctggtc | 360 |
| accgtctcct cag | 373 |

<210> SEQ ID NO 178
<211> LENGTH: 334
<212> TYPE: DNA
<213> ORGANISM: Homo sapiens

<400> SEQUENCE: 178

| aattttatgc tgactcagcc ccactctgtg tcggagtctc cggggaagac gataaccatc | 60 |
| tcctgcaccc gcggcagagg atacattgcc agctactatg tccagtggta ccaacagcgc | 120 |
| ccgggcggtg tccccaaaat tgtggtcttt gaggatactc agagaccctc tggggtccct | 180 |
| gatcgaatct ctggctccat cgacacctcc accaactctg cctccctcac catctctgga | 240 |
| ctgcagactg aagacgaggc tgactactac tgtcagtctt atgatgatgc caatcatgtg | 300 |
| atcttcggcg gagggaccaa gctgaccgtc ctag | 334 |

<210> SEQ ID NO 179
<211> LENGTH: 364
<212> TYPE: DNA
<213> ORGANISM: Homo sapiens

<400> SEQUENCE: 179

| gaggtgcagc tgttggagtc tgggggaggc ctggtacagc cggggggggcc cctgagactc | 60 |
| tcctgtgcag cctctggatt cacctttagc atctacagta tgaactgggt ccgccaggct | 120 |
| ccagggaagg ggctggagtg ggtctcaagt attagtggga gtggcgataa tacatactat | 180 |
| gcagactccg tgaagggccg gttcaccatc accagagaca gttccaagaa cacactgtat | 240 |
| ctgcaaatga acaccctcag agccgaggac acggccgtat atttttgtgc gaaatctgga | 300 |
| agaaatatta tatccctgg atttgactcc tggggccagg gaaccctggt caccgtctcc | 360 |

```
tcag                                                                  364

<210> SEQ ID NO 180
<211> LENGTH: 349
<212> TYPE: DNA
<213> ORGANISM: Homo sapiens

<400> SEQUENCE: 180
cagcctgtgc tgactcagcc accttctgca tcagcctccc tgggagcctc ggtcacactc      60
acgtgcaccc tgaacagcga ctatggtgat tataaagtgg actggtacca gcagagacca     120
gggaagggcc cccgatttgt gatgcgagtg ggcactggtg ggattgtggg atccaagggg     180
gacggcatcc ctgatcgctt ctcagtcttg gggtcaggcc tgaatcggtt cctgaccatt     240
aagaacatcc aggaagagga tgagagtgac tactactgtg gggcagacca tggcagtgcg     300
aacaacttca tttgggtgtt cggcggaggg accaagctga ccgtcctag                349

<210> SEQ ID NO 181
<211> LENGTH: 366
<212> TYPE: DNA
<213> ORGANISM: Homo sapiens

<400> SEQUENCE: 181
gaggtgcagc tggtggagtc tgggggaggc ttggtcaagc ctggagagtc cctgagactc      60
gcctgtgtag cctctggctt caacttcagt gactactaca tgacgtggat ccgccaggct     120
ccagggaagg ggctggagtg ggtttcatat attagtaata gtggtagtca cacatactac     180
gcagacgctg tgaagggccg cttcaccgtc tccagggaca atgccaagaa ctcactgtat     240
ctgcaaatga ccagcctgag aggcgaggac acggccatat atttctgtgc gagagatcct     300
tctatcatgc ggggaaccta ctacatggac gtctggggca aagggaccac ggtcaccgtc     360
tcctca                                                               366

<210> SEQ ID NO 182
<211> LENGTH: 331
<212> TYPE: DNA
<213> ORGANISM: Homo sapiens

<400> SEQUENCE: 182
cagtctgtgc tgactcagcc accctcagcg tctggaaccc ccggccagag ggtcaccatc      60
tcttgttccg gaagcagctc aacatcgga actaaccctg tcagttggta ccagcagttc     120
cccggaatgg cccccaagct cctcatctat tttaacaatc agcggccctc aggggtccct     180
gaacgattct ctggctccaa gtctggcacc ccagcctccc tggccatcgg tggactccag     240
tctgaggatg aggctaacta ttattgtgca tcctgggatg acaccctgaa tggtctggtg     300
ttcggcggag ggaccaagct gaccgtccta g                                   331

<210> SEQ ID NO 183
<211> LENGTH: 454
<212> TYPE: PRT
<213> ORGANISM: Homo sapiens

<400> SEQUENCE: 183

Glu Val Gln Leu Val Glu Ser Gly Gly Gly Leu Val Lys Pro Gly Asp
1               5                   10                  15

Ser Leu Thr Val Ser Cys Val Ala Ser Gly Phe Thr Phe Ser Asn Tyr
            20                  25                  30
```

```
Phe Ile His Trp Val Arg Gln Ala Pro Gly Lys Gly Leu Glu Trp Val
         35                  40                  45
Ala Thr Ile Ser Gly Arg Thr Lys Tyr Met Phe Tyr Ser Asp Ser Leu
 50                  55                  60
Arg Gly Arg Phe Thr Val Ser Arg Asp Asn Ala Asn Asn Ser Val Tyr
 65                  70                  75                  80
Leu His Met Ser Ser Leu Arg Gly Glu Asp Thr Ala Leu Tyr Tyr Cys
                 85                  90                  95
Val Arg Gly Tyr Asp His Ser Asp Ser Asn Ser Ala Ala Asp Leu Leu
                100                 105                 110
His Trp Gly Arg Gly Thr Leu Val Thr Val Ser Ser Ala Ser Thr Lys
             115                 120                 125
Gly Pro Ser Val Phe Pro Leu Ala Pro Ser Ser Lys Ser Thr Ser Gly
 130                 135                 140
Gly Thr Ala Ala Leu Gly Cys Leu Val Lys Asp Tyr Phe Pro Glu Pro
 145                 150                 155                 160
Val Thr Val Ser Trp Asn Ser Gly Ala Leu Thr Ser Gly Val His Thr
                 165                 170                 175
Phe Pro Ala Val Leu Gln Ser Ser Gly Leu Tyr Ser Leu Ser Ser Val
             180                 185                 190
Val Thr Val Pro Ser Ser Ser Leu Gly Thr Gln Thr Tyr Ile Cys Asn
         195                 200                 205
Val Asn His Lys Pro Ser Asn Thr Lys Val Asp Lys Val Glu Pro
     210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                 245                 250                 255
Thr Leu Met Ile Ser Arg Thr Pro Glu Val Thr Cys Val Val Val Asp
             260                 265                 270
Val Ser His Glu Asp Pro Glu Val Lys Phe Asn Trp Tyr Val Asp Gly
         275                 280                 285
Val Glu Val His Asn Ala Lys Thr Lys Pro Arg Glu Glu Gln Tyr Asn
     290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                 325                 330                 335
Ala Pro Ile Glu Lys Thr Ile Ser Lys Ala Lys Gly Gln Pro Arg Glu
             340                 345                 350
Pro Gln Val Tyr Thr Leu Pro Pro Ser Arg Glu Glu Met Thr Lys Asn
         355                 360                 365
Gln Val Ser Leu Thr Cys Leu Val Lys Gly Phe Tyr Pro Ser Asp Ile
     370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                 405                 410                 415
Leu Thr Val Asp Lys Ser Arg Trp Gln Gln Gly Asn Val Phe Ser Cys
             420                 425                 430
Ser Val Met His Glu Ala Leu His Asn His Tyr Thr Gln Lys Ser Leu
         435                 440                 445
Ser Leu Ser Pro Gly Lys
```

<210> SEQ ID NO 184
<211> LENGTH: 217
<212> TYPE: PRT
<213> ORGANISM: Homo sapiens

<400> SEQUENCE: 184

Asn Phe Met Leu Thr Gln Pro Leu Ser Val Ser Gly Tyr Pro Gly Lys
1               5                   10                  15

Thr Ile Val Ile Ser Cys Val Arg Ser Ser Gly Ser Val Ala Ser His
            20                  25                  30

Tyr Val Gln Trp Phe Gln Arg Pro Gly Ser Ala Pro Ala Met Val
        35                  40                  45

Ile Tyr Glu Asp Ser His Arg Pro Ser Gly Ile Pro Asp Arg Phe Ser
    50                  55                  60

Gly Ser Val Asp Ala Ser Ser Asn Ser Ala Ser Leu Thr Ile Ser Gly
65                  70                  75                  80

Leu Lys Thr Glu Asp Glu Ala Asp Tyr Phe Cys Gln Ser Tyr Tyr Gly
                85                  90                  95

Asn Asn Gln Val Leu Phe Gly Gly Gly Thr Lys Leu Thr Val Leu Gly
            100                 105                 110

Gln Pro Lys Ala Asn Pro Thr Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 185
<211> LENGTH: 454
<212> TYPE: PRT
<213> ORGANISM: Homo sapiens

<400> SEQUENCE: 185

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Arg Tyr
            20                  25                  30

Ser Met His Trp Val Arg Gln Ala Pro Gly Lys Gly Leu Glu Trp Val
        35                  40                  45

Ser Ser Met Thr Ser Arg Thr Asn His Lys Tyr Tyr Ala Asp Ser Leu
    50                  55                  60

Lys Gly Arg Phe Leu Ile Ser Arg Asp Asn Asp Arg Asp Ser Leu Tyr
65                  70                  75                  80

Leu Glu Met Asn Ser Leu Gly Val Glu Asp Thr Ala Ile Tyr Phe Cys
                85                  90                  95

Ala Arg Gly Tyr Asp Thr Ser Gly Ser Asp Ser Gly Val Asp Phe Gln

```
                100             105             110
Tyr Trp Gly Gln Gly Thr Leu Val Thr Val Ser Ser Ala Ser Thr Lys
            115             120             125

Gly Pro Ser Val Phe Pro Leu Ala Pro Ser Ser Lys Ser Thr Ser Gly
            130             135             140

Gly Thr Ala Ala Leu Gly Cys Leu Val Lys Asp Tyr Phe Pro Glu Pro
145             150             155             160

Val Thr Val Ser Trp Asn Ser Gly Ala Leu Thr Ser Gly Val His Thr
            165             170             175

Phe Pro Ala Val Leu Gln Ser Ser Gly Leu Tyr Ser Leu Ser Ser Val
            180             185             190

Val Thr Val Pro Ser Ser Ser Leu Gly Thr Gln Thr Tyr Ile Cys Asn
            195             200             205

Val Asn His Lys Pro Ser Asn Thr Lys Val Asp Lys Lys Val Glu Pro
            210             215             220

Lys Ser Cys Asp Lys Thr His Thr Cys Pro Pro Cys Pro Ala Pro Glu
225             230             235             240

Leu Leu Gly Gly Pro Ser Val Phe Leu Phe Pro Pro Lys Pro Lys Asp
            245             250             255

Thr Leu Met Ile Ser Arg Thr Pro Glu Val Thr Cys Val Val Val Asp
            260             265             270

Val Ser His Glu Asp Pro Glu Val Lys Phe Asn Trp Tyr Val Asp Gly
            275             280             285

Val Glu Val His Asn Ala Lys Thr Lys Pro Arg Glu Glu Gln Tyr Asn
            290             295             300

Ser Thr Tyr Arg Val Val Ser Val Leu Thr Val Leu His Gln Asp Trp
305             310             315             320

Leu Asn Gly Lys Glu Tyr Lys Cys Lys Val Ser Asn Lys Ala Leu Pro
            325             330             335

Ala Pro Ile Glu Lys Thr Ile Ser Lys Ala Lys Gly Gln Pro Arg Glu
            340             345             350

Pro Gln Val Tyr Thr Leu Pro Pro Ser Arg Glu Glu Met Thr Lys Asn
            355             360             365

Gln Val Ser Leu Thr Cys Leu Val Lys Gly Phe Tyr Pro Ser Asp Ile
            370             375             380

Ala Val Glu Trp Glu Ser Asn Gly Gln Pro Glu Asn Asn Tyr Lys Thr
385             390             395             400

Thr Pro Pro Val Leu Asp Ser Asp Gly Ser Phe Phe Leu Tyr Ser Lys
            405             410             415

Leu Thr Val Asp Lys Ser Arg Trp Gln Gln Gly Asn Val Phe Ser Cys
            420             425             430

Ser Val Met His Glu Ala Leu His Asn His Tyr Thr Gln Lys Ser Leu
            435             440             445

Ser Leu Ser Pro Gly Lys
        450

<210> SEQ ID NO 186
<211> LENGTH: 217
<212> TYPE: PRT
<213> ORGANISM: Homo sapiens

<400> SEQUENCE: 186

Asn Phe Met Leu Thr Gln Pro His Ser Val Ser Glu Ser Pro Gly Lys
1               5               10              15
```

Thr Ile Thr Ile Ser Cys Thr Arg Gly Arg Gly Tyr Ile Ala Ser Tyr
            20                  25                  30

Tyr Val Gln Trp Tyr Gln Gln Arg Pro Gly Gly Val Pro Lys Ile Val
            35                  40                  45

Val Phe Glu Asp Thr Gln Arg Pro Ser Gly Val Pro Asp Arg Ile Ser
50                  55                  60

Gly Ser Ile Asp Thr Ser Thr Asn Ser Ala Ser Leu Thr Ile Ser Gly
65                  70                  75                  80

Leu Gln Thr Glu Asp Glu Ala Asp Tyr Tyr Cys Gln Ser Tyr Asp Asp
                85                  90                  95

Ala Asn His Val Ile Phe Gly Gly Thr Lys Leu Thr Val Leu Gly
            100                 105                 110

Gln Pro Lys Ala Asn Pro Thr Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Gly Ser Pro Val
145                 150                 155                 160

Lys Ala Gly Val Glu Thr Thr Lys Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
210                 215

<210> SEQ ID NO 187
<211> LENGTH: 454
<212> TYPE: PRT
<213> ORGANISM: Artificial Sequence
<220> FEATURE:
<223> OTHER INFORMATION: Recombinant antibody variant

<400> SEQUENCE: 187

Glu Val Gln Leu Val Glu Ser Gly Gly Gly Leu Val Lys Pro Gly Asp
1               5                   10                  15

Ser Leu Thr Val Ser Cys Val Ala Ser Gly Phe Thr Phe Ser Asn Tyr
            20                  25                  30

Phe Ile His Trp Val Arg Gln Ala Pro Gly Lys Gly Leu Glu Trp Val
            35                  40                  45

Ala Thr Ile Ser Gly Arg Thr Lys Tyr Met Phe Tyr Ser Asp Ser Leu
50                  55                  60

Arg Gly Arg Phe Thr Val Ser Arg Asp Asn Ala Ala Asn Ser Val Tyr
65                  70                  75                  80

Leu His Met Ser Ser Leu Arg Gly Glu Asp Thr Ala Leu Tyr Tyr Cys
                85                  90                  95

Val Arg Gly Tyr Asp His Ser Asp Ser Asn Ser Ala Ala Asp Leu Leu
            100                 105                 110

His Trp Gly Arg Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 188
<211> LENGTH: 454
<212> TYPE: PRT
<213> ORGANISM: Artificial Sequence
<220> FEATURE:
<223> OTHER INFORMATION: Recombinant antibody variant

<400> SEQUENCE: 188

Glu Val Gln Leu Val Glu Ser Gly Gly Gly Leu Val Lys Pro Gly Asp
1               5                   10                  15

Ser Leu Thr Val Ser Cys Val Ala Ser Gly Phe Thr Phe Ser Asn Tyr
            20                  25                  30

Phe Ile His Trp Val Arg Gln Ala Pro Gly Lys Gly Leu Glu Trp Val
            35                  40                  45

Ala Thr Ile Ser Gly Arg Thr Lys Tyr Met Phe Tyr Ser Asp Ser Leu
        50                  55                  60

```
Arg Gly Arg Phe Thr Val Ser Arg Asp Asn Ala Gln Asn Ser Val Tyr
 65              70                  75                  80

Leu His Met Ser Ser Leu Arg Gly Glu Asp Thr Ala Leu Tyr Tyr Cys
                 85                  90                  95

Val Arg Gly Tyr Asp His Ser Asp Ser Asn Ser Ala Ala Asp Leu Leu
                100                 105                 110

His Trp Gly Arg Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
                130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
                275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Glu Glu Met Thr Lys Asn
                355                 360                 365

Gln Val Ser Leu Thr Cys Leu Val Lys Gly Phe Tyr Pro Ser Asp Ile
                370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
                435                 440                 445

Ser Leu Ser Pro Gly Lys
                450
```

METHODS FOR TREATMENT OF HBV INFECTION

CROSS REFERENCE TO RELATED APPLICATIONS

This application is a continuation of International Application No. PCT/US2019/024663, filed Mar. 28, 2019, which claims priority of International Application No. PCT/CN2018/085836, filed May 7, 2018, and of U.S. Provisional Patent Application No. 62/650,195, filed Mar. 29, 2018, each of which is entirely incorporated herein by reference for all purposes.

FIELD

The present disclosure relates generally to methods for treating hepatitis B virus infection, particularly methods that use antibodies, that bind to human interferon-gamma (IFNγ).

REFERENCE TO SEQUENCE LISTING

The official copy of the Sequence Listing is submitted concurrently with the specification as an ASCII formatted text file via EFS-Web, with a file name of "09793-001WO1_SeqList_ST25.txt", a creation date of Mar. 28, 2019, and a size of 66,627 bytes. The Sequence Listing filed via EFS-Web is part of the specification and is incorporated in its entirety by reference herein.

BACKGROUND

Chronic hepatitis B virus (HBV) infection is a major cause of hepatocellular carcinoma (HCC) worldwide and its most important cause in Asia. Seventy-five percent of all chronic HBV infections occur in Asia and the prevalence in Taiwan is 15-20%, where more than 90% of the adult population has been infected with HBV in the past. See e.g., Chen et al., "Estimation of seroprevalence of hepatitis B virus and hepatitis C virus in Taiwan from a large-scale survey of free hepatitis screening participants," *J. Formos. Med. Assoc.* (2007) 106(2):148-55.

HBV-related HCC often occurs at the age of 40 or older, suggesting that HBV may persist in carriers for decades before HCC actually develops. The persistence of HBV may be caused by a systemic antigen-specific immune tolerance due to persistent exposure to a chronic HBV infection in liver. That is, the HBV-specific immune response is diminished during the persistence of the chronic infection, leading to extremely lowered or no response to the HBV vaccination. Thus, it is difficult to develop an effective strategy or a therapeutic agent to treat a chronic HBV infection, and there remains a need for methods of treatments of HBV infection.

Interferon gamma ("IFNγ") has been shown to inhibit HBV gene expression and replication in human cell culture. See e.g., Suri D et al., "Non-cytolytic inhibition of hepatitis B virus replication in human hepatocytes," *J Hepatol.* 2001 December; 35(6): 790-7. IFNγ has also been shown to inhibit HBV gene expression and replication in HBV transgenic mice. See e.g., Yang P L et al., "Immune effectors required for hepatitis B virus clearance," *Proc Natl Acad Sci. USA* 2010 Jan. 12; 107(2): 798-802. IFNγ has been proposed as a therapeutic for treating chronic HBV and has undergone a phase II clinical trial. See e.g., NCT00753467, "A Phase II Study to Determine the Safety and Efficacy of Interferon-gamma in Patients with Chronic Hepatitis B," at clinicaltrials.gov/ct2/show/NCT00753467.

SUMMARY

In contrast to the understanding in the art regarding IFNγ and HBV infection, the present disclosure provides methods and compositions for treatment based upon the surprising discovery that antibodies capable of blocking the activity IFNγ are useful in treating HBV infections, including chronic HBV infections. Without being bound by theory, it is proposed that sustained IFNγ signaling leads to immune checkpoint blockade, exhausted T cells and inhibition of effector T cells via various pathways, and thereby results in an immunosuppressive effect. In an HBV infected patient, it is proposed that prolonged IFNγ signaling leads to immune system suppression that prevents complete eradication of HBV using antiviral drug treatments. Accordingly, the present disclosure provides methods of treatment wherein the HBV infected patient is administered an IFNγ antibody, wherein the antibody neutralizes the effects of prolonged IFNγ signaling, and thus promotes restoration of normal immune function that can effectively eradicate the HBV infection from the patient.

In some embodiments, the present disclosure provides a method for treating hepatitis B virus infection, comprising administering to a subject in need thereof a composition comprising a therapeutically effective amount of an IFNγ antibody and a pharmaceutically acceptable carrier. In some embodiments, the IFNγ antibody modulates a biological function of IFNγ. In some embodiments, the IFNγ antibody neutralizes IFNγ.

In some embodiments of the method, the IFNγ antibody inhibits, decreases, and/or fully blocks the signaling activity of IFNγ; optionally, wherein the IFNγ antibody inhibits, decreases, and/or fully blocks IFNγ signaling activity by pro-human IFNγ, mature-human IFNγ, or truncated-human IFNγ.

In some embodiments of the method, the IFNγ antibody reduces one or more of: IFNγ-dependent cytokine production; IFNγ-dependent T cell dysfunction, IFNγ-dependent immune tolerance; and IFNγ-dependent inflammation.

In some embodiments of the method, wherein the IFNγ antibody reduces expression of HLA-DR and/or PDL1 in monocytes stimulated with IFNγ. In some embodiments, the IFNγ antibody reduces expression of indoleamine 2,3-dioxygenase (IDO) in monocytes stimulated with IFNγ.

In some embodiments of the method, the IFNγ antibody comprises:

a VH region having a CDR-H1 amino acid sequence selected from SEQ ID NO: 120 or 123, a CDR-H2 amino acid sequence selected from SEQ ID NO: 121 or 124, and a CDR-H3 amino acid sequence selected from SEQ ID NO: 122 or 125; and a VL region comprising a CDR-L1 amino acid sequence selected from SEQ ID NO: 132 or 135, a CDR-L2 amino acid sequence selected from SEQ ID NO: 133 or 136, and a CDR-L3 amino acid sequence selected from SEQ ID NO: 134 or 137.

In some embodiments of the method, the IFNγ antibody comprises:

(a) a VH region having a CDR-H1 amino acid sequence of SEQ ID NO: 120, a CDR-H2 amino acid sequence of SEQ ID NO: 121, and a CDR-H3 amino acid sequence of SEQ ID NO: 122, and a VL region comprising a CDR-L1 amino acid sequence of SEQ ID NO: 132, a CDR-L2 amino acid sequence of SEQ ID NO: 133, and a CDR-L3 amino acid sequence of SEQ ID NO: 134;

(b) a VH region having a CDR-H1 amino acid sequence of SEQ ID NO: 123, a CDR-H2 amino acid sequence of SEQ ID NO: 124, and a CDR-H3 amino acid sequence of SEQ ID NO: 125, and a VL region comprising a CDR-L1 amino acid sequence of SEQ ID NO: 135, a CDR-L2 amino acid sequence of SEQ ID NO: 136, and a CDR-L3 amino acid sequence of SEQ ID NO: 137; or (c) a VH region having a CDR-H1 amino acid sequence of SEQ ID NO: 123, a CDR-H2 amino acid sequence of SEQ ID NO: 124, and a CDR-H3 amino acid sequence of SEQ ID NO: 125, and a VL region comprising a CDR-L1 amino acid sequence of SEQ ID NO: 132, a CDR-L2 amino acid sequence of SEQ ID NO: 133, and a CDR-L3 amino acid sequence of SEQ ID NO: 134.

In some embodiments of the method, the IFNγ antibody comprises:

a VH region having a CDR-H1 amino acid sequence selected from SEQ ID NO: 120 or 123, a CDR-H2 amino acid sequence selected from SEQ ID NO: 121 or 124, and a CDR-H3 amino acid sequence selected from SEQ ID NO: 122 or 125; and a VL region comprising a CDR-L1 amino acid sequence selected from SEQ ID NO: 132 or 135, a CDR-L2 amino acid sequence selected from SEQ ID NO: 133 or 136, and a CDR-L3 amino acid sequence selected from SEQ ID NO: 134 or 137; and a VH region comprising an amino acid sequence having at least 90% identity to SEQ ID NO: 109, 110, 164, or 165; and a VL region comprising an amino acid sequence having at least 90% identity to SEQ ID NO: 113, or 114.

In some embodiments of the method, the IFNγ antibody comprises:

(a) a VH region amino acid sequence of SEQ ID NO: 109, and a VL region amino acid sequence of SEQ ID NO: 113;

(b) a VH region amino acid sequence of SEQ ID NO: 110, and a VL region amino acid sequence of SEQ ID NO: 114;

(c) a VH region amino acid sequence of SEQ ID NO: 109, and a VL region amino acid sequence of SEQ ID NO: 114;

(d) a VH region amino acid sequence of SEQ ID NO: 110, and a VL region amino acid sequence of SEQ ID NO: 113;

(e) a VH region amino acid sequence of SEQ ID NO: 164, and a VL region amino acid sequence of SEQ ID NO: 113; or (f) a VH region amino acid sequence of SEQ ID NO: 165, and a VL region amino acid sequence of SEQ ID NO: 113.

In some embodiments of the method, the IFNγ antibody comprises:

a VH region having a CDR-H1 amino acid sequence selected from SEQ ID NO: 120 or 123, a CDR-H2 amino acid sequence selected from SEQ ID NO: 121 or 124, and a CDR-H3 amino acid sequence selected from SEQ ID NO: 122 or 125; and a VL region comprising a CDR-L1 amino acid sequence selected from SEQ ID NO: 132 or 135, a CDR-L2 amino acid sequence selected from SEQ ID NO: 133 or 136, and a CDR-L3 amino acid sequence selected from SEQ ID NO: 134 or 137; and a heavy chain amino acid sequence having at least 90% identity to SEQ ID NO: 183, 185, 187, or 189; and a light chain amino acid sequence having at least 90% identity to SEQ ID NO: 184, or 186.

In some embodiments of the method, the IFNγ antibody comprises:

(a) a heavy chain amino acid sequence of SEQ ID NO: 183, and a light chain amino acid sequence of SEQ ID NO: 184;

(b) a heavy chain amino acid sequence of SEQ ID NO: 185, and a light chain amino acid sequence of SEQ ID NO: 186;

(c) a heavy chain amino acid sequence of SEQ ID NO: 183, and a light chain amino acid sequence of SEQ ID NO: 186;

(d) a heavy chain amino acid sequence of SEQ ID NO: 185, and a light chain amino acid sequence of SEQ ID NO: 184;

(e) a heavy chain amino acid sequence of SEQ ID NO: 187, and a light chain amino acid sequence of SEQ ID NO: 184; or (f) a heavy chain amino acid sequence of SEQ ID NO: 189, and a light chain amino acid sequence of SEQ ID NO: 184.

In some embodiments of the method, the VH region of the IFNγ antibody further comprises an amino acid substitution selected from N76A and N76Q.

In some embodiments of the method, the IFNγ antibody is an antibody selected from the group consisting of 2A6, 2B6, 2A6A, 2A6Q, AB, BA, AMG811, NI0105.

In some embodiments of the method, the IFNγ antibody is an immunoglobulin molecule, an Fv, a disulfide linked Fv, a monoclonal antibody, an scFv, a chimeric antibody, a single domain antibody, a CDR-grafted antibody, a diabody, a human antibody, a humanized antibody, a multispecific antibody, an Fab, a dual specific antibody, an Fab' fragment, a bispecific antibody, an F(ab')$_2$ fragment, a bivalent fragment comprising two Fab fragments linked by a disulfide bridge at the hinge region; a Fd fragment consisting of the V$_H$ and CH1 domains; a Fv fragment consisting of the V$_L$ and V$_H$ domains of a single arm of an antibody, a dAb fragment, an isolated complementarity determining region (CDR), or a single chain antibody.

In some embodiments of the method, the administering to the subject is by at least one mode selected from the group consisting of: parenteral, subcutaneous, intramuscular, intravenous, intra-articular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

In some embodiments of the method, the subject in need is an HBV carrier, one with chronic HBV infection, or one with HBV persistence.

In some embodiments the method can be carried out wherein the method further comprises administering at least one additional therapeutic agent. In some embodiments, the additional therapeutic agent is an HBV vaccine. In some embodiments, the additional therapeutic agent is an antibody that targets an inhibitory immune checkpoint molecule; optionally wherein the inhibitory immune checkpoint molecule is selected from PD1, PD-L1, and CTLA-4; or optionally wherein the antibody that targets an inhibitory immune checkpoint molecule is selected from an anti-PD1, anti-PD-L1, and an anti-CTLA-4.

In some embodiments the method can be carried out wherein the method further comprises administering at least one additional therapeutic agent, wherein the additional therapeutic agent is selected from the group consisting of: a therapeutic agent; an imaging agent; a cytotoxic agent; an angiogenesis inhibitor; a kinase inhibitor; a co-stimulation molecule blocker; an adhesion molecule blockers; an anti-cytokine antibody or functional fragment thereof; methotrexate; cyclosporin; rapamycin; FK506; a detectable label or reporter; a TNF antagonist; an anti-rheumatic; a muscle relaxant; a narcotic; a non-steroid anti-inflammatory drug (NSAID); an analgesic; an anesthetic; a sedative; a local anesthetic; a neuromuscular blocker; an antimicrobial; an antipsoriatic; a corticosteroid; an anabolic steroid; an erythropoietin; an immunization; an immunoglobulin; an immunosuppressive; a growth hormone; a hormone replacement drug; a radiopharmaceutical; an antidepressant; an antipsychotic; a stimulant; an asthma medication; a beta agonist; an inhaled steroid; an epinephrine or analog thereof; a cytokine; a cytokine antagonist; and an immunomodulatory agent.

In some embodiments, the method is carried out comprising administering a further therapeutic agent wherein the additional therapeutic agent is administered to the subject in need at the same time as the composition. In some embodiments, the additional therapeutic agent is administered to the subject in need before or after administration of the composition.

In some embodiments of the method, administering the therapeutically effective amount of the composition induces or boosts an immune response against HBV in the subject in need, and/or induces seroconversion with respect to HBV in the subject in need.

In some embodiments of the method, administering the therapeutically effective amount of the composition induces an immune response, wherein the immune response comprises production of antibodies or the production of cytokines that modulate the activity of the immune system.

In some embodiments of the method, after administering the therapeutically effective amount of the composition to the subject in need, HBsAg in the subject is reduced; optionally, wherein the subject exhibits durable HBsAg loss.

In some embodiments of the method, after administering the therapeutically effective amount of the composition the viral load of HBV in the subject is reduced; optionally, wherein the viral load of HBV in the subject is not detectable.

In some embodiments of the method, the IFNγ antibody binds to human IFNγ with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to human IFNγ. In some embodiments, the IFNγ antibody also binds to rhesus macaque/cynomolgus monkey IFNγ with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a cynomolgus IFNγ.

In some embodiments of the method, the IFNγ antibody increases IL-2 production from SEB-stimulated human PBMCs by at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, or at least 2.20-fold.

BRIEF DESCRIPTION OF THE FIGURES

FIG. 3A shows results for binding to human IFNγ; FIG. 3B shows results for binding to rhesus macaque/cynomolgus IFNγ.

FIG. 4 depicts assay results for IFNγ neutralizing activity of IFNγ antibodies in a luciferase reporter HeLa stable cell line.

FIG. 5A shows results for inhibition of production of CXCL9;
FIG. 5B shows results for inhibition of production of CXCL10.

FIG. 6A shows results for HLA-DR inhibition; FIG. 6B shows results for PD-L1 inhibition.

FIG. 9 depicts plots for two representative assays of IFNγ antibodies added to healthy donor cells in a one-way allogeneic MLR culture.

FIG. 10A shows results for enhancement of IL-2 secretion at Day 2; FIG. 10B shows results for enhancement of cell proliferation as measured at Day 7.

FIG. 12A shows results for PBMCs; FIG. 12B shows results for B cells.

FIG. 13A shows results for enhanced IL-2 production el the IFNγ blocking antibody, NI0501 with blocking antibodies of PD-1, PD-L1, or CTLA4.

DETAILED DESCRIPTION

Figure 1:
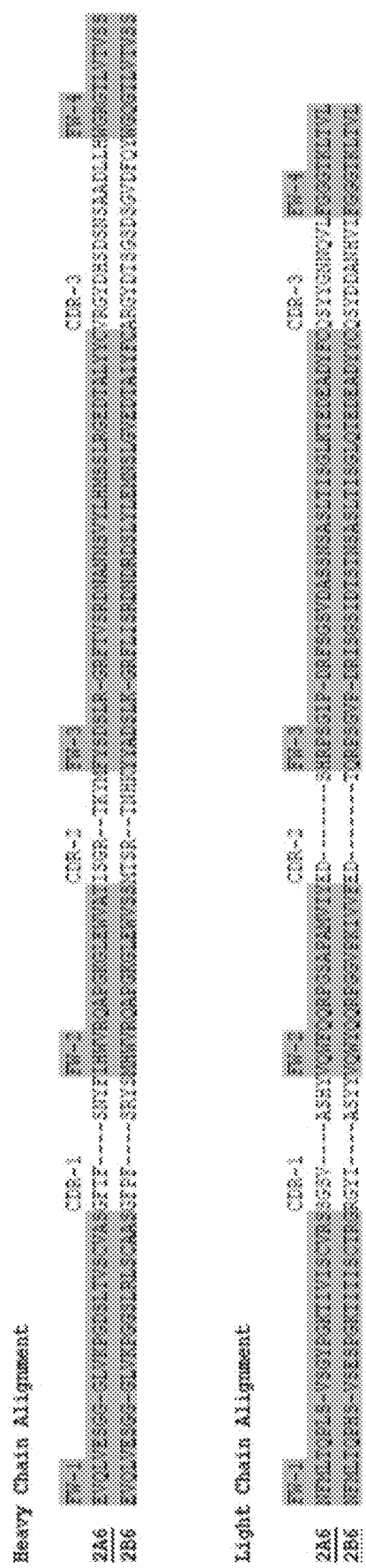
FIG. 1 depicts alignments of the amino acid sequences of the heavy chain variable ($V_H$) and the light chain variable regions ($V_L$) of the IFNγ antibodies, 2A6 and 2AB, with the framework regions (FRs) and complementarity determining region (CDRs) also indicated.

The present disclosure provides methods of treatment and associated compositions based upon the surprising discovery that antibodies capable of blocking the signaling activity of IFNγ are useful in treating HBV infection. Accordingly, the present disclosure provides methods of treatment of HBV infection wherein a patient in need thereof is administered an IFNγ antibody. The IFNγ antibodies useful in the methods and compositions are capable of decreasing, inhibiting, and/or blocking IFNγ signaling activity. As described in greater detail below, the methods of treatment and associated compositions are thus capable of stimulating and/or otherwise restoring normal immune function that can effectively eradicate an HBV infection from the subject in need.

Terminology and Techniques

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of these limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., *Molecular Cloning—A Laboratory Manual* (2nd Ed.), Vols. 1-3, Cold Spring Harbor Laboratory, Cold Spring Harbor, N.Y., 1989 (hereinafter "Sambrook"); *Current Protocols in Molecular Biology*, F. M. Ausubel et al., eds., Current Protocols, a joint venture between Greene Publishing Associates, Inc. and John Wiley & Sons, Inc. (supplemented through 2011) (hereinafter "Ausubel"); *Antibody Engineering*, Vols. 1 and 2, R. Kontermann and S. Dubel, eds., Springer-Verlag, Berlin and Heidelberg (2010); *Monoclonal Antibodies: Methods and Protocols*, V. Ossipow and N. Fischer, eds., 2nd Ed., Humana Press (2014); *Therapeutic Antibodies: From Bench to Clinic*, Z. An, ed., J. Wiley & Sons, Hoboken, N.J. (2009); and *Phage Display*, Tim Clackson and Henry B. Lowman, eds., Oxford University Press, United Kingdom (2004).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for describing particular embodiments only and is not intended to be limiting. For purposes of interpreting this disclosure, the following description of terms will apply and, where appropriate, a term used in the singular form will also include the plural form and vice versa.

"IFNγ," "IFNg," or "interferon-gamma," as used herein, refers to the various forms of the dimerized soluble cytokine, interferon gamma, that is a member of the type II class of interferons, including but not limited to, the naturally occurring IFNγ from primates (e.g., human, rhesus, and cynomolgus), rodents, various pre- and post-translational forms of IFNγ (e.g., pro-human IFNγ, mature-human IFNγ, or truncated-human IFNγ), and recombinant forms of IFNγ.

"Hepatitis B infection" or "HBV infection," as used herein, refers to the presence in an organism of the hepatitis B virus, and is intended to include a short-term or acute infection, a long-term or chronic infection, and a dormant or latent infection.

"Antibody," as used herein, refers to a molecule comprising one or more polypeptide chains that specifically binds to, or is immunologically reactive with, a particular antigen. Exemplary antibodies of the present disclosure include native antibodies, whole antibodies, monoclonal antibodies, polyclonal antibodies, chimeric antibodies, humanized antibodies, human antibodies, multispecific (or heteroconjugate) antibodies (e.g., bispecific antibodies), monovalent antibodies, multivalent antibodies, antigen-binding antibody fragments (e.g., Fab', F(ab')2, Fab, Fv, rIgG, and scFv fragments), antibody fusions, and synthetic antibodies (or antibody mimetics).

"IFNγ antibody," "anti-IFNγ antibody" or "antibody that binds IFNγ" refers to an antibody that binds IFNγ with sufficient affinity such that the antibody is useful as a diagnostic and/or therapeutic agent in targeting IFNγ. In some embodiments, the extent of binding of an IFNγ antibody to an unrelated, non-IFNγ antigen is less than about 10% of the binding of the antibody to IFNγ as measured, e.g., by a radioimmunoassay (RIA). In some embodiments, an antibody that binds to IFNγ has a dissociation constant (Kd) of <1 μM, <100 nM, <10 nM, <1 nM, <0.1 nM, <0.01 nM, or <0.01 nM (e.g., $10^{-8}$ M or less, e.g., from $10^{-8}$ M to $10^{-13}$ M, e.g., from $10^{-9}$ M to $10^{-13}$ M).

"Full-length antibody," "intact antibody," or "whole antibody" are used herein interchangeably to refer to an antibody having a structure substantially similar to a native antibody structure or having heavy chains that contain an Fc region as defined herein.

"Antibody fragment" or "antigen binding fragment" refers to a portion of a full-length antibody which is capable of binding the same antigen as the full-length antibody. Examples of antibody fragments include, but are not limited to, Fv, Fab, Fab', Fab'-SH, F(ab')2; diabodies; linear antibodies; single-chain antibody molecules (e.g., scFv); and multispecific antibodies formed from antibody fragments.

"Class" of an antibody refers to the type of constant domain or constant region possessed by its heavy chain. There are five major classes of antibodies: IgA, IgD, IgE, IgG, and IgM, and several of these are further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

"Variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt et al., Kuby Immunology, 6th ed., W.H. Freeman and Co., page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano et al., J. Immunol. 150: 880-887 (1993); Clarkson et al., Nature 352:624-628 (1991)).

"Hypervariable region" or "HVR," as used herein, refers to each of the regions of an antibody variable domain which are hypervariable in sequence and/or form structurally defined loops ("hypervariable loops"). Generally, native antibodies comprise four chains with six HVRs; three in the heavy chain variable domains, VH (H1, H2, H3), and three in the light chain variable domains, VL (L1, L2, L3). The HVRs generally comprise amino acid residues from the hypervariable loops and/or from the "complementarity determining regions" (CDRs). Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987)). Unless otherwise indicated, HVR residues and other residues in the variable domain (e.g., FR residues) are numbered herein according to Kabat et al., Sequences of Proteins of Immunological Interest, 5th Ed. Public Health Service, National Institutes of Health, Bethesda, Md. (1991).

"Complementarity determining region," or "CDR," as used herein, refers to the regions within the hypervariable regions of the variable domain which have the highest sequence variability and/or are involved in antigen recognition. Generally, native antibodies comprise four chains with six CDRs; three in the heavy chain variable domains, VH (H1, H2, H3), and three in the light chain variable domains, VL (L1, L2, L3). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35 of H1, 50-65 of H2, and 95-102 of H3. (Kabat et al., supra). With the exception of CDR-H1 in VH, CDRs generally comprise the amino acid residues that form the hypervariable loops.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

"Native antibody" refers to a naturally occurring immunoglobulin molecule. For example, native IgG antibodies are heterotetrameric glycoproteins of about 150 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human HVRs and amino acid sequences from human FRs. In certain embodiments, a humanized antibody will comprise substantially all of at least one, and typically two, variable domains, in which all or substantially all of the FTVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Isolated antibody," as used herein, is intended to refer to an antibody that is substantially free of other antibodies having different antigenic specificities (e.g., an isolated antibody that specifically binds IFNγ is substantially free of antibodies that specifically bind antigens other than IFNγ). An isolated antibody that specifically binds IFNγ may, however, have cross-reactivity to other antigens, such as IFNγ molecules from other species. Moreover, an isolated antibody may be substantially free of other cellular material and/or chemicals.

"Human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

"Human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

"Recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germ line $V_H$ and $V_L$ sequences, may not naturally exist within the human antibody germline repertoire in vivo.

"Affinity" refers to the strength of the sum total of noncovalent interactions between a single binding site of a molecule (e.g., an antibody) and its binding partner (e.g., an antigen). "Binding affinity" refers to intrinsic binding affinity which reflects a 1:1 interaction between members of a binding pair (e.g., antibody and antigen). The affinity of a molecule X for its partner Y can generally be represented by the equilibrium dissociation constant (KD). Affinity can be measured by common methods known in the art, including those described herein. Specific illustrative and exemplary embodiments for measuring binding affinity are described in the following.

"Binds specifically" or "specific binding" refers to binding of an antibody to an antigen with an affinity value of no more than about $1 \times 10^{-7}$ M.

"Treatment," "treat" or "treating" refers to clinical intervention in an attempt to alter the natural course of a disorder in a subject being treated and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment of HBV infection can include administration of a therapeutically effective amount of pharmaceutical formulation comprising an IFNγ antibody to a subject to prevent, delay development of, slow progression of, or eradicate an HBV infection.

"Pharmaceutical composition" or "composition" or "formulation" refers to a preparation in a form that allows the biological activity of the active ingredient(s) to be effective, and which contain no additional components which are toxic to the subjects to which the formulation is administered.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Therapeutically effective amount," as used herein, refers to the amount of an active ingredient or agent (e.g., a pharmaceutical composition) to achieve a desired therapeutic or prophylactic result, e.g., to treat or prevent a disease, disorder, or condition in a subject. In the case of an HBV infected subject, the therapeutically effective amount of the therapeutic agent is an amount that reduces, prevents, inhibits, and/or relieves to some extent one or more of the symptoms associated with the HBV infection, including the viral load of HBV, and/or the amount of HBsAg detectable in the subject. For therapeutic treatment of HBV infection, efficacy in vivo can, for example, be measured by assessing the duration, severity, and/or recurrence of symptoms, the response rate (RR), duration of response, and/or quality of life.

"Subject" refers to a mammal, including but not limited to, primates (e.g., humans and non-human primates such as monkeys), rodents (e.g., mice and rats), rabbits, and domesticated animals (e.g., cows, sheep, cats, dogs, and horses).

"Subject in need" as referred to herein includes patients with an HBV infection, such as an HBV carrier, one with chronic HBV infection, one with HBV persistence, or one at risk of HBV infection.

"HBV vaccine," as used herein, refers to a preparation that elicits an acquired immune response to HBV and can include both a prophylactic vaccine (i.e., a vaccine administered to a subject not infected with HBV for prophylaxis), or a therapeutic vaccine (e.g., a vaccine administered to a subject already infected with HBV for treatment of the infection). Exemplary therapeutic vaccines can include a DNA vaccine, a viral vector vaccine, a protein vaccine, or a multi-peptide vaccine.

"Immune checkpoint molecule," as used herein, refers to a molecule that functions to regulate an immune system pathway and thereby prevent it from attacking cells unnecessarily. Many immune checkpoint molecules are targets for immunotherapy (e.g., with blocking antibodies) in the treatment of cancer and viral infections. Exemplary immune checkpoint molecules currently targeted for immunotherapy include PD1, PD-L1, CTLA-4, TIGIT, LAG3, PVRIG, KIR, TIM-3, CRTAM, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA.

Methods for Treatment of HBV Infection Using IFNγ Antibodies

The present disclosure provides methods for treating hepatitis B virus infection, comprising administering to a subject in need thereof a composition comprising a therapeutically effective amount of an IFNγ antibody and a pharmaceutically acceptable carrier. Various IFNγ antibody compositions, and modes of administration useful in the methods of treatment are described in greater detail below and exemplified in the Examples. Additionally, methods of treatment further comprising administering an additional therapeutic agent are further described below and exemplified in the Examples.

IFNγ is a dimerized soluble cytokine that is a member of the type II class of interferons. IFNγ is an important immunostimulatory and immunomodulatory molecule that functions as activator of macrophages and inducer of Class II major histocompatibility complex (MHC) molecule expression. IFNγ is produced predominantly by natural killer (NK) and natural killer T (NKT) cells as part of the innate immune response, and by CD4 Th1 and CD8 cytotoxic T lymphocyte (CTL) effector T cells once antigen-specific immunity develops. Aberrant expression of IFNγ has been associated with a number of autoinflammatory and autoimmune diseases. IFNγ importance in the immune system is thought to arise at least in part from an ability to inhibit viral replication. The amino acid and nucleotide sequences and annotation of the human, primate, and other mammalian versions of IFNγ are publicly available. See e.g., full amino acid sequence of human IFNγ at UniProt entry number P01579. The amino acid sequence of human IFNγ is disclosed as SEQ ID NO: 166 of the accompanying Sequence Listing.

Generally, the IFNγ antibodies useful in the methods for treatment of HBV have the functional characteristic of decreasing, inhibiting, and/or blocking (partially or fully) IFNγ signaling activity. In some embodiments, the IFNγ antibodies useful in the methods of the present disclosure are capable of modulating a biological function of IFNγ, neutralizing IFNγ, or decreasing IFNγ binding to its receptor. In some embodiments, the IFNγ antibody may decrease, inhibit, and/or block the signaling activity of pro-human IFNγ, mature-human IFNγ, or truncated-human IFNγ, and/or the ability of pro-human IFNγ, mature-human IFNγ, or truncated-human IFNγ to bind to its receptor; and thereby reduce one or more of IFNγ-dependent cytokine production, IFNγ-dependent T cell dysfunction, IFNγ-dependent immune tolerance, and/or IFNγ-dependent inflammation.

Exemplary IFNγ antibodies useful in the methods of the present disclosure can include, for example, IFNγ antagonists or inhibitors that modulate at least one biological function or activity of IFNγ. Biological functions or activities of IFNγ include, for example, binding the IFNγ receptor (IFNγ-R), modulating (e.g., enhancing) major histocompatibility complex (MHC) class II expression on a cell surface, modulating (e.g., reducing or inhibiting) cell proliferation, and/or modulating an immune response.

In some embodiments the IFNγ antibodies useful in the methods of the present disclosure completely or partially inhibit IFNγ signaling activity. In some embodiments, the IFNγ antibodies completely or partially inhibit IFNγ signaling activity by partially or completely blocking the binding of IFNγ to the IFNγ receptor. It is contemplated, however, that the IFNγ antibodies can also completely or partially inhibit IFNγ signaling by mechanisms that do not involve direct inhibition of IFNγ binding to the IFNγ receptor.

In some embodiments, the IFNγ antibodies useful in the methods and compositions of the present disclosure can be described in terms on the amino acid and encoding nucleotide sequences of the various well-known immunoglobulin features (e.g., CDRs, HVRs, FRs, $V_H$, and $V_L$ domains). Table 1 below provides a summary description of sequences and sequence identifiers for exemplary IFNγ antibodies useful in the methods of the present disclosure, including the IFNγ antibodies described elsewhere herein as "2A6," "2B6," "2A6_Q," (or "2A6Q") and "2A6_A" (or "2A6A"). The sequences are included in the accompanying Sequence Listing.

TABLE 1

IFNγ antibody sequences

| Description | Sequence | SEQ ID NO: |
|---|---|---|
| 2A6 - VH | EVQLVESGGGLVKPGDSLTVSCVAS<u>GFTFSNYFI</u>HWV RQAPGKGLEWVAT<u>ISGRTKYM</u>FYSDSLRGRFTVSRDN ANNSVYLHMSSLRGEDTALYYC<u>VRGYDHSDSNSAADL LH</u>WGRGTLVTVSS | 109 |
| 2A6 - CDR-H1 - IMGT | GFTFSNYF | 120 |
| 2A6 - CDR-H2 - IMGT | ISGRTKYM | 121 |
| 2A6 - CDR-H3 - IMGT | VRGYDHSDSNSAADLLH | 122 |
| 2A6 - CDR-H1 - Kabat | GFTFSNYFIH | 144 |
| 2A6 - CDR-H2 - Kabat | TISGRTKYMFYSDSLRG | 145 |
| 2A6 - CDR-H3 - Kabat | GYDHSDSNSAADLLH | 146 |
| 2B6 - VH | EVQLVESGGGLVKPGGSLRLSCAAS<u>GFPFSRYS</u>MHWV RQAPGKGLEWVS<u>MTSRTNHK</u>YYADSLKGRFLISRDN DRDSLYLEMNSLGVEDTAIYFC<u>ARGYDTSGSDSGVDF QY</u>WGQGTLVTVSS | 110 |
| 2B6 - CDR-H1 - IMGT | GFPFSRYS | 123 |
| 2B6 - CDR-H2 - IMGT | MTSRTNHK | 124 |

TABLE 1-continued

IFNγ antibody sequences

| Description | Sequence | SEQ ID NO: |
|---|---|---|
| 2B6 - CDR-H3 - IMGT | ARGYDTSGSDSGVDFQY | 125 |
| 2B6 - CDR-H1 - Kabat | GFPFSRYSMH | 147 |
| 2B6 - CDR-H2 - Kabat | SMTSRTNHKYYADSLKG | 148 |
| 2B6 - CDR-H3 - Kabat | GYDTSGSDSGVDFQY | 149 |
| 2A6 - VL | NFMLTQPLSVSGYPGKTIVISCVRSSGSVASHYVQWFQQRPGSAPAMVIYEDSHRPSGIPDRFSGSVDASSNSASLTISGLKTEDEADYFCQSYYGNNQVLFGGGTKLTVL | 113 |
| 2A6 - CDR-L1 - IMGT | SGSVASHY | 132 |
| 2A6 - CDR-L2 - IMGT | EDS | 133 |
| 2A6 - CDR-L3 - IMGT | QSYYGNNQVL | 134 |
| 2A6 - CDR-L1 - Kabat | VRSSGSVASHYVQ | 156 |
| 2A6 - CDR-L2 - Kabat | EDSHRPS | 157 |
| 2A6 - CDR-L3 - Kabat | QSYYGNNQVL | 134 |
| 2B6 - VL | NFMLTQPHSVSESPGKTITISCTRGRGYIASYYVQWYQQRPGGVPKIVVFEDTQRPSGVPDRISGSIDTSTNSASLTISGLQTEDEADYYCQSYDDANHVIFGGGTKLTVL | 114 |
| 2B6 - CDR-L1 - IMGT | RGYIASYY | 135 |
| 2B6 - CDR-L2 - IMGT | EDT | 136 |
| 2B6 - CDR-L3 - IMGT | QSYDDANHVI | 137 |
| 2B6 - CDR-L1 - Kabat | TRGRGYIASYYVQ | 158 |
| 2B6 - CDR-L2 - Kabat | EDTQRPS | 159 |
| 2B6 - CDR-L3 - Kabat | QSYDDANHVI | 137 |
| 2A6_A - VH | EVQLVESGGGLVKPGDSLTVSCVASGFTFSNYFIHWVRQAPGKGLEWVATISGRTKYMFYSDSLRGRFTVSRDNAANSVYLHMSSLRGEDTALYYCVRGYDHSDSNSAADLLHWGRGTLVTVSS | 164 |
| 2A6_Q - VH | EVQLVESGGGLVKPGDSLTVSCVASGFTFSNYFIHWVRQAPGKGLEWVATISGRTKYMFYSDSLRGRFTVSRDNAQNSVYLHMSSLRGEDTALYYCVRGYDHSDSNSAADLLHWGRGTLVTVSS | 165 |
| 2A6 - Heavy Chain | EVQLVESGGGLVKPGDSLTVSCVASGFTFSNYFIHWVRQAPGKGLEWVATISGRTKYMFYSDSLRGRFTVSRDNANNSVYLHMSSLRGEDTALYYCVRGYDHSDSNSAADLLHWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 183 |
| 2A6 - Light Chain | NFMLTQPLSVSGYPGKTIVISCVRSSGSVASHYVQWFQQRPGSAPAMVIYEDSHRPSGIPDRFSGSVDASSNSASLTISGLKTEDEADYFCQSYYGNNQVLFGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | 184 |
| 2B6 - Heavy Chain | EVQLVESGGGLVKPGGSLRLSCAASGFPFSRYSMHWVRQAPGKGLEWVSSMTSRTNHKYYADSLKGRFLISRDNDRDSLYLEMNSLGVEDTAIYFCARGYDTSGSDSGVDFQYWGQGTLVTVSSASTKGPSVFPLAPSSKSTSGGTAA | 185 |

TABLE 1-continued

IFNγ antibody sequences

| Description | Sequence | SEQ ID NO: |
|---|---|---|
| | LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLM ISRTPEVTCVVVDVSHEDPEVKFNWYVDGVEVHNAKT KPREEQYNSTYRVVSVLTVLHQDWLNGKEYKCKVSNK ALPAPIEKTISKAKGQPREPQVYTLPPSREEMTKNQV SLTCLVKGFYPSDIAVEWESNGQPENNYKTTPPVLDS DGSFFLYSKLTVDKSRWQQGNVFSCSVMHEALHNHYT QKSLSLSPGK | |
| 2B6 - Light Chain | NFMLTQPHSVSESPGKTITISCTRGRGYIASYYVQWY QQRPGGVPKIVVFEDTQRPSGVPDRISGSIDTSTNSA SLTISGLQTEDEADYYCQSYDDANHVIFGGGTKLTVL GQPKANPTVTLFPPSSEELQANKATLVCLISDFYPGA VTVAWKADGSPVKAGVETTKPSKQSNNKYAASSYLSL TPEQWKSHRSYSCQVTHEGSTVEKTVAPTECS | 186 |
| 2A6_A - Heavy Chain | EVQLVESGGGLVKPGDSLTVSCVASGFTFSNYFIHWV RQAPGKGLEWVATISGRTKYMFYSDSLRGRFTVSRDN AANSVYLHMSSLRGEDTALYYCVRGYDHSDSNSAADL LHWGRGTLVTVSSASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLM ISRTPEVTCVVVDVSHEDPEVKFNWYVDGVEVHNAKT KPREEQYNSTYRVVSVLTVLHQDWLNGKEYKCKVSNK ALPAPIEKTISKAKGQPREPQVYTLPPSREEMTKNQV SLTCLVKGFYPSDIAVEWESNGQPENNYKTTPPVLDS DGSFFLYSKLTVDKSRWQQGNVFSCSVMHEALHNHYT QKSLSLSPGK | 187 |
| 2A6_Q - Heavy Chain | EVQLVESGGGLVKPGDSLTVSCVASGFTFSNYFIHWV RQAPGKGLEWVATISGRTKYMFYSDSLRGRFTVSRDN AQNSVYLHMSSLRGEDTALYYCVRGYDHSDSNSAADL LHWGRGTLVTVSSASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLM ISRTPEVTCVVVDVSHEDPEVKFNWYVDGVEVHNAKT KPREEQYNSTYRVVSVLTVLHQDWLNGKEYKCKVSNK ALPAPIEKTISKAKGQPREPQVYTLPPSREEMTKNQV SLTCLVKGFYPSDIAVEWESNGQPENNYKTTPPVLDS DGSFFLYSKLTVDKSRWQQGNVFSCSVMHEALHNHYT QKSLSLSPGK | 188 |

Additional, IFNγ antibodies useful in the methods and compositions of the present disclosure include any antibody known in the art to specifically bind IFNγ and neutralize, inhibit, decrease, and/or otherwise block the IFNγ signaling activity. Exemplary antibodies known in the art include the following IFNγ antibodies: AMG-811 (described in e.g., U.S. Pat. No. 7,335,743 B2), NI-0501 (described in e.g., U.S. Pat. No. 7,700,098 B2), HuZAF (described in e.g., U.S. Pat. No. 6,329,511 B1). The disclosure of each of U.S. Pat. Nos. 7,335,743 B2, 7,700,098 B2, and 6,329,511 B1, are hereby incorporated herein in its entirety by reference.

Generally, the IFNγ antibodies useful in the methods of treatment of the present disclosure exhibit high-affinity binding to IFNγ. In some embodiments, the anti-IFNγ antibodies provided herein have an equilibrium dissociation constant (KD) for binding to IFNγ of <100 nM, <10 nM, <1 nM, <0.1 nM, <0.01 nM, or <0.001 nM (e.g., $10^{-8}$ M or less, from $10^{-8}$ M to $10^{-13}$ M, e.g., from $10^{-9}$ M to $10^{-13}$ M).

Further, the anti-IFNγ antibodies useful in the methods disclosed herein include antibodies capable of high-affinity binding to human IFNγ, cynomolgus monkey IFNγ, and in some embodiments, high-affinity binding to both human IFNγ and cynomolgus IFNγ. More specifically, in some embodiments, the IFNγ antibodies useful in the methods of the present disclosure bind to human IFNγ with a binding affinity of $1\times10^{-8}$ M or less, $1\times10^{-9}$ M or less, $1\times10^{-10}$ M or less, or $1\times10^{-11}$ M or less. In some embodiments, the anti-IFNγ antibodies of the present disclosure bind to cynomolgus IFNγ with a binding affinity of $1\times10^{-8}$ M or less, $1\times10^{-9}$ M or less, $1\times10^{-10}$ M or less, or $1\times10^{-11}$ M or less. In some embodiments, the anti-IFNγ antibodies of the present disclosure bind to both human IFNγ and cynomolgus IFNγ with a binding affinity of $1\times10^{-8}$ M or less, $1\times10^{-9}$ M or less, $1\times10^{-10}$ M or less, or $1\times10^{-11}$ M or less.

Generally, the binding affinity of IFNγ antibodies can be determined using any of a variety of assays and expressed in terms of a variety of quantitative values. Specific IFNγ binding assays useful in determining affinity of the antibodies are disclosed in the Examples herein. Additionally, antigen binding assays are known in the art and can be used herein including without limitation any direct or competitive binding assays using techniques such as western blots, radioimmunoassays, enzyme-linked immunoabsorbent assay (ELISA), "sandwich" immunoassays, surface plasmon resonance-based assay (such as the BIAcore assay as described in WO2005/012359), immunoprecipitation assays, fluorescent immunoassays, and protein A immunoassays.

In some embodiments, the anti-IFNγ antibodies useful in the methods of the present disclosure decrease, inhibit, and/or fully-block IFNγ binding to its cognate receptor, IFNγ-R, and thereby modulate immune regulation and/or immune signaling mediated by IFNγ. The ability of the IFNγ antibodies to inhibit these immune regulatory and immune signaling pathways mediated by IFNγ binding can be assayed in vitro using known cell-based assays including the various cell-based assays described in the Examples of the present disclosure.

Accordingly, in some embodiments, the IFNγ antibodies useful in the methods of the present disclosure are characterized by an ability to enhance a measurable immune response in human PBMCs stimulated by staphylococcal enterotoxin B (SEB) by at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, or at least 2.20-fold. For example, in some embodiments, the IFNγ antibody increases IL-2 production and/or cell proliferation in SEB-stimulated human PBMCs by at least at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, or at least 2.20-fold. Additional, functional characteristics of exemplary IFNγ antibodies useful in the methods of the present disclosure are described further below and in the Examples.

As described above, it is contemplated that the IFNγ antibodies useful in the methods for treating HBV infection of the present disclosure can include any immunoglobulin comprising one or more polypeptide chains that specifically binds to or is immunologically reactive with IFNγ. Accordingly, IFNγ antibodies useful in the methods of the present disclosure an include native antibodies, whole antibodies, monoclonal antibodies, polyclonal antibodies, chimeric antibodies, humanized antibodies, human antibodies, multispecific (or heteroconjugate) antibodies (e.g., bispecific antibodies), monovalent antibodies, multivalent antibodies, antigen-binding antibody fragments (e.g., Fab', F(ab')2, Fab, Fv, rIgG, and scFv fragments), antibody fusions, and synthetic antibodies (or antibody mimetics).

In some embodiments of the present disclosure the IFNγ antibody is a glycoprotein comprising at least two heavy (H) chains and two light (L) chains inter-connected by disulfide bonds, or an antigen binding portion thereof. Each heavy chain comprises a heavy chain variable region (abbreviated herein as $V_H$) and a heavy chain constant region. The heavy chain constant region is comprised of three domains, CH1, CH2, and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

In some embodiments according to the present disclosure, the IFNγ antibody may be an immunoglobulin molecule, an Fv, a disulfide linked Fv, a monoclonal antibody, an scFv, a chimeric antibody, a single domain antibody, a CDR-grafted antibody, a diabody, a humanized antibody, a multispecific antibody, an Fab, a dual specific antibody, an Fab' fragment, a bispecific antibody, an F(ab')₂ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody, a dAb fragment, an isolated complementary determining region (CDR), or a single chain antibody. Particularly, the IFNγ antibody may be a human protein or a humanized binding protein.

In some embodiments of the present disclosure the IFNγ antibody is an "antigen-binding fragment" such as a diabody, a Fab, a Fab', a F(ab')₂, an Fv fragment, a disulfide stabilized Fv fragment (dsFv), a (dsFv)₂, a bispecific dsFv (dsFv– dsFv'), a disulfide stabilized diabody (ds diabody), a single-chain antibody molecule (scFv), an scFv dimer (bivalent diabody), a multispecific antibody formed from a portion of an antibody comprising one or more CDRs, or any other antibody fragment that binds to an antigen but does not comprise a complete antibody structure. In such embodiments, the antigen-binding fragment is capable of binding to the same IFNγ antigen to which the parent antibody or a parent antibody fragment (e.g., a parent scFv) binds. In certain embodiments, the antigen-binding fragment may comprise one or more CDRs from a particular human antibody grafted to a framework region from one or more different human antibodies.

Among the above-described antigen-binding fragments, a Fab, which is a structure having the light chain and heavy chain variable regions, the light chain constant region, and the heavy chain first constant region (CH1), has one antigen binding site. A Fab' differs from the Fab in that the Fab' has a hinge region including at least one cysteine residue at the C-terminal of the heavy chain CH1 domain. A F(ab')2 is produced when cysteine residues at the hinge region of Fab' are joined by a disulfide bond.

An Fv is a minimal antibody fragment, having only heavy chain variable regions and light chain variable regions, and a recombinant technique for producing the Fv fragment is well known in the art. "Single-chain Fv antibody" or "scFv" refers to an engineered antibody consisting of a light chain variable region and a heavy chain variable region connected to one another directly or via a peptide linker sequence. A two-chain Fv may have a structure in which heavy chain variable regions are linked to light chain variable regions by a non-covalent bond, and a single-chain Fv may generally form a dimer structure as in the two-chain Fv, wherein heavy chain variable regions are covalently bound to light chain variable regions via a peptide linker or the heavy and light chain variable regions are directly linked to each other at the C-terminals thereof. The linker may be a peptide linker including 1 to 100 or 2 to 50 any amino acids, and proper sequences thereof have been known in the art.

The antigen-binding fragment may be obtained using a protease (for example, a whole antibody can be digested with papain to obtain Fab fragments, can be digested with pepsin to obtain F(ab')2 fragments), or may be prepared by a genetic recombinant technique.

In some embodiments of the methods of the present disclosure, the IFNγ antibody can be a multispecific antibody, e.g., a bispecific antibody. In some embodiments, the multispecific antibody is a monoclonal antibody having at least two different binding sites, each with a binding specificity for a different antigen, at least one of which specifically binds IFNγ. In some embodiments, the multispecific antibody is a bispecific antibody comprising a specificity for IFNγ and a specificity for another antigen that mediates immune regulation, and/or immune signaling. In some embodiments of the bispecific antibody, the other specificity is for an antigen that is an immune checkpoint molecule selected from PD1, PD-L1, CTLA-4, TIGIT, LAGS, PVRIG, KIR, TIM-3, CRTAM, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA. In some embodiment the anti-IFNγ bispecific antibody, the other antigen for which the antibody has specificity is selected from PD1, PD-L1, and CTLA-4.

Techniques for making multispecific antibodies include, but are not limited to, recombinant co-expression of two immunoglobulin heavy chain-light chain pairs having different specificities (see e.g., Milstein and Cuello, *Nature* 305: 537 (1983), WO 93/08829, and Traunecker et al., EMBOJ. 10: 3655 (1991)). "Knob-in-hole" engineering can also be used to generate bispecific antibodies useful with the anti-IFNγ antibodies of the present disclosure. Techniques for knob-in-hole engineering are known in the art and described in e.g., U.S. Pat. No. 5,731,168.

In some embodiments, the IFNγ antibody useful in the methods of the present disclosure can be altered to increase or decrease the extent to which the antibody is glycosylated. Addition or deletion of glycosylation sites to an antibody can be carried out by altering the amino acid sequence such that one or more glycosylation sites is created or removed. For instance, the present disclosure provides exemplary IFNγ antibodies 2A6_A and 2A6_Q that have their sequences modified to remove an N-linked glycosylation site at position 76 of the $V_H$ region.

It also is contemplated that carbohydrates attached to the Fc region can be altered. Typically, native antibodies produced by mammalian cells comprise a branched, biantennary oligosaccharide attached by an N-linkage to the asparagine at about position 297 ("N297") of the CH2 domain of the Fc region (see, e.g., Wright et al. TIBTECH 15:26-32 (1997)). The oligosaccharide may include various carbohydrates, such as mannose, N-acetyl glucosamine (GlcNAc), galactose, and sialic acid, as well as, a fucose attached to a GlcNAc in the "stem" of the bi-antennary oligosaccharide structure. In some embodiments, the modifications of the oligosaccharide of an Fc region of an antibody can create a variant with certain improved properties. In some embodiments, the IFNγ antibody of the present disclosure can be a variant of a parent antibody, wherein the variant comprises a carbohydrate structure that lacks fucose attached (directly or indirectly) to an Fc region. For example, the amount of fucose in such antibody may be from about 1% to about 80%, from about 1% to about 65%, from about 5% to about 65%, or from about 20% to about 40%. The amount of fucose can be determined by calculating the average amount of fucose within the sugar chain at N297, relative to the sum of all glyco-structures attached to Asn 297 (e.g., complex, hybrid and high mannose structures) as measured by MALDI-TOF mass spectrometry (see e.g., WO 2008/077546). N297 refers to the asparagine residue located at about position 297 in the Fc region (Eu numbering of Fc region residues); however, N297 may also be located about ±3 amino acids upstream or downstream of position 297, i.e., between positions 294 and 300, due to minor sequence variations in antibodies.

In some embodiments, the fucosylation variants can have improved ADCC function. See, e.g., US Patent Publication Nos. US 2003/0157108, or US 2004/0093621. Examples of "defucosylated" or "fucose-deficient" antibodies and associated methods for preparing them are disclosed in e.g., US2003/0157108; US2003/0115614; US2002/0164328; US2004/0093621; US2004/0132140; US2004/0110704; US2004/0110282; US2004/0109865; WO2000/61739; WO2001/29246; WO2003/085119; WO2003/084570; WO2005/035586; WO2005/035778; WO2005/053742; WO2002/031140; Okazaki et al. J. Mol. Biol. 336: 1239-1249 (2004); Yamane-Ohnuki et al. Biotech. Bioeng. 87: 614 (2004).

Cell lines useful for producing defucosylated antibodies include Led 3 CHO cells deficient in protein fucosylation (see e.g., Ripka et al. Arch. Biochem. Biophys. 249:533-545 (1986); US2003/0157108, and WO2004/056312), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

In some embodiments, IFNγ antibodies useful in the methods of the present disclosure can comprise one or more amino acid modifications in the Fc region (i.e., an Fc region variant). The Fc region variant may comprise a human Fc region sequence (e.g., a human IgG1, IgG2, IgG3, or IgG4 Fc region) comprising an amino acid substitution at one or more amino acid residue positions. A wide range of Fc region variants known in the art that are useful with the anti-IFNγ antibodies of the present disclosure are described below.

In some embodiments, it is contemplated that the IFNγ antibody is an Fc region variant which has altered effector function. In some embodiments, the antibody with altered effector function possesses some (but not all of) the effector functions, decreased effector function, or none of the effector functions (e.g., effectorless) of the parent antibody. Effectorless Fc region variants are more desirable for certain applications where effector function (such as ADCC) is unnecessary or deleterious, and/or in vivo half-life of the antibody is important. Fc region variant antibodies with reduced effector function, or which are effectorless, can include an amino acid substitution at one or more of the following Fc region positions: 238, 265, 269, 270, 297, 327 and 329. (see, e.g., U.S. Pat. No. 6,737,056). Such Fc region variants can include amino acid substitutions at two or more of positions 265, 269, 270, 297 and 327. Such Fc region variants can also include substitutions of both residues 265 and 297 to alanine (see e.g., U.S. Pat. No. 7,332,581).

Accordingly, in one embodiment the present disclosure provides a method for treating hepatitis B virus (HBV) infection, comprising administering to a subject in need thereof a composition comprising a therapeutically effective amount of an IFNγ antibody and a pharmaceutically acceptable carrier.

Thus, the exemplary cell-based model studies support a mechanism whereby an IFNγ antibody can neutralize cell-based pathways that are associated with increased rates of chronic HBV infection. In other words, the present invention suggests that an IFNγ antibody can be used to provide an improved method for the treatment of HBV.

Modes for Administering IFNγ Antibody Compositions Administration to a subject in need of a composition or formulation comprising an IFNγ antibody in accordance with the methods of treatment provides a therapeutic effect that protects the subject from and/or treats the progression of an HBV infection.

In some embodiments of the methods of treatment of the present disclosure, the IFNγ antibody composition or formulation comprising an IFNγ antibody is administered to a subject by any mode of administration that delivers the agent systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of HBV infection of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebro spinal, and intrasternal injection and infusion.

In an embodiment according to the methods of the present disclosure, the IFNγ antibody may be administered to the subject in need thereof by at least one route selected from the group consisting of parenteral, subcutaneous, intramuscular, intravenous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal. In one embodiment, the IFNγ antibody may be administered to the subject in need intravenously.

In some embodiments, a formulation of the IFNγ antibody is formulated such that the antibody is protected from inactivation in the gut. Accordingly, the method of treatments can comprise oral administration of the formulation.

In some embodiments, the present disclosure provides uses of compositions or formulations comprising an IFNγ antibody as a medicament for the treatment of an HBV infection. Additionally, in some embodiments, the present disclosure also provides for the use of a composition or a formulation comprising an IFNγ antibody in the manufacture or preparation of a medicament for the treatment of an HBV infection. In a further embodiment, the medicament is for use in a method for treating an HBV infection comprising administering to a subject in need thereof an effective amount of the medicament. In certain embodiments, the medicament further comprises an effective amount of at least one additional therapeutic agent, or treatment.

In a further embodiment, the medicament is for use in treating HBV infection in a subject comprising administering to the subject an amount effective of the medicament to treat the HBV infection.

For the treatment of a HBV infection, the appropriate dosage of the IFNγ antibody contained in the compositions and formulations of the present disclosure (when used alone or in combination with one or more other additional therapeutic agents) will depend on factors including the severity and course of the disease, whether the antibody is administered for preventive or therapeutic purposes, the previous therapy administered to the patient, the patient's clinical history and response to the antibody, and the discretion of the attending physician.

Generally, a treatment regimen useful in the methods of the present disclosure can be decided by the medical personnel of the subject in need. The IFNγ antibodies of the present disclosure when included in the compositions and formulations described herein, can be suitably administered to the patient at one time, or over a series of treatments. Various dosing schedules including but not limited to single or multiple administrations over various time-points, bolus administration, and pulse infusion are contemplated herein.

In some embodiments of the methods, the composition comprising an IFNγ antibody may be administered to the subject in need more than once a day, at least once a day, at least once a week, or at least once a month.

Depending on the type and severity of the HBV infection, about 1 μg/kg to 15 mg/kg of IFNγ antibody in a formulation of the present disclosure is an initial candidate dosage for administration to a human subject, whether, for example, by one or more separate administrations, or by continuous infusion. Generally, the administered dosage of the antibody would be in the range from about 0.05 mg/kg to about 10 mg/kg. In some embodiments, one or more doses of about 0.5 mg/kg, 2.0 mg/kg, 4.0 mg/kg or 10 mg/kg (or any combination thereof) may be administered to a patient.

Dosage administration can be maintained over several days or longer, depending on the condition of the subject, for example, administration can continue until the HBV infection is sufficiently treated, as determined by methods known in the art. In some embodiments, an initial higher loading dose may be administered, followed by one or more lower doses. However, other dosage regimens may be useful. The progress of the therapeutic effect of dosage administration can be monitored by conventional techniques and assays.

Accordingly, in some embodiments of the methods of the present disclosure, the administration of the IFNγ antibody comprises a daily dosage from about 1 mg/kg to about 100 mg/kg. In some embodiments, the dosage of IFNγ antibody comprises a daily dosage of at least about 1 mg/kg, at least about 5 mg/kg, at least about 10 mg/kg, at least about 20 mg/kg, or at least about 30 mg/kg.

Combination Treatment Methods with Other Therapeutic Agents

In an embodiment according to the present invention, the method may further comprise the step of administering at least one additional therapeutic agent. For example, the additional therapeutic agent may be administered to the subject in need thereof in combination with the IFNγ antibody composition—e.g., administered at the same time as the IFNγ antibody composition; before administration of the IFNγ antibody composition; or after administration of the IFNγ antibody composition. In some embodiments, the additional therapeutic agent may comprise an additional treatment for HBV infection or a treatment for a disease or condition associated with HBV infection. It is contemplated that in the combination treatment method, by administering an IFNγ antibody composition in combination with a therapeutic agent the efficacy of the therapeutic agent may be improved. Without being bound by theory, it is believed that after administering a therapeutically effective amount of the IFNγ antibody composition and an optional additional therapeutic agent, an immune response against HBV may be induced or boosted in the subject in need; seroconversion with respect to HBV may be induced; or a viral load of HBV in the subject in need may be reduced, even to a level when it is undetectable. Additionally, the boosted immune response may comprise production of antibodies or cytokines that further modulate the activity of the immune system.

In one embodiment, the method comprising administering at least one additional therapeutic agent is carried out wherein the additional therapeutic agent is an HBV vaccine. As described elsewhere herein, the HBV vaccines useful in the combination treatment method can include HBV vaccines for prophylaxis as well as therapeutic vaccines for treatment of subjects already infected with HBV. In some embodiments, the therapeutic vaccine is selected from a DNA vaccine, a viral vector vaccine, a protein vaccine, and a multi-peptide vaccine.

As described elsewhere herein, inhibitory immune checkpoint molecules are targets for treatment of some viral infections as well as cancer. Accordingly, in one embodiment, the method comprising administering at least one additional therapeutic agent is carried out wherein the additional therapeutic agent is an antibody that targets an inhibitory immune checkpoint molecule. In some embodiments, the inhibitory immune checkpoint molecule is selected from PD1, PD-L1, and CTLA-4. In some embodiments, the antibody that targets an inhibitory immune checkpoint molecule is selected from an anti-PD1, anti-PD-L1, and an anti-CTLA-4.

In other embodiments according to the present invention, the additional therapeutic agent may be selected from the group consisting of: a therapeutic agent; an imaging agent; a cytotoxic agent; an angiogenesis inhibitor; a kinase inhibitor; a co-stimulation molecule blocker; an adhesion molecule blockers; an anti-cytokine antibody or functional fragment thereof; methotrexate; cyclosporin; rapamycin; FK506; a detectable label or reporter; a TNF antagonist; an anti-rheumatic; a muscle relaxant; a narcotic; a non-steroid anti-inflammatory drug (NSAID); an analgesic; an anesthetic; a sedative; a local anesthetic; a neuromuscular blocker; an antimicrobial; an antipsoriatic; a corticosteroid; an anabolic steroid; an erythropoietin; an immunization; an immunoglobulin; an immunosuppressive; a growth hormone; a hormone replacement drug; a radiopharmaceutical; an antidepressant; an antipsychotic; a stimulant; an asthma medication; a beta agonist; an inhaled steroid; an epinephrine or analog thereof; a cytokine; and a cytokine antagonist; an immunomodulatory agent.

In some embodiments, the additional therapeutic agent is selected from an HBV entry inhibitor, a viral RNA inhibitor, a gene editing agent, an HBsAg secretion inhibitors, a polymerase inhibitor, an interferon, a viral entry inhibitor, a viral maturation inhibitor, a nucleoside reverse transcriptase inhibitor, a capsid assembly inhibitor/modulator, a cccDNA inhibitor, an FXR agonist, a microRNA, a TLR agonist, and an immunomodulators.

In some embodiments, the additional therapeutic agent is selected from entecavir (Baraclude), tenofovir (Viread), lamivudine (Epivir), adefovir (Hepsera) and telbivudine (Tyzeka), interferon alfa-2b, and pegyinterferon alfa-2a.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Analysis of HBV and IFNγ Autoantibodies in dNTM Patients

This example illustrates an analysis of patients with disseminated nontuberculous mycobacterial (dNTM) infections indicating that IFNγ autoantibodies are associated with lower prevalence of HBV.

Study Methodology:

Blood samples were obtained from 44 patients with dNTM infections. The patients were born between about 1921 and 1981 and had an average age of 58.7 years. The blood samples were analyzed the presence of IFNγ autoantibodies using whole blood IL-12p40 expression as described by Lin et al. ("Identification of a major epitope by anti-interferon-γ autoantibodies in patients with mycobacterial disease," *Nat. Med.* (2016) 22(9):994-1001). Serum levels of HBsAg, HBeAg, anti-HBs Ab, anti-HBc Ab were determined.

Results:

As shown in Table 2, only two of the 44 patients with IFNγ autoantibodies (EIP31 and EIP44) tested positive for HBsAg and were diagnosed with chronic HBV infection based on AASLD Hepatitis B Guidance.

TABLE 2

| Patient ID | Sex | Age(y) | Neutralizing anti-IFNg | HBs Ag |
|---|---|---|---|---|
| EIP01 | M | 68 | + | − |
| EIP02 | M | 81 | + | − |
| EIP03 | M | 53 | + | − |
| EIP04 | M | 84 | + | − |
| EIP05 | F | 59 | + | − |
| EIP06 | M | 48 | + | − |
| EIP07 | F | 47 | + | − |
| EIP08 | F | 75 | + | − |
| EIP09 | M | 57 | + | − |
| EIP10 | F | 46 | + | − |
| EIP11 | F | 56 | + | − |
| EIP12 | F | 67 | + | − |
| EIP13 | F | 47 | + | − |
| EIP14 | M | 54 | + | − |
| EIP15 | F | 54 | + | − |
| EIP16 | F | 52 | + | − |
| EIP17 | F | 70 | + | − |
| EIP18 | M | 55 | + | − |
| EIP19 | F | 57 | + | − |
| EIP20 | F | 51 | + | − |
| EIP21 | M | 38 | + | − |
| EIP22 | M | 69 | + | − |
| EIP23 | F | 35 | + | − |
| EIP24 | M | 70 | + | − |
| EIP25 | M | 39 | + | − |
| EIP26 | F | 75 | + | − |
| EIP27 | M | 63 | + | − |
| EIP28 | F | 65 | + | − |
| EIP29 | M | 46 | + | − |
| EIP30 | F | 36 | + | − |
| EIP31 | M | 67 | + | + |
| EIP32 | M | 78 | + | − |
| EIP33 | M | 67 | + | − |
| EIP34 | M | 65 | + | − |
| EIP35 | M | 50 | + | − |
| EIP36 | F | 58 | + | − |
| EIP37 | M | 40 | + | − |
| EIP38 | F |  | + | − |
| EIP39 | M | 48 | + | − |

TABLE 2-continued

| Patient ID | Sex | Age(y) | Neutralizing anti-IFNg | HBs Ag |
|---|---|---|---|---|
| EIP40 | M | 65 | + | − |
| EIP41 | M | 64 | + | − |
| EIP42 | M | 46 | + | − |
| EIP43 | M | 62 | + | − |
| EIP44 | M | 69 | + | + |

The results of Table 2 indicate that the prevalance of chronic HBV in the population of 44 patients with IFNγ autoantibodies was only 4.5% (2/44). In contrast, a published study indicates that the prevalence of chronic HBV infection in the Taiwan population born between 1920 to 1983 was approximately 15-20% (J Formos Med Assoc. 2007 February; 106(2):148-55). A further comparative analysis of these results was carried using a Fisher exact test which yielded an exact test statistic value of 0.0251 with a P-value of P<0.5. This statistical analysis suggests that the proportion of dNTM patients with IFNγ autoantibodies who also have chronic HBV infection is significantly lower than the proportion of chronic HBV infection in the general population.

Without being bound by theory, the above results strongly suggest that the presence of IFNγ autoantibodies in a subject correlates strongly with a decreased rate of chronic HBV infection. This result further thus supports that administration of an IFNγ antibody to a patient may facilitate the prevention or treatment of HBV infection. Additional support for the use of IFNγ antibodies to prevent or treat HBV infection is provided by the cell-based and animal model studies disclosed in the further examples herein.

Example 2: Analysis of IFNγ Signaling Levels in HBV Patient Populations

This example illustrates an analysis of gene expression levels of CXCL9, CXCL10, CXCL11, and STAT1 in livers of HBV patient and healthy donor populations. The increased expression of the CXCL9, CXCL10, CXCL11, and STAT1 genes are known to be associated with increased IFNγ signaling.

Materials and Methods:

Gene Set Enrichment Analysis (GSEA) was carried out using liver microarray data were obtained from the GEO data base. The data included eight healthy liver samples (chip ID: GSM138595, GSM138596, GSM2291960, GSM2291961, GSM2291962, GSM2291963, GSM2291964, GSM2291965) and seven HBV infected liver sample (GSM1629354, GSM1629355, GSM1629356, GSM1629357, GSM1629358, GSM1629359, GSM1629360). All the microarray data was summarized into gene-level information, and the probe names were transformed into gene symbols. The expression data was then log 2-transformed and log 2-transformed values were used to calculate fold-change in expression levels of CXCL9, CXCL10, CXCL11 and STAT1.

Results:

CXCL9, CXCL10, CXCL11 and STAT1 all showed higher expression in the liver of chronic HBV patients (log Fold change >1.5) indicating increased IFNγ signaling associated with chronic HBV infection.

Example 3: Preparation of IFNγ Antibodies for Treatment of HBV Infection

This example illustrates the preparation of various IFNγ antibodies useful in the methods of the present disclosure for treating HBV infection.

A. Isolation of Single Human B Cells by Fluorescence Activated Cell Sorting

Peripheral venous blood samples were collected from human patients with mycobacterial diseases after signed informed consent in accordance with Institutional Review Board (IRB)-reviewed protocols. Mononuclear cells were isolated from the peripheral venous blood of the patients after being purified by Ficoll-Paque (GE Healthcare) density gradient centrifugation according to the manufacturer's instructions. The purified mononuclear cells were resuspended in 5% normal mouse serum (Jackson ImmunoResearch) of FACS buffer (1% FBS, 2 mM EDTA, 0.1% NaN3 in PBS) with the concentration of $1 \times 10^7$ cells/mL and placed on ice for 30 minutes. Meanwhile, the cells were added with 20 μg/mL anti-human CD119 antibody (BioLegend). Then, the cells were washed by FACS buffer and added with 1 μg recombinant IFNγ protein (R&D systems) within $1 \times 10^6$ cells for 20 minutes on ice. Before the sorting process, cells were stained on ice with anti-human IgG PE (BD bioscience), anti-human IgD APC (BD bioscience), anti-human CD3 PE-Cyanine7 (eBioscience), anti-human CD19 APC-eFluor 780 (eBioscience), anti-human IFNγ FITC (BD Bioscience), and 7-Aminoactinomycin D (Sigma) as a DNA marker for 30 minutes. Individual single B cells binding to IFNγ were gated on CD19$^+$IgG$^+$CD3$^-$IgD$^-$FITC$^+$ and then the cells were each sorted into individual wells of 96-well plates containing 18 μL/well of a RT-lysis buffer (which contains 200 ng random hexamer primer (Thermo Scientific), 1 μL of 10 mM each nucleotide dNTP-mix (Thermo Scientific), 0.5% v/v Igepal CA-630 (Sigma), and 40 U Ribolock (Fermentas)), thereby obtaining a lysate mixture having the total RNA of single B cells. The 96-well plates were sealed with aluminum sealing tape (Corning) and immediately stored at −80° C.

B. Single Cell RT-PCR and Ig Gene Amplification

The RT-PCR protocol was carried out manually. cDNA was synthesized in a total volume of 20 μL/well in the above 96-well plate which included 2 μL (50 U) Maxima H minus reverse transcriptase (Thermo Scientific) in DEPC-treated water into each well. The total RNA of each B cell (designated "2A6" and "2B6" B cells) was subjected to reverse transcription (RT) reaction, which was performed at 42° C. for 10 minutes in an annealing step, at 25° C. for 10 minutes in a pre-primer extension step, at 50° C. for 45 minutes in a polymerization step, and at 85° C. for 5 minutes in an enzyme inactivation step. The first strand cDNA thus formed was stored at −20° C.

IgH, Igλ, Igκ V gene transcripts of each B cell were amplified by nested-PCR, with each nested-PCR involving a first round PCR starting from 2.5 μL of the first strand cDNA obtained above as a template, and then a second round PCR using 2.5 μL of unpurified first round PCR product obtained from the first round PCR as a template. All PCR reactions were performed in a total volume of 25 μL per reaction containing 0.5 μM primer mix. Briefly, 200 μM each dNTP (Thermo Scientific) and 0.5 U Phusion High-Fidelity DNA polymerase (Thermo Scientific) with an error rate of about $4.4 \times 10^{-7}$. All PCR reactions were performed with DEPC-treated water. Each of the first and second rounds of the nested PCR reaction was performed for 35 cycles at 98° C. for 10 seconds in a denaturation step, at 65° C. for 15 seconds in an annealing step, and at 72° C. for 30 seconds in an elongation step. The mixes of forward and reverse primers used for PCR of the particular genes are summarized in Table 3.

TABLE 3

| Nested PCR | Primers | IgH V gene (SEQ ID NOs:) | Igκ V gene (SEQ ID NOs:) | Igλ V gene (SEQ ID NOs:) |
|---|---|---|---|---|
| First round | Forward | 1-13 | 24-31 | 40-51 |
|  | Reverse | 63 | 65 | 67 |
| Second round | Forward | 14-23 | 32-39 | 52-62 |
|  | Reverse | 64 | 66 | 68 |

The nucleotide sequences of the Forward and Reverse primers used are described in Table 4 and the accompanying Sequence Listing.

TABLE 4

|  | 5'-3' sequence | SEQ ID NO: |
|---|---|---|
| Forward primer |  |  |
| VH1/7L | accatggactgsacctggag | 1 |
| VH2L | caccatggacacactttgctmcac | 2 |
| VH2-70L | accatggacatactttgttccacg | 3 |
| VH3L | atggagtttgggctgagctg | 4 |
| VH3-21L | atggaactggggctccgctg | 5 |
| VH3-48L | atggagttggggctgtgctg | 6 |
| VH3-49L | catggagtttgggcttagctg | 7 |
| VH3-53L | catggagttttggctgagctg | 8 |
| VH4L | catgaaacacctgtggttcttcct | 9 |
| VH4-39L | aatgaagcacctgtggttcttcct | 10 |
| VH4-59L | acatgaaacatctgtggttcttcct | 11 |
| VH5L | atggggtcaaccgccatcct | 12 |
| VH6L | aatgtctgtctccttcctcatcttcct | 13 |
| VH1/3/5f | saggtgcagctggtgsagtc | 14 |
| VH1-3f | caggtccagcttgtgcagtc | 15 |
| VH1-18f | caggttcagctggtgcagtc | 16 |
| VH1-24f | caggtccagctggtacagtctg | 17 |
| VH2f | caggtcacctgarggagtctggt | 18 |
| VH3-23f | gaggtgcagctgttggagtct | 19 |
| VH4f | cagstgcagctgcaggagt | 20 |
| VH4-34f | caggtgcagctacarcagtgg | 21 |
| VH6f | caggtacagctgcagcagtca | 22 |
| VH7f | caggtgcagctggtgcaat | 23 |
| KV1L | ggtccccgctcagctcctgg | 24 |
| KV1-16L | agtcctcgctcagctcctgg | 25 |
| V2L | gctccctgctcagctcctgg | 26 |
| KV2-24L | gctccttgctcagcttctgg | 27 |
| KV3L | cctgctactctggctcccag | 28 |
| KV4L | atttctctgttgctctggatctctg | 29 |
| KV5L | cttcctcctcctttggatctctg | 30 |

TABLE 4-continued

|  | 5'-3' sequence | SEQ ID NO: |
|---|---|---|
| KV6L | tctgctgctctgggttccag | 31 |
| VK1f | gacatccagwtgacccagtctcc | 32 |
| VK2f | gatattgtgatgacccagactccactct | 33 |
| VK2-28f | gatattgtgatgactcagtctccactct | 34 |
| VK3f | gaaattgtgttgacrcagtctccag | 35 |
| VK3-15f | gaaatagtgatgacgcagtctccag | 36 |
| VK4f | gacatcgtgatgacccagtctc | 37 |
| VK5f | gaaacgacactcacgcagtctc | 38 |
| VK6f | gaaattgtgctgactcagtctcca | 39 |
| LV1L | ggtcctgggcccagtctgtg | 40 |
| LV2L | ggtcctgggcycagtctgcc | 41 |
| LV3L | gctctgwggcctcctatgagct | 42 |
| LV3-12/21L | gctctgtgacctcctatgwgctg | 43 |
| LV3-19L | gttctgtggtttcttctgagctgact | 44 |
| LV4L | ggtctctctcccwgcytgtgc | 45 |
| LV5L | gttccctctcgcaggctgtg | 46 |
| LV5/9L | gktccctctcccagcctgtg | 47 |
| LV6L | gttcttgggccaattttatgctg | 48 |
| LV7L | ggtccaattcycagrctgtggtg | 49 |
| LV8L | gagtggattctcagactgtggtga | 50 |
| LV10L | tgtcagtggtccaggcaggg | 51 |
| LV1-40/50/51f | cagtctgtgytgacgcagcc | 52 |
| LV1-36/44/47f | cagtctgtgctgactcagcca | 53 |
| LV2f | cagtctgccctgactcagcc | 54 |
| LV3f | tcctatgagctgacwcagcca | 55 |
| LV3-19f | tcttctgagctgactcaggacc | 56 |
| LV4/5/9f | cagsctgtgctgactcagcc | 57 |
| LV4-60f | cagcctgtgctgactcaatcat | 58 |
| LV4-69f | cagcttgtgctgactcaatcg | 59 |
| LV6f | aattttatgctgactcagccccac | 60 |
| LV7/8f | cagrctgtggtgacycaggagc | 61 |
| LV10f | caggcagggctgactcagcc | 62 |
| Reverse primers |  |  |
| CγCH1-1 | aggtgtgcacgccgctggtc | 63 |
| CγCH1-2 | ggttcggggaagtagtccttgac | 64 |
| Cκ543-566 | gtttctcgtagtctgctttgctca | 65 |
| Cκ494-516 | gtgctgtccttgctgtcctgct | 66 |
| Cγ156-178 | ttggagggtktggtggtctccac | 67 |

TABLE 4-continued

| Primer | 5'-3' sequence | SEQ ID NO: |
|---|---|---|
| Cγ129-148 | ttgacggggctgcyatctgc | 68 |
| Cγ93-113 | cacrgctcccgggtagaagtc | 69 |

C. Ig V Gene Sequence Analysis

Aliquots of the $V_H$, $V_\kappa$ and $V_\lambda$ chain PCR product of each B cell (obtained from the second round PCR as mentioned above) were purified with QIAquick PCR purification kit (Qiagen) according to the manufacturer's instructions and sequenced with the primers identified by SEQ ID NOs: 64, 66 and 69, respectively (see Table 4). The obtained sequences were analyzed by IMGT®, the international ImMunoGeneTics Information System® (http://www.imgy.org), to identify germline V(D)J gene segments with highest identity.

An alignment of the amino acid sequences of heavy chain variable ($V_H$) and light chain variable regions ($V_L$) of the antibodies encoded by the obtained Ig V gene sequences are shown in FIG. 1 with their framework regions (FRs) and complementarity determining region (CDRs) also indicated. As described below, the two antibodies were named "2A6" and "2B6." The amino acid sequences are also provided in the accompanying Sequence Listing.

D. Expression Vector Cloning

After sequencing, gene-specific primers were chosen from Table 5 according to the V or J segments with highest identity to conduct a further PCR reaction under the similar reaction condition as that of the nested PCR, in which the $V_H$, $V_\kappa$ and $V_\lambda$ chain PCR products of each B cell (obtained from the second round PCR as described above) were used as templates.

TABLE 5

| Primer | 5'-3' sequence | SEQ ID NO: |
|---|---|---|
| SL-VH1/3/5f | gttgctacgcgtgtcctgagcsaggtgcagctggtgsagtc | 70 |
| SL-VH1-3f | gttgctacgcgtgtcctgagccaggtccagcttgtgcagtc | 71 |
| SL-VH1-18f | gttgctacgcgtgtcctgagccaggttcagctggtgcagtc | 72 |
| SL-VH1-24f | gttgctacgcgtgtcctgagccaggtccagctggtacagtctg | 73 |
| SL-VH2f | gttgctacgcgtgtcctg agccaggtcaccttgarggagtctg | 74 |
| SL-VH3-23f | gttgctacgcgtgtcctgagcgaggtgcagctgttggagtct | 75 |
| SL-VH4f | gttgctacgcgtgtcctgagccagstgcagctgcaggagt | 76 |
| SL-VH4-34f | gttgctacgcgtgtcctgagccaggtgcagctacarcagtgg | 77 |
| SL-VH6f | gttgctacgcgtgtcctgagccaggtacagctgcagcagtca | 78 |
| SL-VH7f | gttgctacgcgtgtcctgagccaggtgcagctggtgcaat | 79 |
| SL-JH1/4/5r | gatgggcccttggtgctagctgaggagacggtgaccagg | 80 |
| SL-JH2r | gatgggcccttggtgctagctgaggagacagtgaccagggt | 81 |
| SL-JH3r | gatgggcccttggtgctagctgaagagacggtgaccattgtc | 82 |
| SL-JH6r | gatgggcccttggtgctagctgaggagacggtgaccgtg | 83 |
| SL-VK1f | ggctcccaggtgcacgatgtgacatccagwtgacccagtctcc | 84 |
| SL-VK2f | ggctcccaggtgcacgatgtgatattgtgatgacccagactccactct | 85 |
| SL-VK3f | ggctcccaggtgcacgatgtgaaattgtgttgacrcagtctccag | 86 |
| SL-VK4f | ggctcccaggtgcacgatgtgacatcgtgatgacccagtctc | 87 |
| SL-VK5f | ggctcccaggtgcacgatgtgaaacgacactcacgcagtctc | 88 |
| SL-VK6f | ggctcccaggtgcacgatgtgaaattgtgctgactcagtctcca | 89 |
| SL-JK1r | tgcagccaccgtacgtttgatttccaccttggtccct | 90 |
| SL-JK2r | tgcagccaccgtacgtttgatctccagcttggtccct | 91 |
| SL-JK3r | tgcagccaccgtacgtttgatatccactttggtccca | 92 |
| SL-JK4r | tgcagccaccgtacgtttgatctccaccttggtccct | 93 |
| SL-JK5r | tgcagccaccgtacgtttaatctccagtcgtgtcccttt | 94 |
| SL-LV1-40/50/51f | tccttgcttatgggtccggagtggattctcagtctgtgytgacgcagcc | 95 |
| SL-LV1-36/44/47f | tccttgcttatgggtccggagtggattctcagtctgtgctgactcagcca | 96 |

TABLE 5-continued

| Primer | 5'-3' sequence | SEQ ID NO: |
|---|---|---|
| SL-LV2f | tccttgcttatgggtccggagtggattctcagtctgccctgactcagcc | 97 |
| SL-LV3f | tccttgcttatgggtccggagtggattcttcctatgagctgacwcagcca | 98 |
| SL-LV3-19f | tccttgcttatgggtccggagtggattcttcttctgagctgactcaggac | 99 |
| SL-LV4/5/9f | tccttgcttatgggtccggagtggattctcagsctgtgctgactcagcc | 100 |
| SL-LV4-60/69f | tccttgcttatgggtccggagtggattctcagyctgtgctgactcaatc | 101 |
| SL-LV6f | tccttgcttatgggtccggagtggattctaattttatgctgactcagccc | 102 |
| SL-LV7/8f | tccttgcttatgggtccggagtggattctcagrctgtggtgacycaggag | 103 |
| SL-LV10f | tccttgcttatgggtccggagtggattctcaggcagggctgactcagcc | 104 |
| SL-JL1r | ggccttgggctgacctaggacggtgaccttggtcc | 105 |
| SL-JL2/3f | ggccttgggctgacctaggacggtcagcttggtcc | 106 |
| SL-JL6r | ggccttgggctgacctaggacggtcaccttggtgc | 107 |
| SL-JL7r | ggccttgggctgacctaggacggtcagctgggtgc | 108 |

The selected forward and reverse primers used to prepare vectors encoding the 2A6 and 2B6 antibodies are shown in Table 6.

TABLE 6

| Antibody | $V_H$ chain Forward primer/reverse primer (SEQ ID NOs:) | $V_L$ chain |
|---|---|---|
| 2A6 | 70/80 | 102/106 |
| 2B6 | 70/80 | 102/106 |

Figure 2:
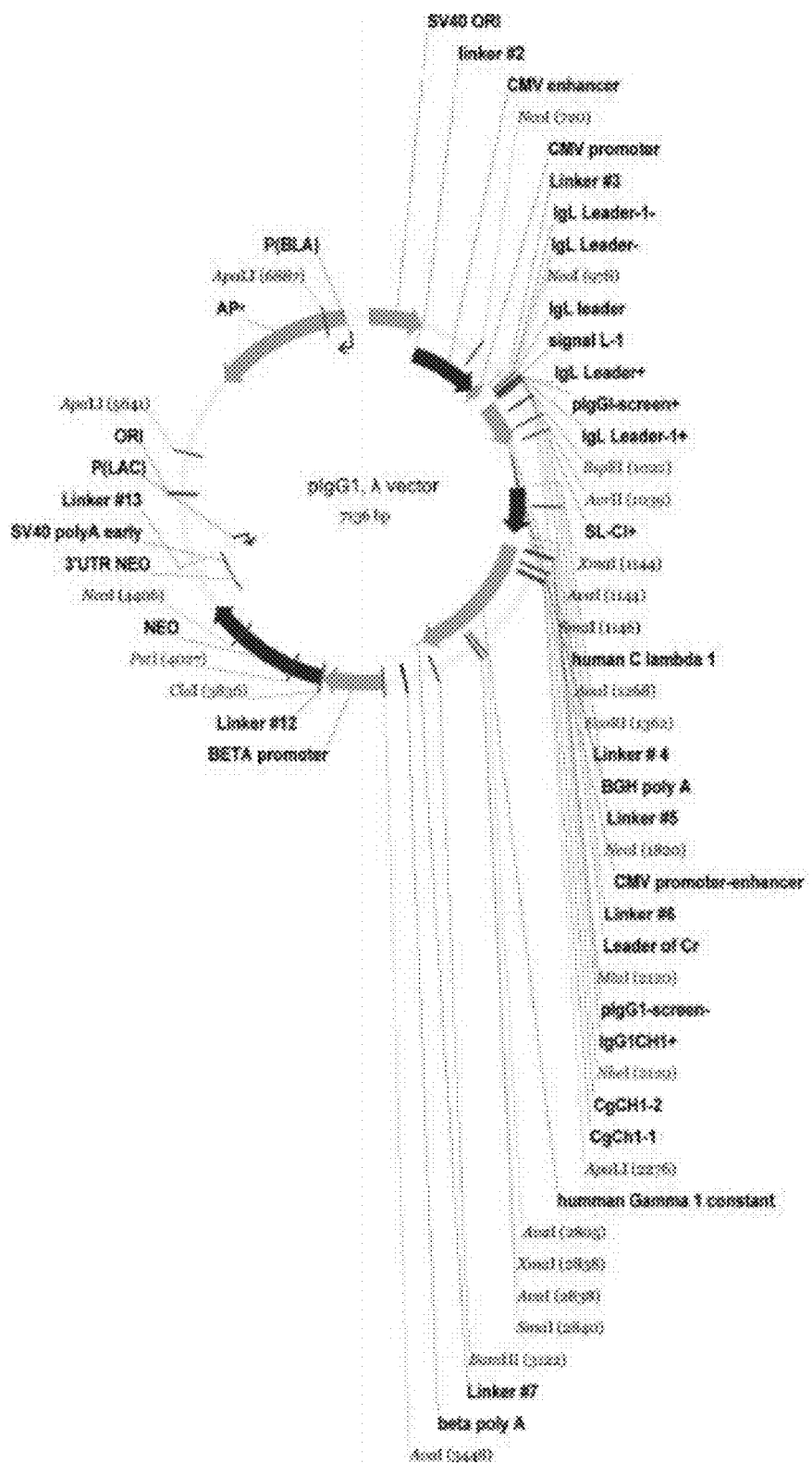
FIG. 2 depicts human $IgG_1\lambda$ expression vector used in preparing recombinant IFNγ antibodies.

The PCR products for each of 2A6-$V_H$, 2A6-$V_L$, 2B6-$V_H$, and 2B6-$V_L$, were purified as described above, followed by recombination into human IgG$_1$λ expression vector shown in FIG. 2 (kindly provided from Dr. Tse-Wen Chang in Academia Sinica, Taiwan). In addition to the two expression vectors, "2A6" and "2B6," a vector also was constructed for expression of an antibody having the 2B6-$V_H$ and 2A6-$V_L$, named "BA."

Recombination of the cloned genes into human IgG$_1$λ expression vector was carried out by GeneArt® Seamless Cloning and Assembly Enzyme Mix (Invitrogen). Competent E. coli were transformed at 42° C. with 5 µL of recombination product. Colonies of the transformed E. coli were screened by PCR using pIgG1κ-screen+ (SEQ ID NO: 117) or pIgG1λ-screen+ (SEQ ID NO: 118) as the forward primer and pIgG1-screen− (SEQ ID NO: 119) as the reverse primer, respectively, shown in Table 7.

TABLE 7

| Primer | 5'-3' sequence | SEQ ID NO: |
|---|---|---|
| pIgG$_1$κ-screen+ | gctcccaggtgcacgatgtg | 117 |
| pIgG$_1$κλ-screen+ | gcttatgggtccggagtggattct | 118 |
| pIgG$_1$-screen− | gatgggcccttggtgctagc | 119 |

PCR products of the expected size (about 1,800 bps) were sequenced for confirmation of identity with the original PCR products. Plasmid DNA was isolated using QIAprep® Spin columns (Qiagen) from 3 mL bacterial cultures of the transformed E. coli grown for 16 hours at 37° C. in Luria-Bertani broth containing 100 µg/mL ampicillin.

E. Cloning of Glycosylation Mutants 2A6_A and 2A6_q

Expression of antibody 2A6 in mammalian cells was found to result in observation of two heavy chain bands upon gel electrophoresis (data not shown). It was noted that 2A6 has an N-linked glycosylation site in its variable region at position 76. The presence of N-linked glycosylation site was confirmed by PNGase F digestion assay. Following PNGase F digestion, 2A6 exhibited reduced size indicating that an N-linked carbohydrate was removed (data not shown). This result suggested that the lower of the two bands of heavy chain observed before PNGase F treatment was due to partial glycosylation of an N-linked glycosylation site. This N-linked partial glycosylation site could make larger-scale production of 2A6 problematic due to lack of molecular homogeneity. A point mutation was designed and conducted to remove the aforesaid N-linked glycosylation site of 2A6.

To generate site-specific glycosylation mutant plasmids, site-directed mutagenesis was performed using Q5 polymerase from NEB. The oligonucleotides used for mutagenesis of each construct are as follows (sense sequence):

c2A6_Q
(SEQ ID NO: 169)
5'-CGTTTCTAGAGACAACGCCCAGAATTCGGTATATCTCCACA-3'
and c2A6_A
(SEQ ID NO: 170)
5'-CGTTTCTAGAGACAACGCCGCCAATTCGGTATATCTCCAC-3'.

Mutant sequences were then verified by DNA sequencing of each construct. After the aforesaid point mutation, the asparagine amino acid at position 76 of the heavy chain variable region of antibody 2A6 was mutated from asparagine (N) to alanine (A) or glutamine (Q). The two variant antibodies were named "2A6_A" (N76A mutation) and "2A6_Q" (N76Q mutation). The heavy chain $V_H$ regions of antibodies 2A6_A and 2A6_Q comprise SEQ ID NO: 164 and SEQ ID NO: 165, respectively.

SDS-PAGE analysis showed that the heavy chains of 2A6_A and 2A6_Q both showed only a sharp single band of lower molecular mass (data not shown) unlike the two bands observed for 2A6, suggesting that the N-linked glycosylation site was successfully disrupted. Mass spectrometry analysis further confirmed that the N76A and N76Q mutations introduced into 2A6_A and 2A6_Q, respectively, resulted in loss of the glycosylation signal.

F. Recombinant IFNγ Antibody Production

FreeStyle™ 293-F cells (Thermo Scientific, R79007) were cultured in a 250-mL flask containing FreeStyle™ 293 expression medium (Gibco, 12338018) under standard conditions with the concentration of $1\times10^6$ cells. Transient transfection of the exponentially growing FreeStyle™ 293-F cells ($1.5$-$2\times10^6$ cells) were performed by linear polyethylenimine (PEI) with an average molecular weight of 25 kDa (Polysciences, Warrington, Pa.) as a transfection reagent and a total of 88 μg of the plasmid DNA. After transfection, the cells were cultured for 3 days and the culture medium was harvested. The culture medium was centrifuged for 10 min at 3000 rpm to remove the FreeStyle™ 293-F cell debris and afterward, the resultant supernatant was collected and filtered through a 0.45 μm filter.

G. Recombinant Antibody Purification

The resultant supernatants as obtained above were subsequently purified with Protein A Sepharose Fast Flow beads (GE Healthcare, 17-1279-01) so as to obtain the recombinant antibodies. In brief, 80 mL of the supernatants were added with 80 μL Protein A Sepharose Fast Flow beads and aliquoted evenly into two 50-ml tubes which were incubated for 24 hours at 4° C. under rotation. Then, the tubes were centrifuged at 3000 rpm for 10 min, and afterward, the resultant supernatants were removed, and the beads were equilibrated with PBS. The equilibrated beads were eluted with 0.1 M glycine (pH 3.0), and the eluates were collected in tubes containing 1 M Tris (pH 8.0) and dialyzed against PBS buffer, so as to obtain the monoclonal antibodies including 2A6, 2B6, 2A6_A, 2A6_Q, and BA anti-INF-γ mAbs, respectively.

For clarity, the CDRs on the $V_H$ chain and $V_L$ chain of each of the monoclonal antibodies are summarized in Table 8 and Table 9, respectively. CDRs were identified based on Kabat (Wu, T. T. and Kabat, E. A., 1970 J. Exp. Med. 132: 211-250) and IMGT systems (Lefranc M.-P. et al., 1999 Nucleic Acids Research, 27, 209-212) by sequence annotation and by internet-based sequence analysis as described at e.g., www.imgt.org/IMGT_vquest/share/textes/index.html, and www.ncbi.nlm.nih.gov/igblast. In Table 8 below, CDRs following "K:" are based on Kabat system, and CDRs following "I:" are based on IMGT system.

TABLE 8

| mAb | $V_H$ CDR1 | $V_H$ CDR2 | $V_H$ CDR3 |
|---|---|---|---|
| 2A6 | I:GFIFSNYF (SEQ ID No. 120) K:GFTFSNYFIH (SEQ ID No. 144) | I:ISGRIKYM (SEQ ID No. 121) K:TISGRTKYMFYSDSLRG (SEQ ID No. 145) | I:VRGYDHSDSNSAADLLH (SEQ ID No. 122) K:GYDHSDSNSAADLLH (SEQ ID No. 146) |
| 2B6 | I:GFPFSRYS (SEQ ID No. 123) K:GFPFSRYSMH (SEQ ID No. 147) | I:MTSRINHK (SEQ ID No. 124) K:SMTSRTNHKYYADSLKG (SEQ ID No. 148) | I:ARGYDTSGSDSGVDFQY (SEQ ID No. 125) K:GYDTSGSDSGVDFQY (SEQ ID No. 149) |
| 2A6_AI | I:GFIFSNYF (SEQ ID No. 120) K:GFTFSNYFIH (SEQ ID No. 144) | I:ISGRIKYM (SEQ ID No. 121) K:TISGRTKYMFYSDSLRG (SEQ ID No. 145) | I:VRGYDHSDSNSAADLLH (SEQ ID No. 122) K:GYDHSDSNSAADLLH (SEQ ID No. 146) |
| 2A6_QI | I:GFIFSNYF (SEQ ID No. 120) K:GFTFSNYFIH (SEQ ID No. 144) | I:ISGRIKYM (SEQ ID No. 121) K:TISGRTKYMFYSDSLRG (SEQ ID No. 145) | I:VRGYDHSDSNSAADLLH (SEQ ID No. 122) K:GYDHSDSNSAADLLH (SEQ ID No. 146) |
| BA | K:GFTFSNYFIH (SEQ ID No. 144) K:GFPFSRYSMH (SEQ ID No. 147) | K:TISGRTKYMFYSDSLRG (SEQ ID No. 145) K:SMTSRTNHKYYADSLKG (SEQ ID No. 148) | K:GYDHSDSNSAADLLH (SEQ ID No. 146) K:GYDTSGSDSGVDFQY (SEQ ID No. 149) |

| | $V_L$ CDR1 | $V_L$ CDR2 | $V_L$ CDR3 |
|---|---|---|---|
| 2A6 | I:SGSVASHY (SEQ ID No. 132) K:VRSSGSVASHYVQ (SEQ ID No. 156) | I:EDS (SEQ ID No. 133) K:EDSHRPS (SEQ ID No. 157) | I:QSYYGNNQVL (SEQ ID No. 134) K:QSYYGNNQVL (SEQ ID No. 134) |
| 2B6 | I:RGYIASYY (SEQ ID No. 135) K:TRGRGYIASYYVQ (SEQ ID No. 158) | I:EDT (SEQ ID No. 136) K:EDTQRPS (SEQ ID No. 159) | I:QSYDDANHVI (SEQ ID No. 137) K:QSYDDANHVI (SEQ ID No. 137) |
| 2A6_AI | I:SGSVASHY (SEQ ID No. 132) K:VRSSGSVASHYVQ (SEQ ID No. 156) | K:EDS (SEQ ID No. 133) K:EDSHRPS (SEQ ID No. 157) | I:QSYYGNNQVL (SEQ ID No. 134) K:QSYYGNNQVL (SEQ ID No. 134) |

TABLE 8-continued

```
2A6_QI:SGSVASHY       K:EDS            I:QSYYGNNQVL
    (SEQ ID No. 132)  (SEQ ID No. 133) (SEQ ID No. 134)
    K:VRSSGSVASHYVQ   K:EDSHRPS        K:QSYYGNNQVL
    (SEQ ID No. 156)  (SEQ ID No. 157) (SEQ ID No. 134)

BA     I:SGSVASHY     I:EDS            I:QSYYGNNQVL
    (SEQ ID No. 132)  (SEQ ID No. 133) (SEQ ID No. 134)
    K:VRSSGSVASHYVQ   K:EDSHRPS        K:QSYYGNNQVL
    (SEQ ID No. 156)  (SEQ ID No. 157) (SEQ ID No. 134)
```

Example 4: Determination of Characteristics of IFNγ Antibodies in Binding to and Blocking IFNγ

This Example illustrates the functional characteristics of IFNγ binding and blocking of the IFNγ antibodies of the present disclosure in a variety of standard assays.

A. Bio-Layer Interferometry (BLI) Analysis.

Materials and methods: Antibody-binding kinetic rate constants ($k_a$ and $k_d$) were measured by Bio-Layer Interferometry (BLI, ForteBio Octet RED96). The BLI assay was performed using AHC (Anti-hIgG Fc Capture) biosensors (ForteBio) to capture each IFNγ antibody (750 ng/mL) to acquire a 0.5 nm shift and then the biosensors were dipped into varying concentrations (i.e. 0, 0.625, 1.25, 2.5, 5, 10, 20 and 40 nM) of recombinant human IFNγ protein (R&D systems, 285-IF-100) in running buffer containing 0.1% bovine serum albumin (BSA), 0.1% Tween-20, 250 mM NaCl, 2.7 mM KCl, 10 mM $Na_2HPO_4$ and 1.8 mM $KH_2PO_4$ in sterile water. Rate constants were calculated by curve fitting analyses (1:1 Langmuir model) of binding response with a 5-minute association and 15-minute dissociation interaction time.

Results:

Typical binding curves were obtained by passing different concentrations of recombinant human IFNγ (0, 0.625, 1.25, 2.5, 5, 10 nM) over the IFNγ antibody immobilized on the AHC biosensor. The observed IFNγ antibody binding kinetic rate constants ($K_a$ and $K_d$), as well as the equilibrium dissociation constant ($K_D=K_d/K_a$) are displayed in Table 9. The IFNγ antibodies, 2A6, and 2B6, each has a KD value $<10^{-10}$ M, indicating high affinity to human IFN-γ.

TABLE 9

| mAb | $K_a$ (1/Ms) | $K_d$ (1/s) | $K_D$ (M) |
| --- | --- | --- | --- |
| 2A6 | $1.08 \times 10^6$ | $3.97 \times 10^{-5}$ | $3.68 \times 10^{-11}$ |
| 2B6 | $1.48 \times 10^6$ | $1.08 \times 10^{-4}$ | $7.31 \times 10^{-11}$ |
| 1E8 | $4.64 \times 10^5$ | $1.21 \times 10^{-4}$ | $2.61 \times 10^{-10}$ |
| 2F2 | $3.44 \times 10^5$ | $1.09 \times 10^{-4}$ | $3.17 \times 10^{-10}$ |

In another experiment, the IFNγ antibodies, AMG811 (described in U.S. Pat. No. 7,335,743 and was prepared as described therein), 2A6, 2B6, 2A6_A, 2A6_Q, AB, and BA were assayed for IFNγ binding as described above. As shown in Table 10, these IFNγ antibodies all exhibit comparable IFN-γ binding function with KD values $<10^{-10}$ M.

TABLE 10

| mAb | $K_a$ (1/Ms) | $K_d$ (1/s) | $K_D$ (M) |
| --- | --- | --- | --- |
| AMG811 | $2.48 \times 10^6$ | $8.59 \times 10^{-5}$ | $3.47 \times 10^{-11}$ |
| 2A6 | $2.61 \times 10^6$ | $4.90 \times 10^{-5}$ | $1.87 \times 10^{-11}$ |
| 2B6 | $3.13 \times 10^6$ | $5.40 \times 10^{-5}$ | $1.72 \times 10^{-11}$ |
| 2A6_A | $2.32 \times 10^6$ | $5.17 \times 10^{-5}$ | $2.23 \times 10^{-11}$ |
| 2A6_Q | $2.41 \times 10^6$ | $5.23 \times 10^{-5}$ | $2.17 \times 10^{-11}$ |
| AB | $2.19 \times 10^6$ | $5.46 \times 10^{-5}$ | $2.50 \times 10^{-11}$ |
| BA | $2.76 \times 10^6$ | $1.31 \times 10^{-4}$ | $4.75 \times 10^{-11}$ |

B. HLA-DR Expression.

Materials and Methods:

$2 \times 10^5$ THP-1 cells (BCRC 60430) were cultured in 100 μL of Roswell Park Memorial Institute (RPMI)-1640 medium (Gibco, 11875-093) supplemented with 10% FBS and 1% penicillin/streptomycin, and then treated with different concentrations (i.e. 0.017, 0.05, 0.15, 0.45, 1.37, 4.11, 12.34, 37.03, 111.1, 333.3, 1000, 3000, 5000 and 10000 ng/mL) of the IFNγ antibodies, 2A6, and 2B6 for 30 min. The treated THP-1 cells were stimulated with 2 ng/mL recombinant human IFN-γ protein and cultivated in an incubator (37° C., 5% $CO_2$) for 24 hours. The un-stimulated THP-1 cells were used as control. Thereafter, the stimulated and un-stimulated THP-1 cells were stained with HLA-DR-PE antibody (BD Pharmigen™) and then placed for 30 minutes on ice in the dark. The stained cells were washed with 2 mL of PBS and resuspended in 500 μL of PBS. The fluorescence intensity of the stained cells was acquired with a FACSVerse flow cytometer and analyzed with FACSuite software. The inhibition percentage of HLA-DR expression for each antibody is obtained by the following formula:

$A=(B/C) \times 100$ where A=Inhibition percentage of HLA-DR expression; B=the median value of the fluorescence intensity for the stimulated cells; C=the median value of the fluorescence-intensity for the unstimulated cells.

Results:

The tested IFN-γ antibodies 2A6, and 2B6 exhibited dose-dependent inhibition of HLA-DR expression. The $IC_{50}$ (ng/mL) values were determined for 2A6, and 2B6 were 3.4, and 3.5, respectively. The above results indicated that the antibodies of the present disclosure can effectively inhibit IFN-γ mediated activity and could be used in the treatment of IFN-γ mediated syndromes.

C. ELISA Assay of IFNγ Antibodies.

Materials and Methods:

A clear polystyrene 96-well, flat-bottomed plate (Nunc) was coated with 100 μL of recombinant human IFN-γ protein (2 μg/mL) or BSA (2 μg/mL) in bicarbonate buffer (pH 9.6) per well and incubated at 4° C. overnight. The plate was washed three times using phosphate-buffered saline (PBS) with 0.05% Tween 20 and then blocked with 5% human normal serum albumin (Aventis) in PBS for 2 hours at 25° C. The plate was washed again using PBS with 0.05% Tween 20, after which each of the IFNγ antibodies, 1E8, 2F2, 2A6, 2B6, AB and BA, in two different concentrations of 1 μg/mL and 0.1 μg/mL were added into the wells of the plate for binding with the recombinant human IFN-γ protein, followed by reaction at 25° C. for 2 hours. The plate was thoroughly washed using PBS with 0.05% Tween 20, and then Fc-specific alkaline phosphatase-conjugated AffiniPure Goat anti-human IgG (Cappel) was added at a dilution ratio of 1:2500. The plate was placed for 90 minutes at 37° C. and then washed five times using PBS with 0.05% Tween 20. After adding p-Nitrophenyl phosphate (pNPP) solution (100 µL/well), the plate was placed at 37° C. for 30 minutes. Absorbance was determined at $OD_{405}$ nm with a VICTOR X3 Multilabel Plate Reader (PerkinElmer).

Results:

The absorbance at 405 nm ($OD_{405}$) of the plate wells showed that all of the tested IFNγ antibodies at higher concentration (1 µg/mL) displayed stronger absorbance than at the lower concentration (0.1 µg/mL). Additionally, the IFNγ antibodies were not bound to the BSA, indicating that they specifically bind to human IFNγ.

D. ELISA Assay of Anti-IFN-γ Antibody Using Biotinylated IFN-γ.

Materials and Methods:

Recombinant human IFNγ (R&D systems 285-IF-100) and Cynomolgus IFNγ (R&D systems 961-RM-025) were biotinylated according to kit manual (EZ-Link NHS-LC-Biotin; Thermo #21336) and bound to streptavidin coated plates, respectively. After incubating at room temperature for 1-2 hours, the plates were washed three times with 300 µL wash buffer. Serial dilutions of IFNγ antibodies, AMG811, 2A6, 2A6A, 2A6Q, 2B6, AB, and BA, were added to wells. After incubation at room temperature for 1-2 hours, the plates were washed three times with 300 µL wash buffer. HRP anti-Human IgG was applied to each well at room temperature for 1-hour incubation. After washing, the plates were developed with TMB substrate, and analyzed under $OD_{450-650}$.

Figure 3A:
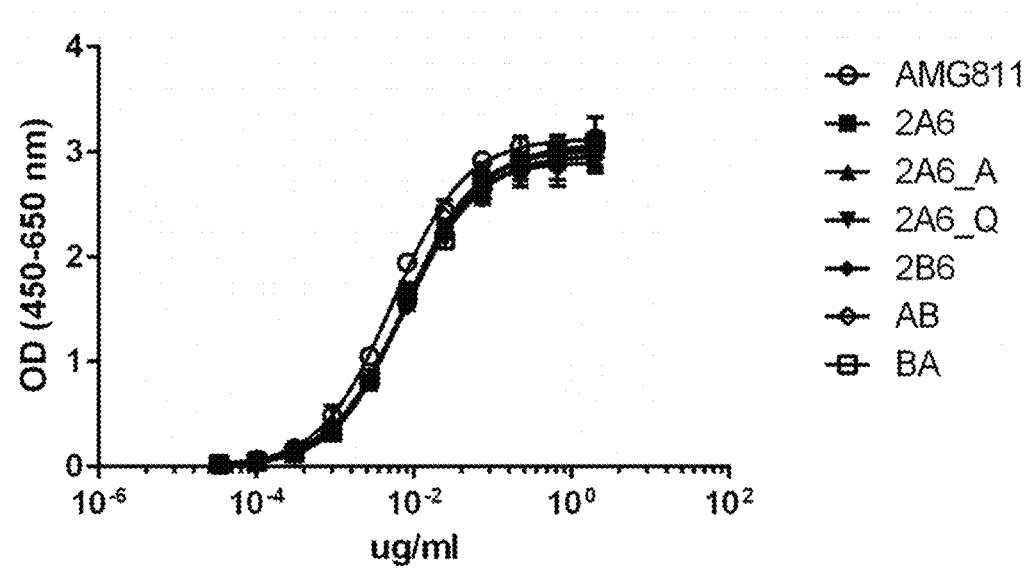
FIG. 3A and FIG. 3B depict ELISA assay results for IFNγ antibody binding to human and rhesus macaque/cynomolgus IFNγ shown.
Figure 3B:
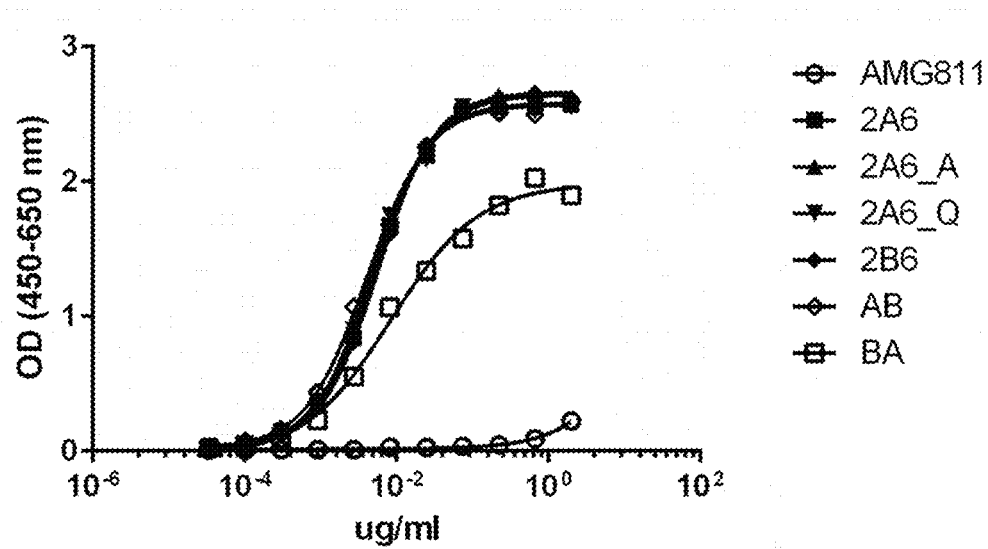

Results:

As shown in FIG. 3A, all of the tested IFNγ antibodies exhibited strong binding affinity to human IFNγ. As shown in FIG. 3B, the IFNγ antibodies, 2A6, 2A6A, 2A6Q, 2B6, AB, and BA also exhibited cross-reactivity with rhesus macaque/cynomolgus IFNγ although with a lower affinity than their binding to human IFNγ. AMG811, however, did not exhibit cross-reactivity with rhesus macaque/cynomolgus IFNγ.

E. Cell-Based Assay of IFN-γ Neutralizing Activity.

Materials and Methods:

A Luciferase Reporter HeLa Stable Cell Line expressing pGL4[luc2P/GAS-RE/Hygro (Promega # CS179301) was used to measure neutralizing activity of the IFNγ antibodies, AMG811, 2A6, 2A6A, 2A6Q, 2B6, and BA. Briefly, HeLa cell line was plated in 96-well white plates at $8 \times 10^3$ cells/well. Cells were treated with 1 ng/ml IFNγ and different concentrations of the IFNγ antibody for 18 h. Luciferase activity was analyzed using ONE-Glo™ Luciferase Assay System (Promega # E6110).

Results:

As shown in FIG. 4, all of the tested IFNγ antibodies were able to neutralize the activity of IFNγ, indicating sufficient neutralizing activity for industrial or pharmaceutical application.

F. Whole Blood Assay of IFNγ Antibody Neutralizing Activity.

Materials and Methods:

Whole blood from healthy volunteers who had been vaccinated with *Bacillus* Calmette-Guérin (BCG) was collected in 10-mL heparinized tubes. 20-µL samples of the whole blood were added to 80 µL of RPMI 1640 culture medium with or without BCG+IL12 (20 ng/ml) in round-bottom wells of a 96-well microtiter plate. Anti-IFNγ antibody was added to culture at 1 µg/ml before BCG+IL12. The microtiter plate was incubated at 37° C., 5% $CO_2$ for 48 h. Following incubation, CXCL9 was measured using CXCL9 ELISA kit (R&D systems DCX900). CXCL10 was measured using CXCL10 ELISA kit (Biolegend 439905). Cytokine levels were presented after correction with the dilution factor. Human IgG1 isotype control was used in the experiment as a negative control. As expected, the human whole blood samples produced high levels of IFNγ, as well as CXCL9 and CXCL10, whose production is known to be regulated by IFNγ. Inhibition of the endogenous IFNγ activity by an IFNγ antibody would also block production of CXCL9 and CXCL10.

Figure 5A:
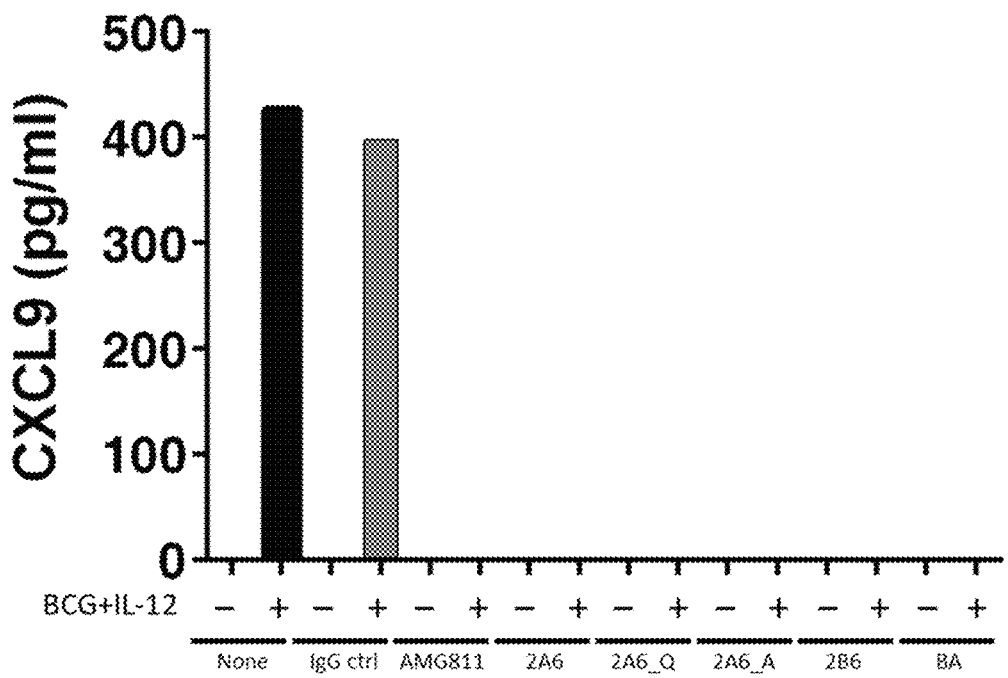
FIG. 5A and FIG. 5B depicts assay results for IFNγ neutralizing activity of IFNγ antibodies in a whole blood assay.
Figure 5B:
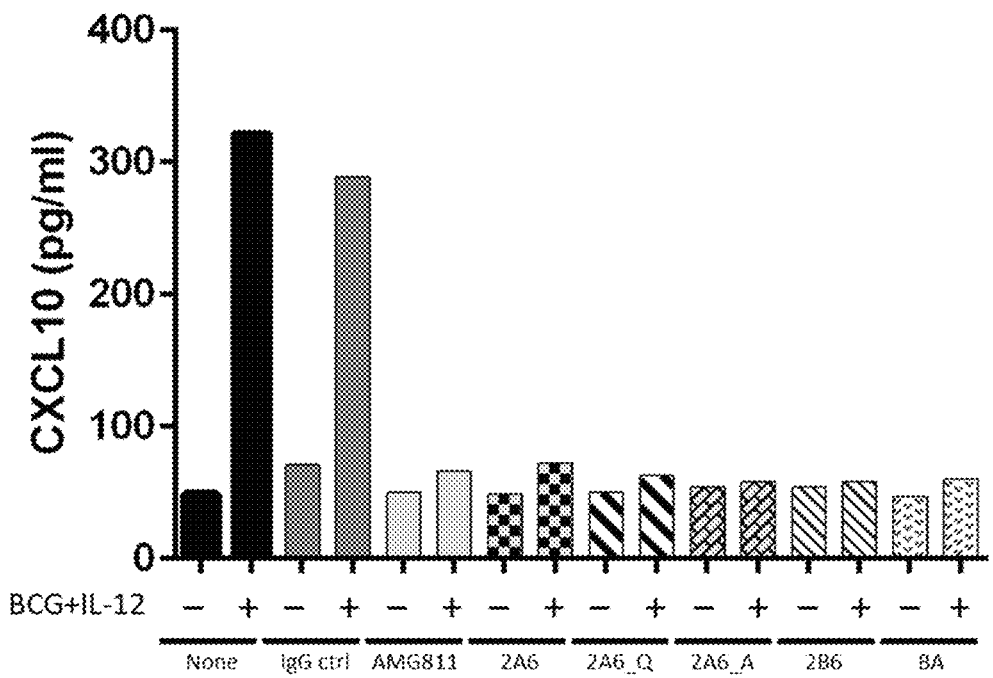

Results:

As shown by the results depicted in FIG. 5A and FIG. 5B, the IFNγ antibodies, AMG811, 2A6, 2A6A, 2A6Q, 2B6, and BA, effectively inhibited the production of CXCL9 and CXCL10 by neutralizing the endogenous IFN-γ.

Example 4: THP-1 Cell-Based Study of IFNγ Antibody Neutralizing Effect on Expression of TCIRs Prolonged IFNγ signaling has previously been shown to induce the expression of ligands of T-cell inhibitory receptors (TCIR) including the ligands of PD-1 (PD-L1), TIM3 (Galectin-9) and LAGS (MHC Class II) (see e.g., Benci et al., Cell. 2016 Dec. 1; 167(6):1540-1554). This induction leads to resistance to immune checkpoint blockade and exhausted T cells.

This example illustrates a cell-based model study demonstrating the neutralizing effect of IFNγ antibodies on the expression of TCIR ligands, HLA-DR and PD-L1.

Materials and Methods:

THP-1 cells were cultured according to ATCC instructions. For neutralizing assay, 40 ng/ml IFNγ in 500 µL of RPMI-1640 was incubated with different amounts (0, 80, 400, 2000 ng/ml) of six different IFNγ antibodies ("AMG811," "BA", "2A6," "2A6_A," "2A6_Q," "2B6") for 10 mins, and the mixture was added to $4 \times 10^5$ cells (500 ul). After incubation for 72 h in an incubator at 37° C., cells were stained with PE anti-human PD-L1 Antibody (Biolegend 329706) or FITC anti-human HLA-DR Antibody (Biolegend 327006) and incubated for 30 mins on ice in the dark. The cells were washed with 2 ml of FACS buffer twice and resuspended in 300 µl of FACS buffer. Data were acquired with a FACSCalibur flow cytometer.

Figure 6A:
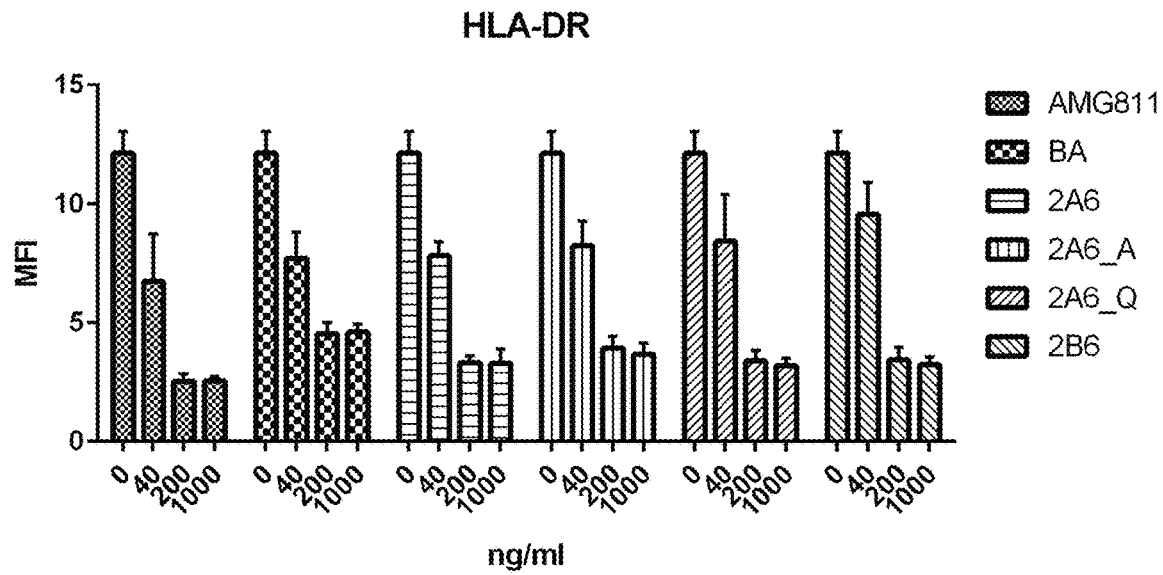
FIG. 6A and FIG. 6B depicts assay results for IFNγ neutralizing activity of IFNγ antibodies in a cell-based dose-dependence study of inhibition of expression of the TCIR ligands HLA-DR and PD-L1.
Figure 6B:
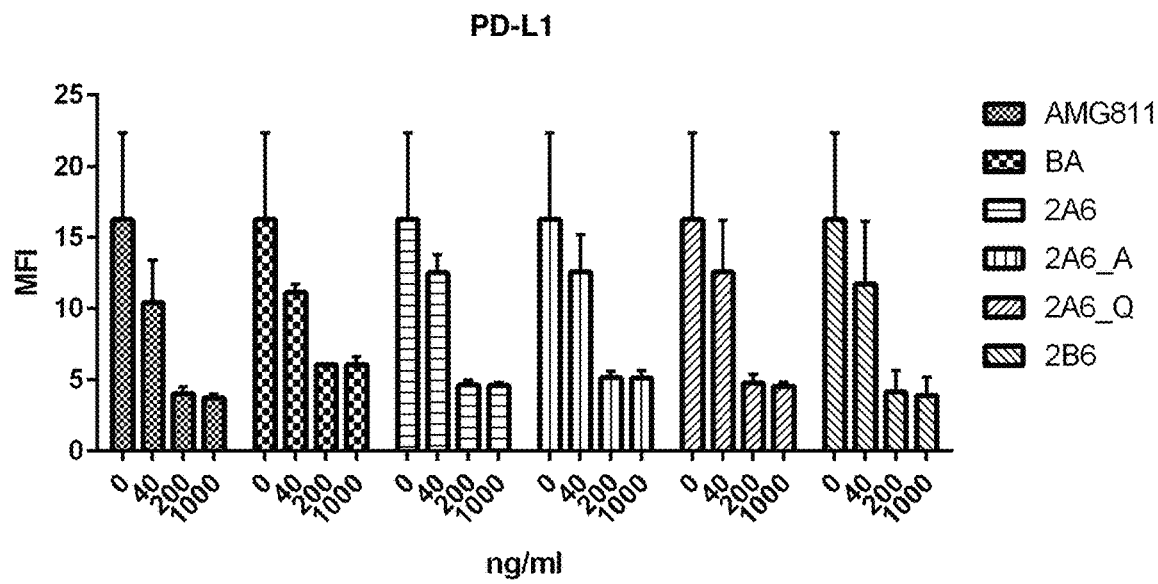

Results:

As shown in FIG. 6A and FIG. 6B, THP-1 cells stimulated with IFNγ express TCIR ligands, HLA-DR and PD-L1. However, upon treatment of the THP-1 cells with any of the six neutralizing IFNγ antibodies, AMG811, BA, 2A6, 2A6_A, 2A6_Q, or 2B6, THP-1 cells exhibited significant reductions in the expression of TCIRs ligands. Moreover, the IFNγ antibodies induced a dose-dependent response in the reduction of HLA-DR and PD-L1 expression.

Example 5: THP-1 Cell-Based Study of Neutralizing Effect of IFNγ Antibodies on IDO Activity Indoleamine 2,3-dioxygenase (IDO) has previously been shown to be upregulated in response to inflammatory signals generated by activated effector T cells, such as IFNγ inducing T cell exhaustion (see e.g., Munn et al., J Clin Invest. 2007 May 1; 117(5): 1147-1154; Munn et al., J Exp Med.

2013 Jul. 1; 210(7):1389-1402; Munn et al., Cell Rep. 2015 Dec. 22; 13(11):2470-2479). IDO inhibits effector T cells and activates Tregs to further contribute to an immunosuppressive microenvironment. By suppressing T cells and enhancing local Treg-mediated immunosuppression, increased IDO expression facilitates a tolerogenic milieu.

This example illustrates a cell-based model study demonstrating the neutralizing effect of IFNγ antibodies on the IFNγ induced indoleamine 2,3-dioxgenase (IDO) activity in THP-1 cells.

Materials and Methods:

THP-1 cells were cultured according to ATCC instructions. $3 \times 10^6$ cells were seeded in 4 mL of medium supplemented with 10% FBS and 1% penicillin/streptomycin. Cells were stimulated 0, 10, 20 ng/ml of IFNγ for 48 hours. For neutralizing assay, IFNγ was first incubated with the anti-IFNγ mAbs, 2A6_Q or 2B6, before adding to the cells. The final concentration of anti-IFNγ mAb in the culture was 2 μg/mL. After incubation for 48 h at 37° C., cells were harvested and lysed in 150 μl lysis buffer according to the manual of IDO1 Activity Assay Kit. The IDO activity of lysate was determined using IDO Activity Assay Kit (Biovision K972). Data of IDO activity were analyzed with the Student's t-test.

Figure 7:
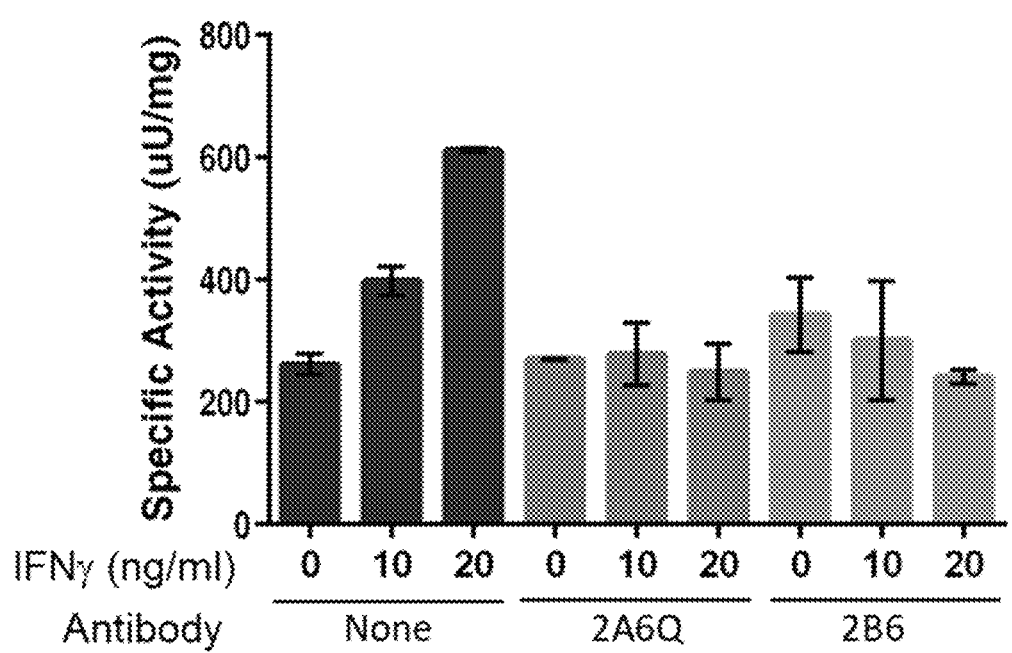
FIG. 7 depicts assay results for IFNγ neutralizing activity of IFNγ antibodies against indoleamine 2,3-dioxgenase (IDO) activity in THP-1 cells

Results:

As shown in the FIG. 7, stimulation of THP-1 cells with increasing amounts of IFNγ (0, 10 or 20 ng/mL) resulted in increasing amounts of IDO specific activity. However, further treatment of the THP-1 cells with the neutralizing IFNγ antibodies, 2A6_Q or 2B6, effectively reduced the IDO specific activity to approximately the level observed without any IFNγ stimulation.

Example 6: IFNγ Blocking Effect of IFNγ Antibodies in HeLa-GAS Cell Line Assay

This example illustrates the IFNγ blocking effect of IFNγ antibodies in an IFNγ-activated-site (GAS) luciferase reporter HeLa cell assay. The HeLa-GAS luciferase reporter cell assay utilizes is a stably transfected HeLa cell line which expresses luciferase reporter under the transcriptional control of an IFNγ activation site.

Materials and Methods:

IFNγ antibodies, 2A6, 2B6, 2A6Q, and 2C10 were prepared as described in Example 3. The disclosed gene sequences encoding IFNγ antibodies, NI0501 (U.S. Pat. No. 7,700,098), Fontolizumab (U.S. Pat. No. 632,951), and AMG811 (U.S. Pat. No. 7,335,743) were synthesized and cloned into human expression vector. A stable HeLa reporter cell line (HeLa-GAS) that expressed pGL4[luc2P/GAS-RE/Hygro] vector (CS179301; Promega Corporation, Madison, Wis., USA) was generated. The HeLa-GAS cells were plated and grown at 8000 cells/well in a 96-well culture plate. A serial dilution of the six antibodies was prepared in the presence IFNγ. 100 μL of IFNγ antibody/IFNγ mixture was added to the pre-plated cells resulting in stimulation of the HeLa-Gas cells with 1 ng/mL IFNγ. After incubation for 18 h, ONE-Glo™ Reagent (Promega Corporation, Madison, Wis., USA) was added to each well with another 3 minutes of incubation. Then luminescence was measured using a luminometer (Victor X3, PerkinElmer).

Figure 8:
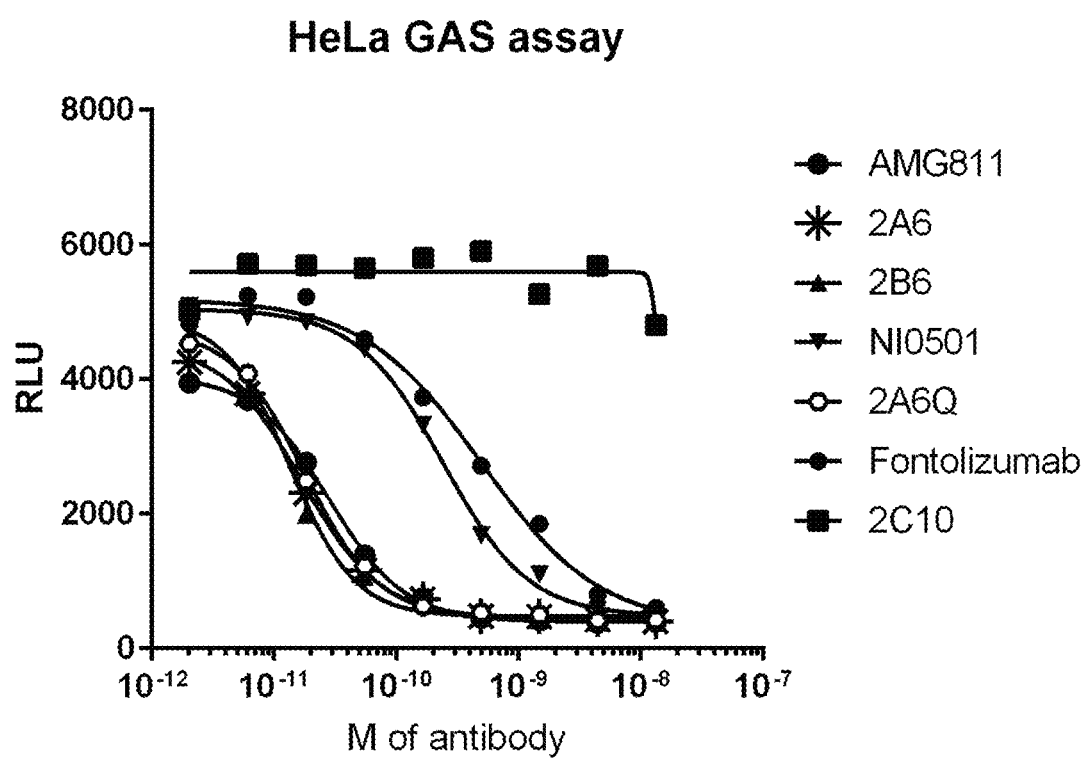
FIG. 8 depicts results for the IFNγ blocking effect of IFNγ antibodies in an IFNγ-activated-site (GAS) luciferase reporter HeLa cell assay.

Results:

As shown in FIG. 8, all six tested IFNγ antibodies, 2A6, 2B6, 2A6Q, NI0501, Fontolizumab, and AMG811, which are known to specifically bind to and neutralize IFNγ, significantly decreased relative luminometer units (RLU) in a dose-dependent manner. In contrast, 2C10, which an IFNγ antibody also obtained by single B cell cloning from dNTM patients (like 2A6, 2B6, and 2A6Q) but which does not exhibit IFNγ neutralizing activity in various assays (data not shown), was found to exhibit no effect on the RLU.

Example 7: IFNγ Blocking Effect of IFNγ Antibodies in MLR Assay

This example illustrates the effects of the IFNγ antibodies of the present disclosure when added to a one-way allogeneic mixed lymphocyte reaction (MLR) culture.

Materials and Methods:

Selected IFNγ antibodies, 2A6Q, AMG811, and NI0501, that have been shown to block IFNγ signaling in various cell-based assays (see above Examples) were added to a one-way allogeneic MLR system. PBMCs from healthy volunteer donors were isolated by density gradient centrifugation using Ficoll-Hypaque. $2 \times 10^5$ human PBMCs were incubated with an equal number of mitomycin C-treated (30 μg/mL, 30 min) stimulator cells per well in 96-well plate. The tested MLR cultures included the IFNγ antibody, AMG811, 2A6_Q, or NI0501, at 5 μg/mL, or IgG1 control antibody (Bio X cell: 6E0297) at 5 μg/mL. Responder cell proliferation was measured at day 9 by CellTiter-Glo® assay (G7570; Promega Corporation, Madison, Wis., USA). Luminescence was measured by a luminometer (Victor X3, PerkinElmer).

Results: As shown by the plots for two representative assays of healthy donor cells depicted in FIG. 9, the presence of any of the IFNγ antibodies AMG811, 2A6Q, or NI0501 in MLR culture, when compared to control IgG, significantly enhanced proliferation of responder cells, indicating increased immune activation.

Example 8: IFNγ Blocking Effect of IFNγ Antibodies on Immune Response in SEB-Stimulated Human PBMCs This example illustrates the effects of the IFNγ antibodies of the present disclosure on the immune response of human PBMCs when stimulated by Staphylococcal enterotoxin B (SEB).

Materials and Methods:

PBMCs obtained from healthy adult donors were stimulated with 1 ng/mL SEB in the presence of one of the IFNγ antibodies shown to neutralize IFNγ, AMG811, 2A6Q, 2B6, or NI0501, the non-neutralizing antibody, 2C10, or control IgG.

PBMCs were isolated from healthy volunteers using Ficoll-Paque density gradient centrifugation, and rest in 10% RPMI medium with 5% FBS for 24 hours. PBMCs ($2 \times 10^5$ cells/per well) were seeded in 200 μL assay medium (RPMI, 5% human serum) with 1 ng/mL SEB in the presence of one of the IFNγ antibodies shown to neutralize IFNγ, AMG811, 2A6Q, 2B6, or NI0501, the non-neutralizing antibody, 2C10, or control IgG. IL-2 levels in culture supernatants were measured after Day 2 by IL-2 ELISA kit (Biolegend, San Diego, Calif., USA) according to manufacturer's instruction. Cell proliferation was determined at Day 7 using CellTiter-Glo® (Promega Corporation) and luminescence was measured by a Victor™ 1420 multilabel counter (PerkinElmer Corp. US). Data were analyzed using GraphPad Prism7 software.

Figure 10A:
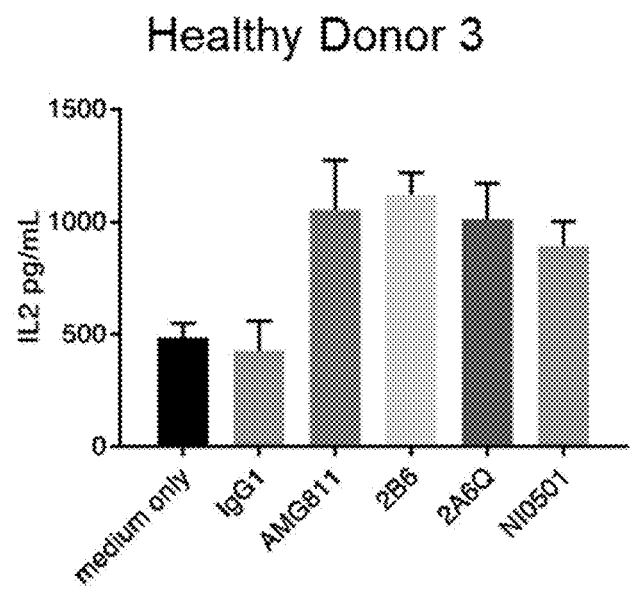
FIG. 10A and FIG. 10B depict plots of results for IFNγ neutralizing activity of IFNγ antibodies against an SEB stimulated immune response in PBMCs.
Figure 10B:
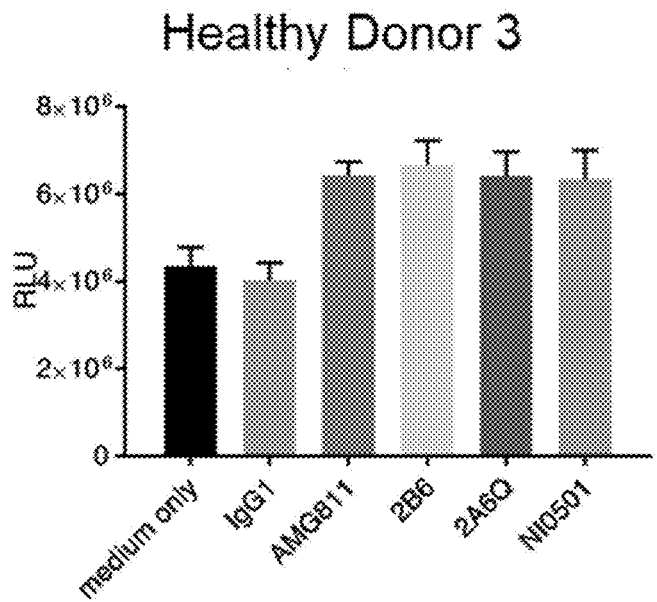

Results:

As shown in FIG. 10A, the IFNγ neutralizing IFNγ antibodies AMG811, 2B6, 2A6Q, and NI0501, elicited significantly enhanced IL-2 secretion at Day 2. Additionally, as shown in FIG. 10B, the IFNγ neutralizing IFNγ antibodies AMG811, 2B6, 2A6Q, and NI0501, elicited increased cell proliferation as measured at Day 7. In contrast, the control IgG, did not elicit an enhanced immune response at Day 2 or 7. The non-neutralizing antibody, 2C10, also did not enhance IL-2 secretion relative to the control IgG (data not shown).

Example 9: Flow Cytometry Assay of IFNγ Antibody Effect on T-Cell Proliferation in SEB-Stimulated Human PBMCs This example illustrates the effects of the IFNγ antibodies of the present disclosure on T cell proliferation during SEB stimulation of human PBMCs as measured using flow cytometry.

Materials and Methods:
CFSE-labeled PBMCs were stimulated with SEB (1 ng/mL) in the presence of the IFNγ antibody, 2A6Q or AMG811, an anti-PD-1 antibody, or IgG control antibody, according to method described in Example 8. After 6 days of culture, the cells were stained for CD4 and CD8 and the percentage of CFSE-diluted CD4+ or CD8+ T cells were determined by flow cytometry.

Figure 11:
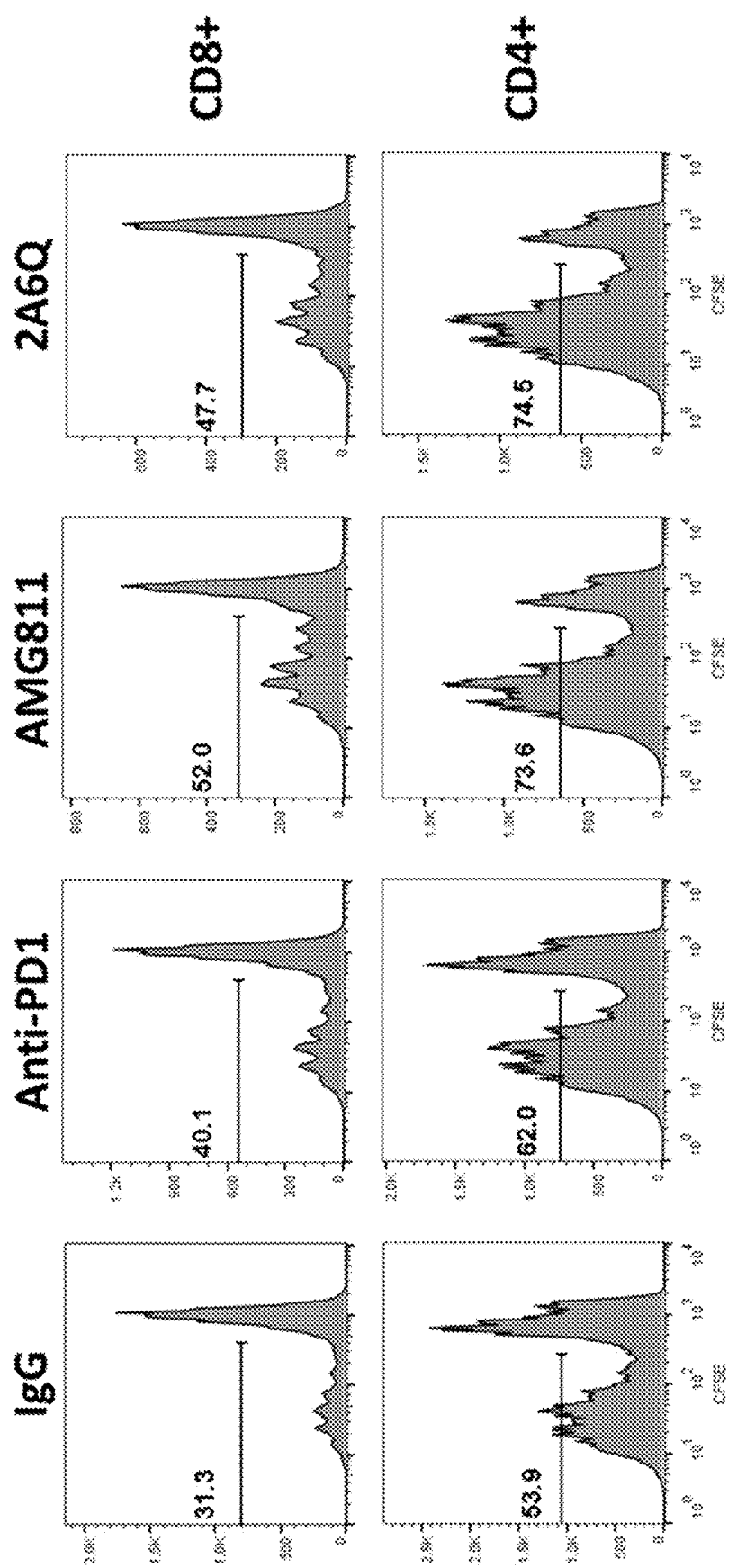
FIG. 11 depicts flow cytometry histograms of SEB-stimulated PBMCs treated with IFNγ antibodies that show results of enhanced proliferation of CFSE-labeled $CD4^+$ and $CD8^+$ T cells.

Results:
FIG. 11 depicts representative flow cytometry histograms, each from a single donor, that demonstrate the enhanced proliferation of CFSE-labeled CD4+ and CD8+ T cells were shown. The diagrams are representative from three experiments. As illustrated by the diagrams of FIG. 11, the percentage of proliferating (CFSE-diluted) cells were significantly enhanced by the presence of the IFNγ blocking antibodies, AMG811 and 2A6Q, relative to the control IgG. Included as a positive control, the PD-1 blocking antibody, which is known to increase T cell proliferation, also resulted in significant enhancement of proliferating cells relative to control. No population of CFSE-diluted cells was observed in histograms from control experiment conducted with no SEB stimulation (data not shown).

Example 10: IFNγ Blocking Effect of IFNγ Antibody on PD-L1 Expression in SEB-Stimulated Human PBMCs and B Cells PD-L1, the ligand for PD1, is understood to have an important major role in suppressing the adaptive arm of the immune system including during autoimmune disease and other disease states such as hepatitis. PD-L1 expression on T cells is known to increase in response to IFNγ stimulation. This example illustrates the effect of the IFNγ antibody of the present disclosure in blocking PD-L1 expression on human PBMCs and B cells.

Materials and Methods:
PBMCs and B cells were isolated from a healthy donor (i.e., no HBV infection). The PBMCs comprise different immune cells capable of expressing PD-L1. The isolated PBMCs and B cells were stimulated with 1 ng/mL SEB for 3 days in the presence of the IFNγ blocking antibody 2A6Q, the non-IFNγ-neutralizing antibody, 2C10, and the IgG1 control antibody. Cells were harvested, and cell surface expression of PD-L1 was measured using flow cytometry. Results were plotted as the geometric mean fluorescent intensity (GMFI).

Figure 12A:
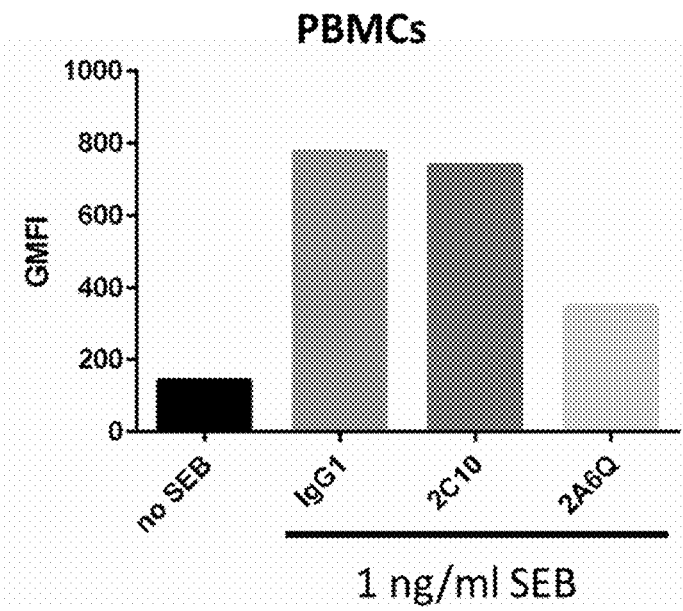
FIG. 12A and FIG. 12B depicts results for the IFNγ neutralizing effect of the IFNγ antibodies on PD-L1 expression of human PBMCs and B cells.
Figure 12B:
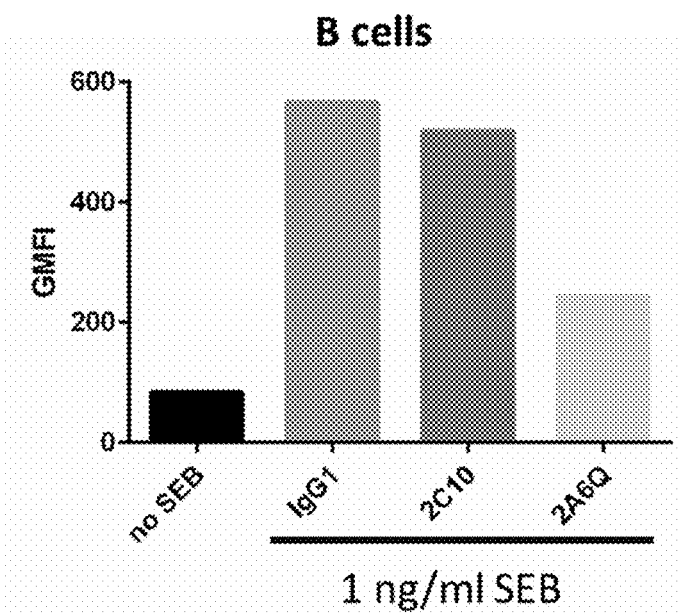

Results:
As shown in FIG. 12A and FIG. 12B, the total expression of PD-L1 on the PBMCs and B cells was upregulated due to the SEB stimulation. The presence of the IFNγ neutralizing antibody, 2A6Q, however greatly inhibited the PD-L1 expression in both the PBMCs and B-cells. The presence of the IFNγ non-neutralizing antibody, 2C10, however, did not inhibit PD-L1 expression significantly relative to the IgG1 control.

Example 11: Improved Immune Response of IFNγ Blocking Effect in Combination with PD-1 or CTLA-4 Blockade This example illustrates how an improved immune response is elicited in SEB-stimulated cells by IFNγ antibodies of the present disclosure used in combination with CTLA-4 or PD-1 blocking antibodies.

Materials and Methods:
PBMCs obtained from healthy adult donors were stimulated with 1 ng/mL SEB in the presence of 10 μg/mL of the following antibody or antibody combinations: IgG1 control antibody, 2C10, 2A6Q, AMG811, anti-PD1, anti-CTLA4, [2A6Q+anti-PD1], [2A6Q+anti-CTLA4], [AMG811+anti-PD1], or [AMG811+anti-CTLA4]. IL-2 secretion was determined at day 2 by IL-2 ELISA kit (Biolegend 431804). Genes encoding anti-PD-1 (Pembrolizumab), anti-PD-L1 (Atezolizumab), and anti-CTLA4 (Ipilimumab) (available at e.g., www.imgt.org/3Dstructure-DB) were synthesized, cloned into human vector, expressed, and purified using standard techniques for generating recombinant antibodies.

Figure 13A:
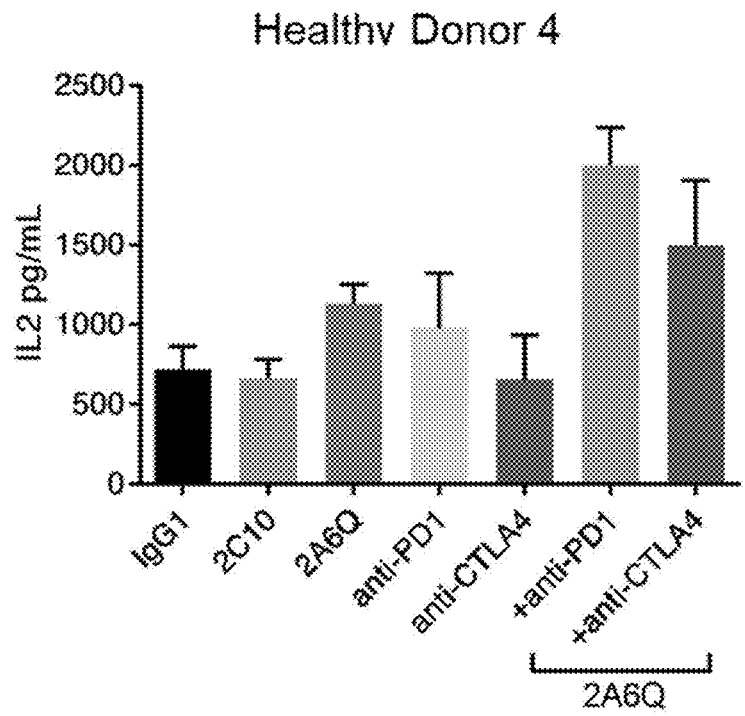
FIG. 13A and FIG. 13B depict results for the enhanced immune response elicited in SEB-stimulated cells from two different healthy donors samples by the IFNγ antibodies used in combination with CTLA-4 or PD-1 blocking antibodies.
Figure 13B:
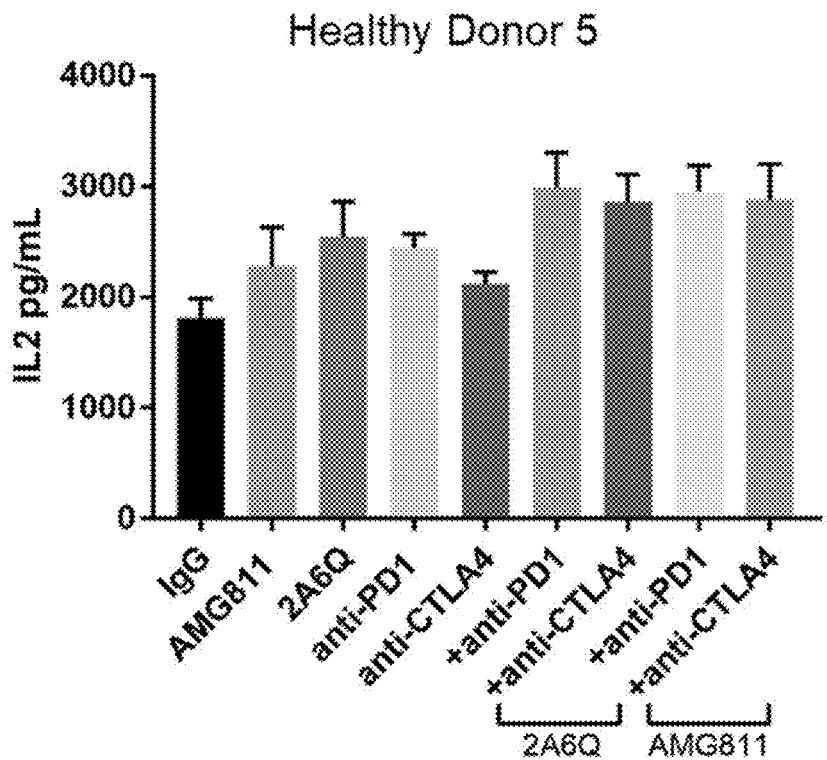

Results:
As shown in FIG. 13A and FIG. 13B, the presence of 2A6Q, AMG811 or anti-PD1 antibody alone (at 10 μg/mL concentration) significantly enhanced the T cell response as indicated by IL-2 concentration. Anti-CTLA4 antibody, however, did not effectively enhance T cell response when used alone. Surprisingly, the combinations of one of the IFNγ blocking antibodies, AMG811 or 2A6Q with an anti-CTLA4 antibody or an anti-PD-1 antibody resulted in increased enhancement of the immune response in PBMCs from healthy donors when compared to the response with the lone antibodies.

Example 12: IFNγ Blocking Effect on SEB-Induced Immune Response in PBMCs from Patients with Chronic HBV Infections This example illustrates how IFNγ antibodies used in combination with CTLA-4 or PD-1 blocking antibodies elicit an improved immune response SEB-stimulated PBMCs from patients with chronic HBV infections.

Materials and Methods:
PBMCs obtained from patients with chronic HBV infection were stimulated with 1 ng/mL SEB in the presence of 10 μg/mL of the following antibody or antibody combinations: IgG1 control antibody, 2C10, 2A6Q, AMG811, NI0501, anti-PD1, anti-PDL1, anti-CTLA4, [2A6Q+anti-PD1], [2A6Q+anti-PDL1], [2A6Q+anti-CTLA4], [NI0501+anti-PD1], [NI0501+anti-PDL1], or [NI0501+anti-CTLA4]. FIG. 14 depicts plots of representative results from two different chronic HBV patients.

Figure 14A:
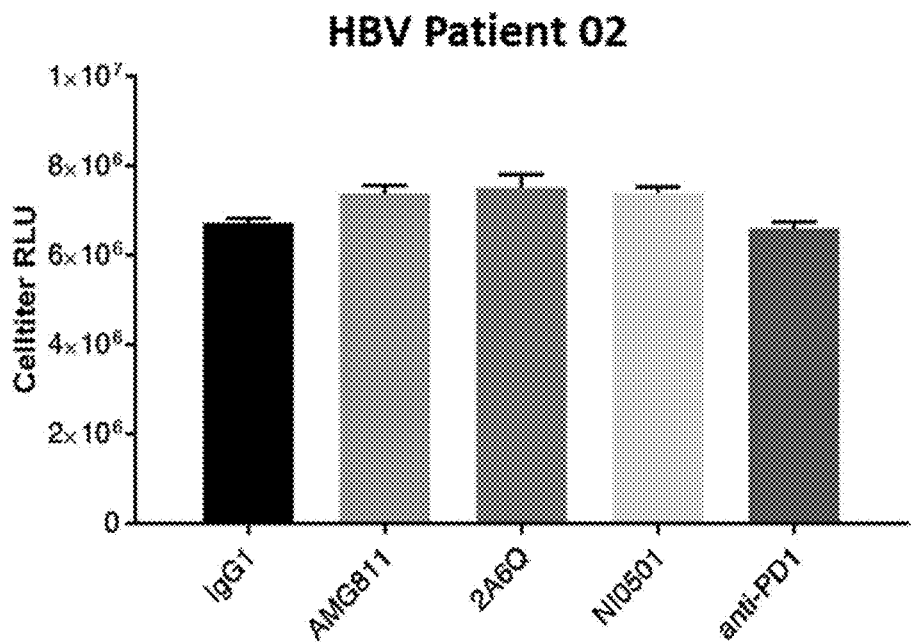
Figure 14B:
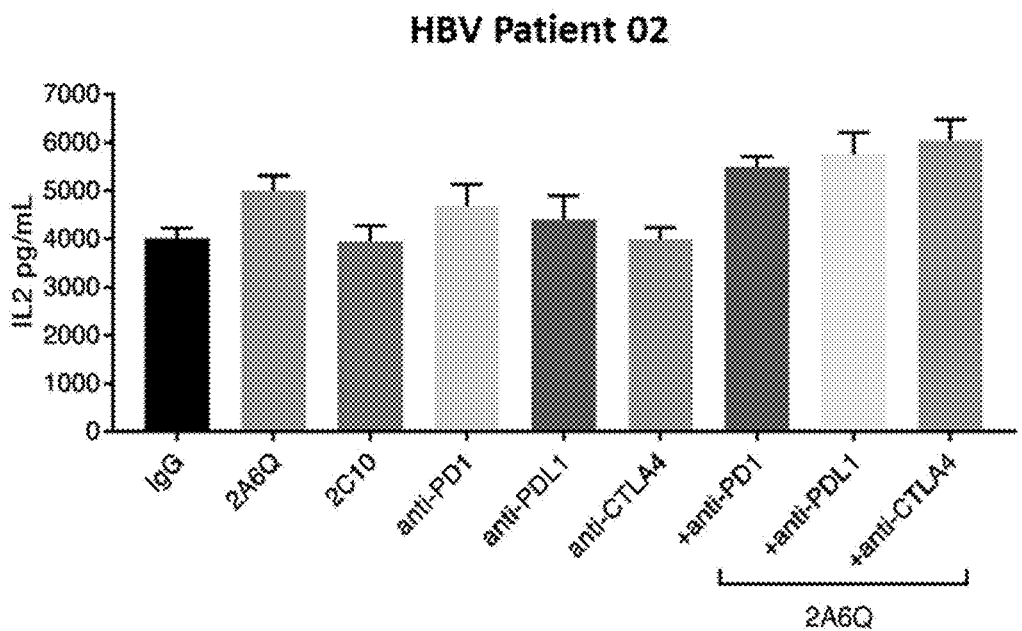
Figure 14C:
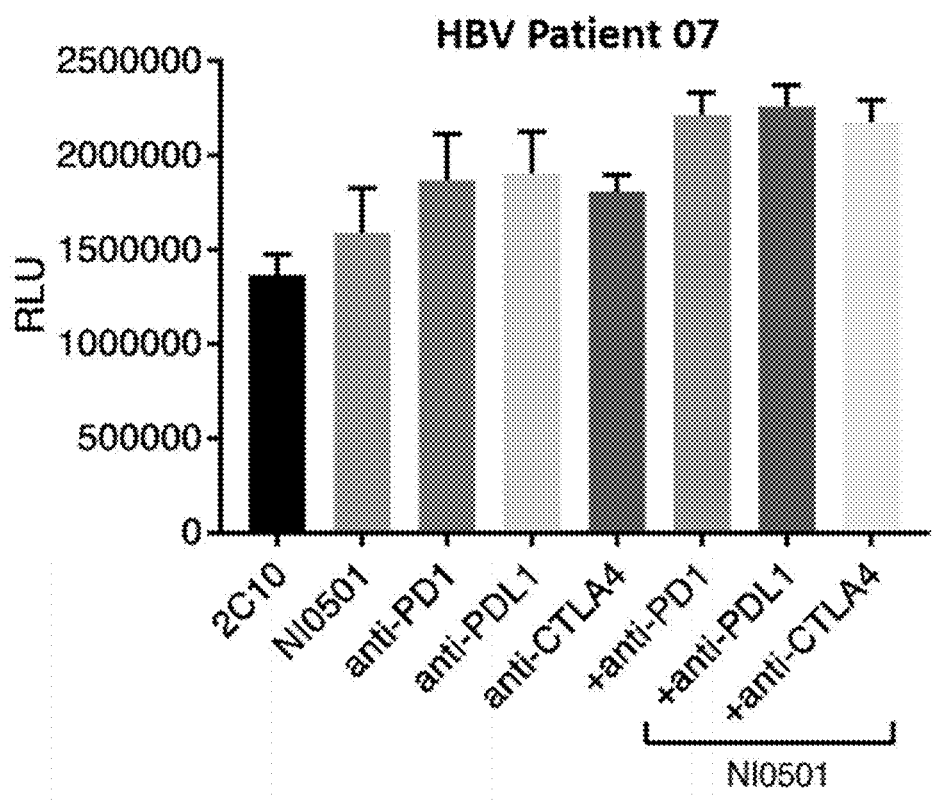

Results:
As shown in FIG. 14A, addition of an IFNγ blocking antibody, AMG811, 2A6Q, or NI0501, alone effectively enhanced cell proliferation when compared to control IgG. As shown in FIG. 14B and FIG. 14C, the combination of the IFNγ blocking antibody, 2A6Q or NI0501, with blocking antibodies of PD-1, PD-L1, or CTLA4 elicited a further enhancement of the immune response as indicated by increased IL2 secretion (FIG. 14B) or increased T cell proliferation (FIG. 14C).

Example 13: IFNγ Blocking Effect Breaks Vaccine Non-Responsiveness

This example illustrates how administration of an IFNγ blocking antibody after inoculation with an HBV vaccine can break non-responsiveness to the vaccine in a mouse model.

Materials and Methods:

The study was carried out using the commercially available mouse surrogate IFNγ antibody, XMG1.2. XMG1.2 neutralizes mouse IFNγ and is described in numerous studies. A hydrodynamic injection (HDI)-based HBV carrier mouse model was used as described in Huang et al., "An immunocompetent mouse model for the tolerance of human chronic hepatitis B virus infection," *Proc Natl Acad Sci USA* Nov. 21, 2006. 103(47); 17862-17867. CBA male 6-week-old to 8-week-old mice were hydrodynamically injected (HDI) with 10 μg of pAAV/HBV1.2 plasmid. Mice with stably established HBV persistence which exhibited high levels of serum HBsAg (HBV-HDI) at 4 weeks post HDI were enrolled for the long-term immunization/treatment experiment. The enrolled HBV-HDI mice were immunized intramuscular with HBsAg vaccine (ENGERIX-B) at day 0. For antibody treatment, the mice were injected intraperitoneally 3 days after vaccination with 300 μg of the mouse IFNγ antibody XMG1.2 (BioXcell clone XMG1.2) or control IgG (BioXcell clone HRPN) and then subsequently at 7 day intervals after vaccination.

Mouse serum levels of HBsAg were determined by Abbott Architect 11000 system (Abbott Diagnostics, Germany). The detection limit is 0.05 IU/mL. HBeAg and anti-HBs levels of the mice were determined by Roche, cobas e 411 analyzer (Roche Diagnostics, GmbH, Mannheim, Germany). The detection limits of HBeAg and anti-S Ab are 1 COI and 10 IU/l, respectively. Serum alanine aminotransferase was measured on an automated clinical chemistry analyzer TBA-200FR (Toshiba, Tokyo, Japan) using ALTGPT reagent (Denka Seiken, Tokyo, Japan).

Results:

At the end of the study, 42 days after vaccination, anti-HBs antibodies could be detected in 22% of the mice treated with XMG1.2 antibody. In contrast, HBsAg vaccination did not induce the production of anti-HBs antibodies in mice treated with control IgG. No significant increase in ALT was observed in all mice enrolled over the treatment period indicating that the neutralizing mouse IFNγ antibody administration did not induce detectable liver injury.

The above results indicate that administration of an anti-IFNγ antibody after immunization with an HBsAg vaccine can break vaccine non-responsiveness in mice. The results thus suggest that administration of an IFNγ neutralizing antibody after vaccination can enhance treatment of chronic HBV infection in humans.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims. Additional embodiments of the invention are set forth in the following claims.

The invention claimed is:

1. A method for treating hepatitis B virus infection, comprising administering to a subject in need thereof a composition comprising a therapeutically effective amount of an IFNγ antibody and a pharmaceutically acceptable carrier.

2. The method of claim 1, wherein the IFNγ antibody modulates a biological function of IFNγ.

3. The method of claim 1, wherein the IFNγ antibody neutralizes IFNγ.

4. The method of claim 1, wherein the IFNγ antibody inhibits, decreases, and/or fully blocks the signaling activity of IFNγ.

5. The method of claim 4, wherein the IFNγ antibody decreases IFNγ signaling activity by pro-human IFNγ, mature-human IFNγ, or truncated-human IFNγ.

6. The method of claim 1, wherein the IFNγ antibody reduces one or more of: IFNγ-dependent cytokine production; IFNγ-dependent T cell dysfunction, IFNγ-dependent immune tolerance, and IFNγ-dependent inflammation.

7. The method of claim 1, wherein the IFNγ antibody reduces expression of HLA-DR and/or PDL1 in monocytes stimulated with IFNγ.

8. The method of claim 1, wherein the IFNγ antibody reduces expression of indoleamine 2,3-dioxygenase (IDO) in monocytes stimulated with IFNγ.

9. The method of claim 1, wherein the IFNγ antibody increases IL-2 production and/or cell proliferation of SEB-stimulated human PBMCs by at least 1.2-fold, at least 1.3-fold, at least 1.4-fold, at least 1.5-fold, at least 1.6-fold, at least 1.7-fold, at least 1.8-fold, at least 1.9-fold, at least 2-fold, at least 2.1-fold, or at least 2.20-fold.

10. The method of claim 1, wherein the IFNγ antibody comprises:
a VH region having a CDR-H1 amino acid sequence selected from SEQ ID NO: 120 or 123, a CDR-H2 amino acid sequence selected from SEQ ID NO: 121 or 124, and a CDR-H3 amino acid sequence selected from SEQ ID NO: 122 or 125; and
a VL region comprising a CDR-L1 amino acid sequence selected from SEQ ID NO: 132 or 135, a CDR-L2 amino acid sequence selected from SEQ ID NO: 133 or 136, and a CDR-L3 amino acid sequence selected from SEQ ID NO: 134 or 137.

11. The method of claim 10, wherein the IFNγ antibody comprises:
(a) a VH region having a CDR-H1 amino acid sequence of SEQ ID NO: 120, a CDR-H2 amino acid sequence of SEQ ID NO: 121, and a CDR-H3 amino acid sequence of SEQ ID NO: 122, and a VL region comprising a CDR-L1 amino acid sequence of SEQ ID NO: 132, a CDR-L2 amino acid sequence of SEQ ID NO: 133, and a CDR-L3 amino acid sequence of SEQ ID NO: 134;
(b) a VH region having a CDR-H1 amino acid sequence of SEQ ID NO: 123, a CDR-H2 amino acid sequence of SEQ ID NO: 124, and a CDR-H3 amino acid sequence of SEQ ID NO: 125, and a VL region comprising a CDR-L1 amino acid sequence of SEQ ID NO: 135, a CDR-L2 amino acid sequence of SEQ ID NO: 136, and a CDR-L3 amino acid sequence of SEQ ID NO: 137; or (c) a VH region having a CDR-H1 amino acid sequence of SEQ ID NO: 123, a CDR-H2 amino acid sequence of SEQ ID NO: 124, and a CDR-H3 amino acid sequence of SEQ ID NO: 125, and a VL region comprising a CDR-L1 amino acid sequence of SEQ ID NO: 132, a CDR-L2 amino acid sequence of SEQ ID NO: 133, and a CDR-L3 amino acid sequence of SEQ ID NO: 134.

12. The method of claim 10, wherein the IFNγ antibody comprises:
(a) a VH region comprising an amino acid sequence having at least 90% identity to SEQ ID NO: 109, 110, 164, or 165; and
(b) a VL region comprising an amino acid sequence having at least 90% identity to SEQ ID NO: 113, or 114.

13. The method of claim 12, wherein the IFNγ antibody comprises:
(a) a VH region amino acid sequence of SEQ ID NO: 109, and a VL region amino acid sequence of SEQ ID NO: 113;
(b) a VH region amino acid sequence of SEQ ID NO: 110, and a VL region amino acid sequence of SEQ ID NO: 114;
(c) a VH region amino acid sequence of SEQ ID NO: 109, and a VL region amino acid sequence of SEQ ID NO: 114;
(d) a VH region amino acid sequence of SEQ ID NO: 110, and a VL region amino acid sequence of SEQ ID NO: 113;
(e) a VH region amino acid sequence of SEQ ID NO: 164, and a VL region amino acid sequence of SEQ ID NO: 113; or (f) a VH region amino acid sequence of SEQ ID NO: 165, and a VL region amino acid sequence of SEQ ID NO: 113.

14. The method of claim 10, wherein the IFNγ antibody comprises:
(a) a heavy chain amino acid sequence having at least 90% identity to SEQ ID NO: 183, 185, 187, or 189; and
(b) a light chain amino acid sequence having at least 90% identity to SEQ ID NO: 184, or 186.

15. The method of claim 14, wherein the IFNγ antibody comprises:
(a) a heavy chain amino acid sequence of SEQ ID NO: 183, and a light chain amino acid sequence of SEQ ID NO: 184;
(b) a heavy chain amino acid sequence of SEQ ID NO: 185, and a light chain amino acid sequence of SEQ ID NO: 186;
(c) a heavy chain amino acid sequence of SEQ ID NO: 183, and a light chain amino acid sequence of SEQ ID NO: 186;
(d) a heavy chain amino acid sequence of SEQ ID NO: 185, and a light chain amino acid sequence of SEQ ID NO: 184;
(e) a heavy chain amino acid sequence of SEQ ID NO: 187, and a light chain amino acid sequence of SEQ ID NO: 184; or (f) a heavy chain amino acid sequence of SEQ ID NO: 189, and a light chain amino acid sequence of SEQ ID NO: 184.

16. The method of claim 10, wherein the VH region of the IFNγ antibody further comprises an amino acid substitution selected from N76A and N76Q.

17. The method of claim 1, wherein the IFNγ antibody is an antibody selected from the group consisting of 2A6, 2B6, 2A6A, 2A6Q, AB, BA, AMG811, and NI0105.

18. The method of claim 1, wherein the subject in need is an HBV carrier, one with chronic HBV infection, or one with HBV persistence.

19. The method of claim 1, further comprising administering at least one additional therapeutic agent.

20. The method of claim 19, wherein the additional therapeutic agent is an HBV vaccine.

21. The method of claim 19, wherein the additional therapeutic agent is an antibody that targets an inhibitory immune checkpoint molecule.

22. The method of claim 21, wherein the antibody that targets an inhibitory immune checkpoint molecule is selected from an anti-PD1, anti-PD-L1, and an anti-CTLA-4.

23. The method of claim 19, wherein the additional therapeutic agent is selected from the group consisting of: entecavir (Baraclude), tenofovir (Viread), lamivudine (Epivir), adefovir (Hepsera) and telbivudine (Tyzeka), interferon alfa-2b, and pegyinterferon alfa-2a.

24. The method of claim 1, wherein an immune response against HBV is induced or boosted in the subject in need, or seroconversion with respect to HBV is induced in the subject in need by the therapeutically effective amount of the composition.

25. The method of claim 1, wherein after administering the composition to the subject in need, HBsAg in the subject is reduced.

26. The method of claim 1, wherein after administering the composition to the subject in need, the viral load of HBV in the subject is reduced.

27. The method of claim 1, wherein the IFNγ antibody binds to human IFNγ with a binding affinity of $1\times10^{-8}$ M or less, $1\times10^{-9}$ M or less, $1\times10^{-10}$ M or less, or $1\times10^{-11}$ M or less.

28. The method of claim 1, wherein the IFNγ antibody binds to human IFNγ and to cynomolgus monkey IFNγ with a binding affinity of $1\times10^{-8}$ M or less, $1\times10^{-9}$ M or less, $1\times10^{-10}$ M or less, or $1\times10^{-11}$ M or less.

* * * * *

UNITED STATES PATENT AND TRADEMARK OFFICE
CERTIFICATE OF CORRECTION

PATENT NO. : 10,813,974 B2
APPLICATION NO. : 16/889483
DATED : October 27, 2020
INVENTOR(S) : Hung-Kai Chen et al.

Page 1 of 1

It is certified that error appears in the above-identified patent and that said Letters Patent is hereby corrected as shown below:

In the Specification

Column 3, Line 60, "189" should be changed to --188--.

Column 4, Line 14, "189" should be changed to --188--.

Column 4, Line 21, "NI0105" should be changed to --NI0501--.

In the Claims

Claim 14 Column 122, Line 33, "189" should be changed to --188--.

Claim 15 Column 122, Line 53, "189" should be changed to --188--.

Claim 17 Column 122, Line 60, "NI0105" should be changed to --NI0501--.

Claim 27 Column 123, Lines 26-27, ", $1\times10\text{-}9$ M or less, $1\times10\text{-}10$ M or less, or $1\times10\text{-}11$ M or less" should be deleted.

Claim 28 Column 123, Lines 30-31, ", $1\times10\text{-}9$ M or less, $1\times10\text{-}10$ M or less, or $1\times10\text{-}11$ M or less" should be deleted.

Signed and Sealed this
Twenty-ninth Day of December, 2020

Andrei Iancu
*Director of the United States Patent and Trademark Office*